(12) United States Patent
Cowley et al.

(10) Patent No.: US 10,167,257 B2
(45) Date of Patent: Jan. 1, 2019

(54) INDOLE DERIVATIVES FOR USE IN MEDICINE

(71) Applicant: IOmet Pharma Ltd., Edinburgh, Midlothian (GB)

(72) Inventors: Phillip M. Cowley, Edinburgh (GB); Alan Wise, Edinburgh (GB); Michael Kiczun, Dundee (GB); Susan Davis, Dundee (GB)

(73) Assignee: Iomet Pharma Ltd., Midlothian (GB)

( * ) Notice: Subject to any disclaimer, the term of this patent is extended or adjusted under 35 U.S.C. 154(b) by 0 days.

(21) Appl. No.: 15/301,619

(22) PCT Filed: Mar. 19, 2015

(86) PCT No.: PCT/EP2015/055823
§ 371 (c)(1),
(2) Date: Oct. 3, 2016

(87) PCT Pub. No.: WO2015/150097
PCT Pub. Date: Oct. 8, 2015

(65) Prior Publication Data
US 2017/0107178 A1 Apr. 20, 2017

(30) Foreign Application Priority Data

Apr. 4, 2014 (GB) .................................. 1406154.3
Feb. 10, 2015 (GB) .................................. 1502156.1

(51) Int. Cl.
*C07D 401/12* (2006.01)
*C07D 403/12* (2006.01)
(Continued)

(52) U.S. Cl.
CPC .......... *C07D 209/42* (2013.01); *A61K 31/404* (2013.01); *A61K 31/405* (2013.01); *A61K 31/407* (2013.01); *A61K 31/4045* (2013.01); *A61K 31/416* (2013.01); *A61K 31/4155* (2013.01); *A61K 31/4178* (2013.01); *A61K 31/4184* (2013.01); *A61K 31/4188* (2013.01); *A61K 31/4196* (2013.01); *A61K 31/422* (2013.01); *A61K 31/423* (2013.01);
(Continued)

(58) Field of Classification Search
CPC .. C07D 209/42; C07D 401/12; C07D 405/12; C07D 409/12
See application file for complete search history.

(56) References Cited

U.S. PATENT DOCUMENTS 3,699,123 A 10/1972 Seeman et al.
5,527,819 A 6/1996 Williams et al.
(Continued)

FOREIGN PATENT DOCUMENTS

JP 2012107001 6/2012
WO 200127103 A1 4/2001
(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Hoover, Indole-2-carboxamide inhibitors of human liver glycogen phosphorylase, J. Med. Chem., 1998, 2934-2938, 41-16.
Laregina, New Nitrogen containing substituents at the indole-2-carboxamide yield high potent and broad spectrum indolylarylsulfone HIV-1 non-nucleoside reverse transcriptase inhibitors, J. Med. Chem., 2012, 6634-6638, 55-14.
Laregina, Synthesis, structure-activity relationships and molecular modeling studies of new indole inhibitors of monoamine oxidases A and B, Bioorganic & Medicinal Chemistry, 2008, 9729-9740, 16-22.
(Continued)

*Primary Examiner* — Shawquia Jackson
(74) *Attorney, Agent, or Firm* — Yong Zhao; Catherine D. Fitch

(57) ABSTRACT

Provided is a tryptophan-2,3-dioxygenase (TDO) and/or indoleamine-2,3-dioxygenase (IDO) inhibitor compound for use in medicine, which compound comprises the following formula: wherein $X^1$, $X^2$, $X^3$, $X^4$, and $X^5$ may be the same or different and each is independently selected from C, N and O; each atom having a dotted line may independently have a double bond or a single bond, provided that valencies at each atom are maintained; each $R^1$, $R^2$, $R^3$, $R^4$, $R^5$, and $R^7$ may be present or absent and may be the same or different and is selected from H and a substituted or unsubstituted organic group, provided that the number of such R groups present is such that the valencies of $X^1$, $X^2$, $X^3$, $X^4$, and $X^5$ are maintained; one or two $R^6$ groups may be present and are selected from H and a substituted or unsubstituted organic group, provided that the number of $R^6$ groups present is such that the valency of the carbon atom to which they are attached is maintained, and provided that at least one $R^6$ is an organic group comprising an atom double-bonded to an oxygen atom (preferably a carbonyl group or a sulphonyl group) at an α-, β-, or γ-position to the carbon atom to which the $R^6$ is attached and in which the atom double-bonded to an oxygen atom is also bonded to a hetero-atom.

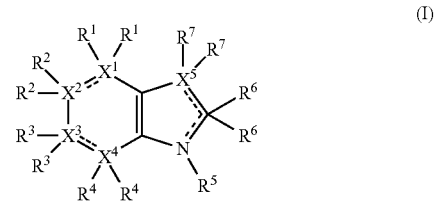

(I)

24 Claims, 2 Drawing Sheets

Figure 1:
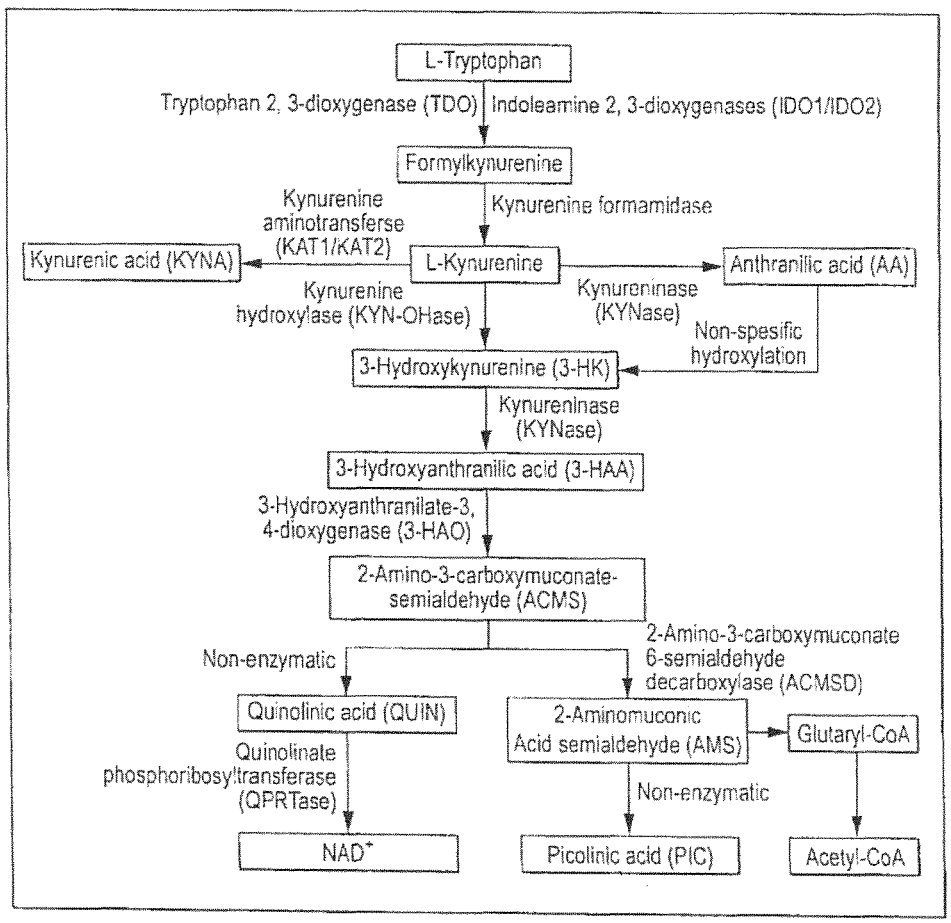

(51) Int. Cl.
| | |
|---|---|
| C07D 405/12 | (2006.01) |
| C07D 409/12 | (2006.01) |
| C07D 209/42 | (2006.01) |
| A61K 31/404 | (2006.01) |
| A61K 31/4045 | (2006.01) |
| A61K 31/405 | (2006.01) |
| A61K 31/407 | (2006.01) |
| A61K 31/4184 | (2006.01) |
| A61K 31/4188 | (2006.01) |
| A61K 31/423 | (2006.01) |
| A61K 31/424 | (2006.01) |
| A61K 31/4355 | (2006.01) |
| A61K 31/437 | (2006.01) |
| A61K 31/4155 | (2006.01) |
| A61K 31/416 | (2006.01) |
| A61K 31/4178 | (2006.01) |
| A61K 31/4196 | (2006.01) |
| A61K 31/422 | (2006.01) |
| A61K 31/4245 | (2006.01) |
| A61K 31/427 | (2006.01) |
| A61K 31/4439 | (2006.01) |
| A61K 31/454 | (2006.01) |
| A61K 31/475 | (2006.01) |
| A61K 31/496 | (2006.01) |
| A61K 31/506 | (2006.01) |
| A61K 31/517 | (2006.01) |
| A61K 31/5377 | (2006.01) |
| A61K 45/06 | (2006.01) |
| C07D 263/58 | (2006.01) |
| C07D 405/14 | (2006.01) |
| C07D 413/12 | (2006.01) |
| C07D 417/12 | (2006.01) |
| C07D 471/04 | (2006.01) |

(52) U.S. Cl.
CPC .......... *A61K 31/424* (2013.01); *A61K 31/427* (2013.01); *A61K 31/4245* (2013.01); *A61K 31/437* (2013.01); *A61K 31/4355* (2013.01); *A61K 31/4439* (2013.01); *A61K 31/454* (2013.01); *A61K 31/475* (2013.01); *A61K 31/496* (2013.01); *A61K 31/506* (2013.01); *A61K 31/517* (2013.01); *A61K 31/5377* (2013.01); *A61K 45/06* (2013.01); *C07D 263/58* (2013.01); *C07D 401/12* (2013.01); *C07D 403/12* (2013.01); *C07D 405/12* (2013.01); *C07D 405/14* (2013.01); *C07D 409/12* (2013.01); *C07D 413/12* (2013.01); *C07D 417/12* (2013.01); *C07D 471/04* (2013.01)

(56) References Cited

U.S. PATENT DOCUMENTS

| | | | |
|---|---|---|---|
| 6,989,385 | B2 | 1/2006 | Bebbington et al. |
| 7,691,853 | B2 | 4/2010 | Bebbington et al. |
| 7,723,391 | B2 | 5/2010 | Du Bois et al. |
| 7,935,824 | B2 | 5/2011 | Yoshino et al. |
| 8,927,550 | B2 | 1/2015 | Cook et al. |
| 2009/0047246 | A1 | 2/2009 | Beigelman et al. |
| 2011/0086834 | A1 | 4/2011 | Chen et al. |
| 2011/0136807 | A1 | 6/2011 | Hangauer, Jr. |
| 2015/0274703 | A1 | 10/2015 | Boldron et al. |

FOREIGN PATENT DOCUMENTS

| | | |
|---|---|---|
| WO | WO2008036967 A2 | 3/2008 |
| WO | WO2008152099 A2 | 12/2008 |
| WO | 2009158011 | 12/2009 |
| WO | 2009158375 | 12/2009 |
| WO | WO2011050245 A1 | 4/2011 |
| WO | WO2012174488 A2 | 12/2012 |
| WO | 2014037900 | 3/2014 |
| WO | WO2015150097 | 10/2015 |

OTHER PUBLICATIONS

Onda, Design, synthesis, and pharmacological evaluation of N-bicyclo-5-chloro-1H-indole-2-carboxamide derivatives as potent glycogen phosphorylase inhibitors, Bioorganic & Medicinal Chemistry, 2008, 10001-10012, 16-23.

Onda, Synthesis of 5-chloro-N-aryl-1H-indole-2-carboxamide derivatives as inhibitors of human liver glycogen phophorylase, Bioorganic & Medicinal Chemistry, 2008, 5452-5464, 16-10.

Piscitelli, Indolylarylsulfones bearing natural and unnatural amino acids. Discovery of potent inhibitors of HIV-1 non-nucleoside wild type and resistant mutant strains reverse transciptase and coxsackie B4 virus, J. Med. Chem., 2009, 1922-1934, 52-7.

Shelke, Exploration of new scaffolds as potential MAO-A inhibitors using pharmacophore and 3D-QSAR based In silico screening, Bioorganic & Medicinal Chemistry Letters, 2011, 2419-2424, 21-8.

White, Synthesis and evaluation of novel anti-proliferative pyrroloazepinone and indooazepinone oximes derived from the marine natural product hymenialdisine, European Journal of Medicinal Chemistry, 2012, 246-253, 56.

Dolusic, Discovery and preliminary SARs of keto-indoles as novel indoleamine 2,3-dioxygenase (IDO) inhibitors, European Journal of Medicinal Chamistry, 2011, 3058-3065, 46.

Kamlendra, 3D-QSAR study of indol-2-yl ethanones derivatives as novel indoleamine 2,3-dioxygenase (IDO) inhibitors, E-Journal of Chemistry, 2012, 1753-1759, 9-4.

Tsotinis, C5,C6-Disubstituted 1H-Indole-2-Carboxamides: Synthesis and Cytotoxic Activity in the Human Non-Small Lung Cancer Cell Line NSCLC-N16-L16, Letters in Drug Design and Discovery, 2006, 14-16, 3-1.

Australian Examination Search Report, dated Sep. 11, 2017, 5 pages.

CAS Registry No. 1389258-25-6, STN Entry Date Aug. 10, 2012; 6-bromo-N-[1-(5-methyl-1,2,4-oxadiazol-3-yl) cyclopentyl]-1H-Indole-2-carboxamide.

CAS Registry No. 1278518-30-1, STN Entry Date Apr. 11, 2011; 6-ethoxy-N-[1-(5-methyl-1,2,4-oxadiazol-3-yl) cyclohexyl]-1H-indole-2-carboxamide.

CAS Registry No. 1259136-02-1, STN Entry Date Jan. 12, 2011; 6-methoxy-N-[1-(5-methyl-1,2,4-oxadiazol-3-yl) cyclohexyl]-1H-indole-2-carboxamide.

CAS Registry No. 1281151-50-5, STN Entry Date Apr. 17, 2011; 6-methoxy-N-(1-phenylcyclobutyl)-1H-Indole-2-carboxamide.

CAS Registry No. 1288651-92-2, STN Entry Date May 1, 2011; N-[4-(4-chlorophenyl)tetrahydro-2H-pyran-4-yl]-4,6,7-trimethoxy-1H-indole-2-carboxamide.

CAS Registry No. 1288651-93-3, STN Entry Date May 1, 2011; N-[4-(4-chlorophenyl)tetrahydro-2H-pyran-4-yl]-6-methoxy-1H-indole-2-carboxamide.

CAS Registry No. 1292636-71-5, STN Entry Date May 10, 2011; N-(1-methylcyclopentyl)-1H-indole-2-carboxamide.

CAS Registry No. 1294468-55-5, STN Entry Date May 13, 2011; 1-ethyl-N-[1-(5-methyl-1,2,4-oxadiazol-3-yl) cyclohexyl]-1H-indole-2-carboxamide.

CAS Registry No. 1301125-03-0, STN Entry Date May 26, 2011; N-[4-(4-chlorophenyl)tetrahydro-2H-pyran-4-yl]-1H-indole-2-carboxamide.

CAS Registry No. 1306701-63-2, STN Entry Date Jun. 6, 2011; N-(1-methylcyclohexyl)-1H-indole-2-carboxamide.

CAS Registry No. 1316529-77-7, STN Entry Date Aug. 12, 2011; N-[4-(3-bromophenyl)tetrahydro-2H-pyran-4-yl]-6-chloro-1H-Indole-2-carboxamide.

CAS Registry No. 1319380-70-5, STN Entry Date Aug. 18, 2011; N-[1-(4-bromophenyl)cyclopropyl]-4-fluoro-1H-indole-2-carboxamide.

(56) References Cited

OTHER PUBLICATIONS

CAS Registry No. 1320021-62-2, STN Entry Date Aug. 19, 2011; 4-fluoro-N-(1-phenylcyclobutyl)-1H-indole-2-carboxamide.
CAS Registry No. 1320672-13-6, STN Entry Date Aug. 21, 2011; 5-fluoro-N-(1-phenylcyclobutyl)-1H-indole-2-carboxamide.
CAS Registry No. 1320975-33-4, STN Entry Date Aug. 21, 2011; N-(1-phenylcyclobutyl)-1H-indole-2-carboxamide.
CAS Registry No. 1322346-45-1, STN Entry Date Aug. 24, 2011; N-[4-(3-bromophenyl)tetrahydro-2H-pyran-4-yl]-4,6-dimethyl-1H-indole-2-carboxamide.
CAS Registry No. 1322358-45-1, STN Entry Date Aug. 24, 2011; N-[1-(4-fluorophenyl)cyclopentyl]-4,6,7-trimethoxy-1H-indole-2-carboxamide.
CAS Registry No. 1389072-47-2, STN Entry Date 102 Aug. 2012; 4-fluoro-N-[1-(5-methyl-1,2,4-oxadiazol-3-yl)cyclopentyl]-1H-indole-2-carboxamide .
CAS Registry No. 1389121-42-9, STN Entry Date Aug. 12, 2012; 6-methoxy-N-[1-(5-methyl-1,2,4-oxadiazol-3-yl)cyclopentyl]-1H-indole-2-carboxamide.
CAS Registry No. 1389257-93-5, STN Entry Date Aug. 10, 2012; 4,6-dimethyl-N-[1-(5-methyl-1,2,4-oxadiazol-3-yl)cyclopentyl]-1H-indole-2-carboxamide.
CAS Registry No. 1389258-09-6, STN Entry Date Aug. 10, 2012; 5-chloro-N-[1-(5-methyl-1,2,4-oxadiazol-3-yl)cyclopentyl]-1H-Indole-2-carboxamide.
CAS Registry No. 1422924-81-9, STN Entry Date Mar. 11, 2013; N-[1-(3-chlorophenyl)cyclopropyl]-5-methoxy-1-methyl-1H-indole-2-carboxamide.
CAS Registry No. 1423881-28-0, STN Entry Date Mar. 15, 2013; 6-ethoxy-N-(1-methylcyclobutyl)-1H-indole-2-carboxamide.
CAS Registry No. 1424400-44-1, STN Entry Date Mar. 15, 2013; 6-(1,1-dimethylethyl)-N-[1-(5-methyl-1,2,4-oxadiazol-3-yl)cyclohexyl]-1H-Indole-2-carboxamide.
Onajole, O. K. et al. "Preliminary structure-activity relationships and biological evaluation of novel antitubercular indolecarboxamide derivatives against drug-susceptible and drug-resistant *Mycobacterium tuberculosis* strains", Journal of Medicinal Chemistry, 2013, 56, 4093-4103.
Schroeder, G. M. et al. "Improved conditions for converting sterically hindered amides to 1,5-disubstituted tetrazoles", Tetrahedron Letters, 2010, 51, 1404-1406.
Sharma, S. K. et al. "Synthesis of iodo-indoloazepinones in an iodine-mediated three-component domino reaction via a regioselective 7-endo-dig iodo-cyclization pathway", Journal of Organic Chemistry, 2011, 76, 6798-6805.
Ekins, Sean, et al., Three-Dimensional Quantitative Structure-Acitvity Relationship Analysis of Human CYP51 Inhibitors, The American Society for Pharmacology and Experimental Therapeutics, 2007, p. 493-500, vol. 35, No. 3.

\* cited by examiner

INDOLE DERIVATIVES FOR USE IN MEDICINE

CROSS-REFERENCE TO RELATED APPLICATIONS

This application is a U.S. National Phase application under 35 U.S.C. § 371 of PCT Application No. PCT/EP2015/055823, filed Mar. 19, 2015, which published as WO 2015/150097 A1 on Oct. 8, 2015, and claims priority from GB Patent Application Numbers 1406154.3 and 1502156.1, filed Apr. 4, 2014 and Feb. 10, 2015, respectively.

The present invention relates to tryptophan-2,3-dioxygenase (TDO) or indoleamine-2,3-dioxygenase (IDO [IDO1 or IDO2]) inhibitors, and in particular TDO and IDO inhibitors for use in medicine. The inhibitors of the invention may be used in pharmaceutical compositions, and in particular pharmaceutical compositions for treating a cancer, an inflammatory condition, an infectious disease, a central nervous system disease or disorder and other diseases, conditions and disorders. The invention also relates to methods of manufacture of such inhibitors, and methods of treatment using such inhibitors.

Tryptophan Metabolism

The kynurenine pathway (KP) is responsible for >95% of the degradation of the essential amino acid tryptophan. The kynurenine pathway for tryptophan metabolism leads to the production of the essential pyridine nucleotide NAD+ and a number of neuroactive metabolites, including kynurenine (KYN), kynurenic acid (KYNA), the neurotoxic free-radical generator 3-hydroxykynurenine (3-HK), anthranilic acid, 3-HAA, picolinic acid (PIC), and the excitatory N-methyl-D-aspartate (NMDA) receptor agonist and neurotoxin, quinolinic acid (QUIN) (see FIG. 1). The remaining 5% of tryptophan is metabolised by tryptophan hydroxylase to 5-hydroxytryptophan and then further to 5-hydroxytryptamine (serotonin) and melatonin.

Both the depletion of tryptophan and accumulation of immunosuppressive tryptophan catabolites act to supress antigen-specific T-cell and natural killer cell responses and induce the formation of regulatory T cells. Because tryptophan catabolism is induced by inflammatory mediators, notably IFN-γ, it is thought to represent an endogenous mechanism that restricts excessive immune responses, thereby preventing immunopathology. However, there is evidence that in disease states this feedback loop may not be beneficial (reviewed in (Munn and Mellor, 2013).

IDO/TDO

The first step of tryptophan catabolism is catalysed by either TDO or IDO. Both enzymes catalyze the oxidative cleavage of the 2,3 double bond in the indole ring, converting tryptophan to N-formylkynurenine. This is the rate-limiting step in tryptophan catabolism by the kynurenine pathway (Grohmann et al., 2003; Stone and Darlington, 2002). TDO is a homotetramer with each monomer having a molecular mass of 48 kDa, whereas IDO has a molecular mass of 45 kDa and a monomeric structure (Sugimoto et al., 2006; Thackray et al., 2008; Zhang et al., 2007). Despite mediating the same reaction, TDO and IDO are structurally distinct, sharing only 10% homology mainly within the active site (Thackray et al., 2008).

TDO is expressed at high levels in the liver and is responsible for regulating systemic tryptophan levels. TDO is not induced or regulated by signals from the immune system, however TDO expression can be induced by tryptophan or corticosteroids (Miller et al., 2004; Salter and Pogson, 1985). More recently, TDO has been found to be expressed in the brain, where it regulates the production of neuroactive tryptophan metabolites such as kynurenic acid and quinolinic acid (Kanai et al., 2009).

IDO is the predominant tryptophan catabolising enzyme extra hepatically and is found in numerous cells, including macrophages, microglia, neurons and astrocytes (Guillemin et al., 2007; Guillemin et al., 2001; Guillemin et al., 2003; Guillemin et al., 2005). IDO transcription is stringently controlled, responding to specific inflammatory mediators. The mouse and human IDO gene promoters contain multiple sequence elements that confer responsiveness to type I (IFN-α/β) and, more potently, type II (IFN-γ) interferons (Chang et al., 2011; Dai and Gupta, 1990; Hassanain et al., 1993; Mellor et al., 2003). Various cell types, including certain myeloid-lineage cells (monocyte-derived macrophages and DCs), fibroblasts, endothelial cells and some tumour-cell lines, express IDO after exposure to IFN-γ (Burke et al., 1995; Hwu et al., 2000; Mellor et al., 2003; Munn et al., 1999; Varga et al., 1996). However, the control of IDO transcription is complex and cell-type specific. IDO activity is found constitutively at the maternal—fetal interface, expressed by human extravillous trophoblast cells (Kudo and Boyd, 2000). Outside of the placenta, functional IDO expression was reported to be highest in the mouse epididymis, gut (distal ileum and colon), lymph nodes, spleen, thymus and lungs (Takikawa et al., 1986).

Another recent variant enzyme of IDO has been shown to catalyse the same enzymatic step: indoleamine-2,3-dioxygenase 2 (IDO2). However, its physiological relevance remains unclear due to its very low activity, the presence of common polymorphisms that inactivate its enzymatic activity in approximately half of all Caucasians and Asians, and the presence of multiple splice variants (Lob et al., 2008; Meininger et al., 2011; Metz et al., 2007).

IDO-deficient mice are at a gross level phenotypical normal (Mellor et al., 2003), however, they are slightly more prone to induction of autoimmunity and stimulation of the innate immune system. IDO−/− knockout mice also display enhanced inflammatory-mediated colon carcinogenesis and exhibit resistance to inflammation-driven lung and skin cancers (Chang et al., 2011; Yan et al., 2010).

The TDO−/− knockout mouse appears phenotypically normal. However, the TDO knockout mice have a 9-fold increase in the plasma concentration of L-Trp, while IDO−/− knockout mice had WT levels of L-Trp, this suggests that TDO and not IDO regulates systemic Trp. TDO ablation increases Trp in the brain as well as serotonin (5-HT) and is therefore a modulator of anxiety related behaviour (Kanai et al., 2009). TDO also plays a role in the maintenance of brain morphology in adult mice as TDO−/− mice show increased neurogenesis in the hippocampus and subventricular zone during adulthood (Funakoshi et al., 2011).

Immuno-Modulation: Tryptophan Depletion and Kynurenine Accumulation

Immunoregulation by tryptophan metabolism modulates the immune system by depletion of the TDO/IDO substrate (tryptophan) in the microenvironment and the accumulation of products such as kynurenine.

Effector T cells are particularly susceptible to low tryptophan concentrations, therefore, depletion of the essential amino acid tryptophan from the local microenvironment resulting in effector T-cell anergy and apoptosis. The depletion of tryptophan is detected by the general control non-derepressible-2 kinase (GCN2) (Munn et al., 2005). The activation of GCN2 triggers a stress-response program that results in cell-cycle arrest, differentiation, adaptation or apoptosis. T cells lacking GCN2 in mice are not susceptible to IDO-mediated anergy by myeloid cells, including dendritic cells in tumor-draining lymph nodes (Munn et al., 2005).

Tryptophan metabolites such as kynurenine, kynurenic acid, 3-hydroxy-kynurenine, and 3-hydroxy-anthranilic acid suppress T-cell function and are capable of inducing T-cell apoptosis. Recent studies have shown that the aryl hydrocarbon receptor (AHR) is a direct target of kynurenine (Mezrich et al., 2010; Nguyen et al., 2010; Opitz et al., 2011). The AHR is a basic helix-loop-helix Per-Arnt-Sim (PAS) family transcription factor. As kynurenine accumulates in a tumour, KYN binds the AHR, translocates to the nucleus and activates transcription of target genes regulated by dioxin-responsive elements (DREs). In T-helper-cells kynurenine results in the generation of regulatory T cells (Treg).

Pharmacological inhibitors of TDO and/or IDO have utility in a wide range of indications, including Infectious diseases, cancer, neurological conditions and many other diseases.

Infectious Diseases and Inflammation

Infection by bacteria, parasites, or viruses induces a strong IFN-γ-dependent inflammatory response. IDO can dampen protective host immunity, thus indirectly leading to increased pathogen burdens. For example, IDO activity attenuates *Toxoplasma gondii* replication in the lung, and the inflammatory damage is significantly decreased by the administration of the IDO inhibitor 1MT after infection (Murakami et al., 2012). Also, in mice infected with murine leukaemia virus (MuLV), IDO was found to be highly expressed, and ablation of IDO enhanced control of viral replication and increased survival (Hoshi et al., 2010). In a model of influenza infection, the immunosuppressive effects of IDO could predispose lungs to secondary bacterial infection (van der Sluijs, et al 2006). In Chagas Disease, which is caused by the *Trypanosoma cruzi* parasite, kynurenine is increased in patients and correlates with disease severity (Maranon et al., 2013). Therefore, IDO inhibitors could be used to improve the outcomes of patients with a wide variety of infectious diseases and inflammatory conditions. Given the role of TDO in controlling systemic Trp levels, TDO inhibitors could also be used to improve the outcomes of patients with a wide variety of infectious diseases and inflammatory conditions.

IDO and Immunity to Gut Bacteria

IDO plays a role in regulating mucosal immunity to the intestinal microbiota. IDO has been shown to regulate commensal induced antibody production in the gut; IDO-deficient mice had elevated baseline levels of immunoglobulin A (IgA) and immunoglobulin G (IgG) in the serum and increased IgA in intestinal secretions. Due to elevated antibody production, IDO deficient mice were more resistant to intestinal colonization by the gram-negative enteric bacterial pathogen *Citrobacter rodentium* than WT mice. IDO-deficient mice also displayed enhanced resistance to the colitis caused by infection with *C. rodentium* (Harrington et al., 2008).

Therefore, pharmacological targeting of IDO activity may represent a new approach to manipulating intestinal immunity and controlling the pathology caused by enteric pathogens including colitis (Harrington et al., 2008).

HIV Infection

Patients infected with HIV have chronically reduced levels of plasma tryptophan and increased levels of kynurenine, and increased IDO expression (Fuchs et al., 1990 and Zangerle et al., 2002).

In HIV patients the upregulation of IDO acts to suppress immune responses to HIV antigens contributing to the immune evasion of the virus. HIV triggers high levels of IDO expression when it infects human macrophages in vitro (Grant et al., 2000), and simian immunodeficiency virus (SIV) infection of the brain in vivo induces IDO expression by cells of the macrophage lineage (Burudi et al., 2002).

The pathogenesis of HIV is characterized by CD4+ T cell depletion and chronic T cell activation, leading ultimately to AIDS (Douek et al., 2009). CD4+ T helper (TH) cells provide protective immunity and immune regulation through different immune cell functional subsets, including TH1, TH2, T regulatory (Treg), and TH17 cells. Progressive HIV is associated with the loss of TH17 cells and a reciprocal increase in the fraction of the immunosuppressive Treg cells. The loss of TH17/Treg balance is associated with induction of IDO by myeloid antigen-presenting dendritic cells (Favre et al., 2010). In vitro, the loss of TH17/Treg balance is mediated directly by the proximal tryptophan catabolite from IDO metabolism, 3-hydroxyanthranilic acid. Therefore in progressive HIV, induction of IDO contributes to the inversion of the TH17/Treg balance and maintenance of a chronic inflammatory state (Favre et al., 2010). Therefore, IDO inhibitors could have utility in addressing the TH17/Treg balance in HIV.

Sepsis-Induced Hypotension

Systemic inflammation such as sepsis is characterized by arterial hypotension and systemic inflammatory response syndrome (Riedemann et al., 2003). The associated increase in circulating pro-inflammatory cytokines, including interferon-γ (IFN-γ), leads to the unchecked production of effector molecules such as reactive oxygen and nitrogen species that themselves can contribute to pathology (Riedemann et al., 2003).

The metabolism of tryptophan to kynurenine by IDO expressed in endothelial cells contributes to arterial vessel relaxation and the control of blood pressure (Wang et al., 2010). Infection of mice with malarial parasites (*Plasmodium berghei*), and experimental induction of endotoxemia, caused endothelial expression of IDO, resulting in decreased plasma tryptophan, increased kynurenine, and hypotension. Pharmacological inhibition of IDO increased blood pressure in systemically inflamed mice, but not in mice deficient for IDO or interferon-γ, which is required for IDO induction. Arterial relaxation by kynurenine was mediated by activation of the adenylate and soluble guanylate cyclase pathways. (Wang et al., 2010). Therefore, inhibitors of IDO (and TDO, given its role in controlling systemic Trp levels) could have utility in treating sepsis-induced hypotension.

CNS Disorders

In the central nervous system both fates of TRP which act as a precursor to kynurenine and serotonin are pathways of interest and importance. Metabolites produced by the kynurenine pathway have been implicated to play a role in the pathomechanism of neuroinflammatory and neurodegenerative disorder (summarised in FIG. 2). The first stable intermediate from the kynurenine pathway is KYN. Subsequently, several neuroactive intermediates are generated. They include kynurenic acid (KYNA), 3-hydroxykynurenine (3-HK), and quinolinic acid (QUIN). 3-HK and QUIN are neurotoxic by distinct mechanisms; 3-HK is a potent free-radical generator (Hiraku et al., 1995; Ishii et al., 1992; Thevandavakkam et al., 2010), whereas QUIN is an excitotoxic N-methyl-D-aspartate (NMDA) receptor agonist (Schwarcz et al., 1983; Stone and Perkins, 1981). KYNA, on the other hand, has neuroprotective properties as an antagonist of excitatory amino acid receptors and a free-radical scavenger (Carpenedo et al., 2001; Foster et al., 1984; Goda et al., 1999; Vecsei and Beal, 1990). Changes in the concentration levels of kynurenines can shift the balance to pathological conditions. The ability to influence the metabolism towards the neuroprotective branch of the kynurenine pathway, i.e. towards kynurenic acid (KYNA) synthesis, may be one option in preventing neurodegenerative diseases.

In the CNS, the kynurenine pathway is present to varying extents in most cell types, Infiltrating macrophages, activated microglia and neurons have the complete repertoire of kynurenine pathway enzymes. On the other hand, neuroprotective astrocytes and oligodendrocytes lack the enzyme, kynurenine 3-monooxygenase (KMO) and IDO respectively, and are incapable of synthesizing the excitotoxin, quinolinic acid (QUIN) (Guillemin et al., 2000; Lim et al., 2007). TDO is expressed in low quantities in the brain, and is induced by TRP or corticosteroids (Salter and Pogson 1985; Miller et al., 2004).

Given the role of TDO and IDO in the pathogenesis of several CNS disorders as well as the role of TDO in controlling systemic Trp levels, IDO and/or TDO inhibitors could be used to improve the outcomes of patients with a wide variety of CNS diseases and neurodegeneration.

Amyotrophic Lateral Sclerosis

Amyotrophic lateral sclerosis (ALS), or Lou Gehrig's disease, is a progressive and fatal neurodegenerative disease targeting the motor system. ALS results in the selective attacking and destruction of motor neurons in the motor cortex, brainstem and spinal cord.

Although multiple mechanisms are likely to contribute to ALS, the kynurenine pathway activated during neuroinflammation is emerging as a contributing factor. Initial inflammation may inflict a nonlethal injury to motor neurons of individuals with a susceptible genetic constitution, in turn triggering a progressive inflammatory process which activates microglia to produce neurotoxic kynurenine metabolites that further destroy motor neurons.

In the brain and spinal cord of ALS patients large numbers of activated microglia, reactive astrocytes, T cells and infiltrating macrophages have been observed (Graves et al., 2004; Henkel et al., 2004). These cells release inflammatory and neurotoxic mediators, among others IFN-γ, the most potent inducer of IDO (McGeer and McGeer 2002). The neuronal and microglial expression of IDO is increased in ALS motor cortex and spinal cord (Chen et al., 2010). It has been proposed that the release of immune activating agents activates the rate-limiting enzyme of the KP, IDO, which generates metabolites such as the neurotoxin QUIN. Therefore, inhibition of IDO would reduce the synthesis of neurotoxic QUIN, which has been clearly implicated in the pathogenesis of ALS.

Huntington's Disease

Huntington's disease (HD) is a genetic autosomal dominant neurodegenerative disorder caused by expansion of the CAG repeats in the huntingtin (htt) gene. Patients affected by HD display progressive motor dysfunctions characterized by abnormality of voluntary and involuntary movements (choreoathetosis) and psychiatric and cognitive disturbances. In-life monitoring of metabolites with in the KYN pathway provide one of the few biomarkers that correlates with the number of CAG repeats and hence the severity of the disorder (Forrest et al., 2010). Post mortem very high levels of QUIN are found located in areas of neurodegeneration, while striatal glutamatergic neurones, on which QUIN acts as an excitotoxin, are a principal class lost in the disease. Importantly, TDO ablation in a *Drosophila* model of Huntington's disease ameliorated neurodegeneration (Campesan et al., 2011).

Alzheimer's Disease

Alzheimer's disease (AD) is an age-related neurodegenerative disorder characterised by neuronal loss and dementia. The histopathology of the disease is manifested by the accumulation of intracellular β-amyloid (Aβ) and subsequent formation of neuritic plaques as well as the presence of neurofibrillary tangles in specific brain regions associated with learning and memory. The pathological mechanisms underlying this disease are still controversial, however, there is growing evidence implicating KP metabolites in the development and progression of AD.

It has been shown that Aβ (1-42) can activate primary cultured microglia and induce IDO expression (Guillemin et al., 2003; Walker et al., 2006). Furthermore, IDO overexpression and increased production of QUIN have been observed in microglia associated with the amyloid plaques in the brain of AD patients (Guillemin et al., 2005). QUIN has been shown to lead to tau hyperphosphorylation in human cortical neurons (Rahman et al., 2009). Thus, overexpression of IDO and over-activation of the KP in microglia are implicated in the pathogenesis of AD.

There is also evidence for TDO involvement in Alzheimer's disease. TDO is upregulated in the brain of patients and AD mice models. Furthermore, TDO co-localizes with quinolinic acid, neurofibrillary tangles-tau and amyloid deposits in the hippocampus of AD patients (Wu et al., 2013). Therefore, the kynurenine pathway is over-activated in AD by both TDO and IDO and may be involved in neurofibrillary tangle formation and associated with senile plaque formation.

Psychiatric Disorders and Pain

Most tryptophan is processed through the kynurenine pathway. A small proportion of tryptophan is processed to 5-HT and hence to melatonin, both of which are also substrates for IDO. It has long been known that amongst other effects acute tryptophan depletion can trigger a depressive episode and produces a profound change in mood even in healthy individuals. These observations link well with the clinical benefits of serotonergic drugs both to enhance mood and stimulate neurogenesis.

The co-morbidity of depressive symptoms, implication of the kynurenine pathway in inflammation and an emerging link between TDO and the glucocorticoid mediated stress response also implicate a role in the treatment of chronic pain (Stone and Darlington 2013).

Schizophrenic patients exhibit elevated KYN levels both in CSF and brain tissue, particularly the frontal cortex. This has been associated with the "hypofrontality" observed in schizophrenia. Indeed rodents treated with neuroleptics show a marked reduction in frontal KYN levels. These changes have been associated with reduced KMO and 3HAO. Evidence includes an association between a KMO polymorphism, elevated CSF KYN and schizophrenia (Holtze etr al., 2012). Taken together there is potential for manipulations in this pathway to be both pro-cognate and neuroleptic.

Pain and depression are frequently comorbid disorders. It has been shown that IDO1 plays a key role in this comorbidity. Recent studies have shown that IDO activity is linked to (a) decreased serotonin content and depression (Dantzer et al., 2008; Sullivan et al., 1992) and (b) increased kynurenine content and neuroplastic changes through the effect of its derivatives such as quinolinic acid on glutamate receptors (Heyes et al., 1992).

In rats chronic pain induced depressive behaviour and IDO upregulation in the bilateral hippocampus. Upregulation of IDO resulted in the increased kynurenine/tryptophan ratio and decreased serotonin/tryptophan ratio in the bilateral hippocampus. Furthermore, IDO gene knockout or pharmacological inhibition of hippocampal IDO activity attenuated both nociceptive and depressive behaviour (Kim et al., 2012).

Since proinflammatory cytokines have been implicated in the pathophysiology of both pain and depression, the regulation of brain IDO by proinflammatory cytokines serves as a critical mechanistic link in the comorbid relationship between pain and depression through the regulation of tryptophan metabolism.

Multiple Sclerosis

Multiple sclerosis (MS) is an autoimmune disease characterized by inflammatory lesions in the white matter of the nervous system, consisting of a specific immune response to the myelin sheet resulting in inflammation and axonal loss (Trapp et al., 1999; Owens, 2003).

Accumulation of neurotoxic kynurenine metabolites caused by the activation of the immune system is implicated in the pathogenesis of MS. QUIN was found to be selectively elevated in the spinal cords of rats with EAE, an autoimmune animal model of MS (Flanagan et al., 1995). The origin of the increased QUIN in EAE was suggested to be the macrophages. QUIN is an initiator of lipid peroxidation and high local levels of QUIN near myelin may contribute to the demyelination in EAE and possibly MS.

Interferon beta 1b (IFN-β1b) induces KP metabolism in macrophages at concentrations comparable to those found in the sera of IFN-b treated patients, this which may be a limiting factor in its efficacy in the treatment of MS (Guillemin et al., 2001). After IFN-β administration, increased kynurenine levels and kynurenine/tryptophan ratio were found in the plasma of MS patients receiving IFN-b injection compared to healthy subjects indicating an induction of IDO by IFN-β (Amirkhani et al., 2005). IFN-β1b, leads to production of QUIN at concentrations sufficient to disturb the ability of neuronal dendrites to integrate incoming signals and kill oligodendrocytes (Cammer 2001). In IFN-β1b-treated patients concomitant blockade of the KP with an IDO/TDO inhibitor may improve its efficacy of IFN-β1b.

Parkinson's Disease

Parkinson's disease (PD) is a common neurodegenerative disorder characterised by loss of dopaminergic neurons and localized neuroinflammation.

Parkinson's disease is associated with chronic activation of microglia (Gao and Hong, 2008). Microglia activation release neurotoxic substances including reactive oxygen species (ROS) and proinflammatory cytokines such as INF-γ (Block et al., 2007), a potent activator of KP via induction of IDO expression. KP in activated microglia leads to upregulation of 3HK and QUIN. 3HK is toxic primarily as a result of conversion to ROS (Okuda et al., 1998). The combined effects of ROS and NMDA receptor-mediated excitotoxicity by QUIN contribute to the dysfunction of neurons and their death (Braidy et al., 2009; Stone and Perkins, 1981). However, picolinic acid (PIC) produced through KP activation in neurons, has the ability to protect neurons against QUIN-induced neurotoxicity, being NMDA agonist (Jhamandas et al., 1990). Microglia can become overactivated, by proinflammatory mediators and stimuli from dying neurons and cause perpetuating cycle of further microglia activation microgliosis. Excessive microgliosis will cause neurotoxicity to neighbouring neurons and resulting in neuronal death, contributing to progression of Parkinson's disease. (Zinger et al 2011): Therefore, PD is associated with an imbalance between the two main branches of the KP within the brain. KYNA synthesis by astrocytes is decreased and concomitantly, QUIN production by microglia is increased.

HIV

HIV patients, particularly those with HIV-linked dementia (Kandanearatchi & Brew 2012), often have significantly elevated KYN levels in CSF. These levels are directly related to the development of neurocognitive decline and often the presence of sever psychotic symptoms (Stone & Darlington 2013).

Cancer

It is clear that tumours can induce tolerance to their own antigens. Tryptophan catabolism in cancer is increasingly being recognized as an important micro-environmental factor that suppresses antitumor immune responses. Depletion of tryptophan and accumulation of immunosuppressive tryptophan catabolites such as kynurenine create an immunosuppressive milieu in tumours and in tumour-draining lymph nodes by inducing T-cell anergy and apoptosis. Such immunosuppression in the tumour microenvironment may help cancers evade the immune response and enhance tumorigenicity (reviewed in Adam et al., 2012).

Recently, both TDO and IDO have been implicated in tumour progression. Individually TDO or IDO have been found to be overexpressed in various cancers, furthermore, several cancers overexpress both TDO and IDO. TDO and IDO mediate immunosuppressive effects through the metabolization of Trp to kynurenine, triggering downstream signalling through GCN2, mTOR and AHR that can affect differentiation and proliferation of T cells. Also, expression of IDO by activated dendritic cells can serve to activate regulatory T cells (Tregs) and inhibit tumor-specific effector CD8+ T cells, thereby constituting a mechanism by which the immune system can restrict excessive lymphocyte reactivity (reviewed in Platten et al., 2012).

IDO

Increased expression of IDO has been shown to be an independent prognostic variable for reduced survival in patients with acute myeloid leukemia (AML), small-cell lung, melanoma, ovarian, colorectal, pancreatic, and endometrial cancers (Okamoto et al., 2005; Ino et al., 2006). Indeed, sera from cancer patients have higher kynurenine/tryptophan ratios than sera from normal volunteers (Liu et al., 2010; Weinlich et al., 2007; Huang et al., 2002). The level of IDO expression was also shown to correlate with the number of tumour infiltrating lymphocytes in colorectal carcinoma patients (Brandacher et al., 2006).

In preclinical models, transfection of immunogenic tumour cells with recombinant IDO prevented their rejection in mice (Uyttenhove et al., 2003). While, ablation of IDO expression led to a decrease in the incidence and growth of 7,12-dimethylbenz(a)anthracene-induced premalignant skin papillomas (Muller et al., 2008). Moreover, IDO inhibition slows tumour growth and restores anti-tumour immunity (Koblish et al., 2010) and IDO inhibition synergises with cytotoxic agents, vaccines and cytokines to induce potent anti-tumour activity (Uyttenhove et al., 2003; Muller et al., 2005; Zeng et al., 2009).

TDO

TDO is predominantly expressed in the liver and is believed to regulate systemic Trp concentrations, however, TDO was found to be frequently activated and constitutively expressed in glioma cells. TDO derived KYN was shown to suppress antitumor immune responses and promote tumor-cell survival and motility through the AhR in an autocrine manner (Opitz et al., 2011). It was also shown that TDO is elevated in human hepatocellular carcinomas and detected sporadically in other cancers. In a preclinical model, TDO expression prevented rejection of tumor grafts by preimmunized mice. Systemic administration of the TDO inhibitor, LM10, restored the ability of mice to reject TDO-expressing tumors (Pilotte et al., 2012).

Therefore inhibitors of TDO or IDO could have wide ranging therapeutic efficacy in the treatment of cancer. Also dual inhibitors blocking both TDO and IDO may demonstrate improved clinical efficacy by targeting both of these key Trp-metabolising enzymes and would also treat a wider patient population: in a series of 104 human tumor lines of various histological types, 20 tumors expressed only TDO, 17 expressing only IDO and 16 expressed both. Therefore, targeting both IDO and TDO would allow reaching 51% of tumors instead of 32% with IDO1 or 35% with TDO alone (Pilotte et al., 2012). Moreover, given the role of TDO in controlling systemic Trp levels, TDO inhibitors could also be used to improve the outcomes of patients with a wide variety of cancers and neoplastic diseases that do not express TDO.

Inhibition of IDO and/or TDO will dramatically lower kynurenine levels, relieving the brake on the immune system allowing it to attack and eliminate tumours. While there is evidence that a TDO/IDO inhibitor would be useful as a stand-alone agent, inhibitors of this type would be particularly effective when used in combination with other cancer immunotherapies. In fact, upregulation of IDO expression has been identified as a mechanism by which tumours gain resistance to the CTLA-4 blocking antibody ipilimumab. Ipilimumab blocks the co-stimulatory molecule CTLA-4, causing tumour-specific T cells to remain in an activated state.

IDO knockout mice treated with anti-CTLA-4 antibody demonstrate a striking delay in B16 melanoma tumor growth and increased overall survival when compared with wild-type mice. Also, CTLA-4 blockade strongly synergizes with IDO inhibitors to mediate tumour rejection. Similar data was also reported for IDO inhibitors in combination with anti-PD1 and anti-PDL-1 antibodies (Holmgaard et al., 2013).

Agents that will influence an immunosuppressive environment may also be relevant to chimeric antigen receptor T cell therapy (CAR-T) therapies to enhance efficacy and patient responses.

Other Diseases

Although these effects are defensive strategies to cope with infection and inflammation, they may have unintended consequences because kynurenines formed during IDO and TDO-mediated degradation of tryptophan can chemically modify proteins and have been shown to be cytotoxic (Morita et al., 2001; Okuda et al., 1998). In coronary heart disease, inflammation and immune activation are associated with increased blood levels of kynurenine (Wirleitner et al., 2003) possibly via interferon-γ-mediated activation of IDO. In experimental chronic renal failure, activation of IDO leads to increased blood levels of kynurenines (Tankiewicz et al., 2003), and in uremic patients kynurenine-modified proteins are present in urine (Sala et al., 2004). Further, renal IDO expression may be deleterious during inflammation, because it enhances tubular cell injury.

General anaesthesia unfortunately mimics many of these effects inducing stress and inflammatory processes. Post anaesthesia cognitive dysfunction has often been correlated with these sequelae. Recently these deficits have been shown to be correlated with changes in kynurenine pathway markers, but not cytokines, following cardiac surgery and in recovering stroke patients (Stone and Darlington 2013).

Cataracts

A cataract is a clouding of the lens inside the eye that leads to a decrease in vision. Recent studies suggest that kynurenines might chemically alter protein structure in the human lens leading to cataract formation. In the human lens IDO activity is present mainly in the anterior epithelium (Takikawa et al., 1999). Several kynurenines, such as kynurenine (KYN), 3-hydroxykynurenine (3OHKYN), and 3-hydroxykynurenine glucoside (3OHKG) have been detected in the lens; where they were thought to protect the retina by absorbing UV light and therefore are commonly referred to as UV filters. However, several recent studies show that kynurenines are prone to deamination and oxidation to form α,β-unsaturated ketones that chemically react and modify lens proteins (Taylor et al., 2002). Kynurenine mediated modification could contribute to the lens protein modifications during aging and cataractogenesis. They may also reduce the chaperone function of α-crystallin, which is necessary for maintaining lens transparency.

Transgenic mouse lines that overexpress human IDO in the lens developed bilateral cataracts within 3 months of birth. It was demonstrated that IDO-mediated production of kynurenines results in defects in fibre cell differentiation and their apoptosis (Mailankot et al., 2009). Therefore inhibition of IDO may slow the progression of cataract formation.

Female Reproductive Health

Endometriosis

Endometriosis, the presence of endometrium outside the uterine cavity, is a common gynaecological disorder, causing abdominal pain, dyspareunia and infertility. IDO expression was found to be higher in eutopic endometrium from women with endometriosis by microarray analysis (Burney et al., 2007 and Aghajanova et al., 2011). Furthermore, IDO was shown to enhance the survival and invasiveness of endometrial stromal cells (Mei et al., 2013). Therefore, an IDO/TDO inhibitor could be used as a treatment for endometriosis.

Contraception and Abortion

The process of implantation of an embryo requires mechanisms that prevent allograft rejection; and tolerance to the fetal allograft represents an important mechanism for maintaining a pregnancy. Cells expressing IDO in the foeto-maternal interface protect the allogeneic foetus from lethal rejection by maternal immune responses. Inhibition of IDO by exposure of pregnant mice to 1-methyl-tryptophan induced a T cell-mediated rejection of allogeneic concepti, whereas syngeneic concepti were not affected; this suggests that IDO expression at the foetal-maternal interface is necessary to prevent rejection of the foetal allograft (Munn et al., 1998). Accumulating evidence indicates that IDO production and normal function at the foetal-maternal interface may play a prominent role in pregnancy tolerance (Durr and Kindler, 2013). Therefore, an IDO/TDO inhibitor could be used as a contraceptive or abortive agent.

On the above basis, the inventors have determined that a strong rationale exists for the therapeutic utility of drugs which block the activity of TDO and/or IDO, in treating the above-mentioned diseases, conditions and disorders.

Having regard to the above, it is an aim of the present invention to provide TDO or IDO inhibitors, and in particular TDO and IDO inhibitors for use in medicine. It is a further aim to provide pharmaceutical compositions comprising such inhibitors, and in particular to provide compounds and pharmaceutical compositions for treating a cancer, an inflammatory condition, an infectious disease, a central nervous system disease or disorder and other diseases, conditions and disorders. It is also an aim to provide methods of synthesis of the compounds.

WO 2012/084971 discloses compounds which are similar to those presently envisaged, but which do not have an atom double-bonded to an oxygen atom unlike in substituent $R^6$ in the present compounds. These compounds are disclosed as being direct antibacterial agents. IDO and TDO inhibition is not mentioned, and there is no disclosure that the compounds have TDO or IDO inhibitory activity, or a pharmacology associated with a TDO or IDO mechanism.

WO 94/19321 and WO 2014/009794 each disclose compounds for treating HIV. Some of the compounds are similar to those presently envisaged, but in WO 94/19321 are indicated to be direct reverse transcriptase inhibitors, whilst in WO 2014/009794 are indicated to be direct anti-virals. IDO and TDO inhibition is not mentioned, and there is no disclosure that the compounds have TDO or IDO inhibitory activity, or a pharmacology associated with a TDO or IDO mechanism.

WO 2008/002674 and WO 03/035621 disclose protein kinase and phosphatase inhibitors, which may be employed inter alia in the treatment of cancer. Some such compounds are similar to those investigated by the present inventors, but IDO and TDO inhibition is not mentioned, and there is no disclosure that the compounds have TDO or IDO inhibitory activity, or a pharmacology associated with a TDO or IDO mechanism, i.e. the ablation of tryptophan depletion/kynurenine production, with the associated increase in T-cell proliferation and tumour immune response.

Previously, Dolusic et al. have tested indole compounds to determine their IDO inhibitory activity (European Journal of Medicinal Chemistry 46 (2011) 3058-3065; Bioorganic and Medicinal Chemistry, Vol. 19(4), 2011, pp 1550-1561). That study determined that certain indole compounds with ketone substituents at the 2-position might be useful IDO inhibitors. However, the activity of such compounds was found to be marginal at best. It was concluded that an amide compound of the type the inventors have investigated was not an effective inhibitor as compared with the ketone compounds. However, the inventors have now determined that Dolusic et al. were mistaken about such amide compounds in that certain carbonyl compounds with adjacent hetero atoms are highly active.

Accordingly, the present invention provides a tryptophan-2,3-dioxygenase (TDO) and/or indoleamine-2,3-dioxygenase (IDO) inhibitor compound for use in medicine, which compound comprises the following formula:

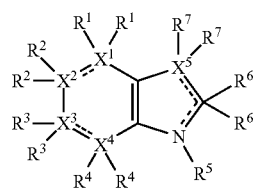

wherein $X^1$, $X^2$, $X^3$, $X^4$, and $X^5$ may be the same or different and each is independently selected from C, N and O; each atom having a dotted line may independently have a double bond or a single bond, provided that valencies at each atom are maintained; each $R^1$, $R^2$, $R^3$, $R^4$, $R^5$, and $R^7$ may be present or absent and may be the same or different and is selected from H and a substituted or unsubstituted organic group, provided that the number of such R groups present is such that the valencies of $X^1$, $X^2$, $X^3$, $X^4$, and $X^5$ are maintained; one or two $R^6$ groups may be present and are selected from H and a substituted or unsubstituted organic group, provided that the number of $R^6$ groups present is such that the valency of the carbon atom to which they are attached is maintained, and provided that at least one $R^6$ is an organic group comprising an atom double-bonded to an oxygen atom (preferably a carbonyl group or a sulphonyl group) at an α-, β- or γ-position to the carbon atom to which the $R^6$ is attached and in which the atom double-bonded to an oxygen atom is also bonded to a hetero-atom.

In the present context the dotted line between two atoms indicates the possible presence of a further bond. In a case where two atoms are already joined by a solid line, but also have a dotted line, then those atoms have at least a single bond, but possibly a double bond in some cases. Thus, in such cases, each atom having a dotted line may independently have a double bond or a single bond, provided that valencies at each atom are maintained. In cases where there is only a dotted line joining two atoms, then these atoms may not be directly bonded at all in some cases, or in other cases may be joined by a single bond.

In the formulae herein, all tautomeric forms of the ring system (including the tautomeric forms of the 6-membered ring and the tautomeric forms of the 5-membered ring are intended to be included.

In the present context, a heteroatom is an atom which is not a carbon atom. In typical embodiments, the heteroatom is selected from N, O, S, P, B or Si, or more typically is selected from N, O and S.

Thus, the compounds may have one of the following formulae:

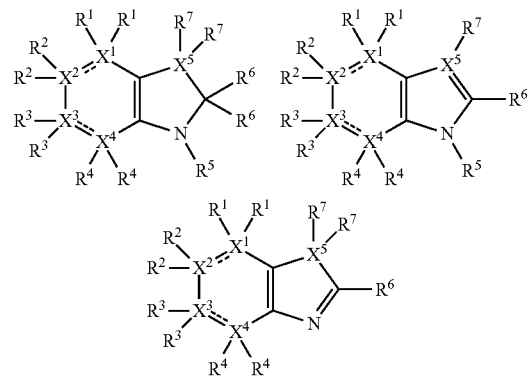

In some more preferred embodiments $X^5$ is C, in which case the compounds have one of the following formulae:

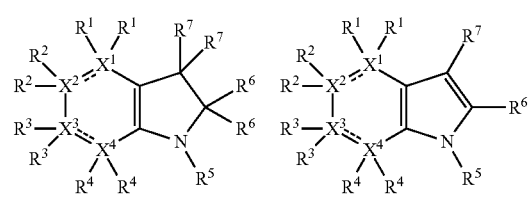

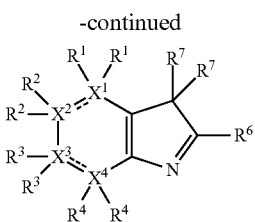

In other embodiments $X^5$ is N, in which case the compounds have one of the following formulae:

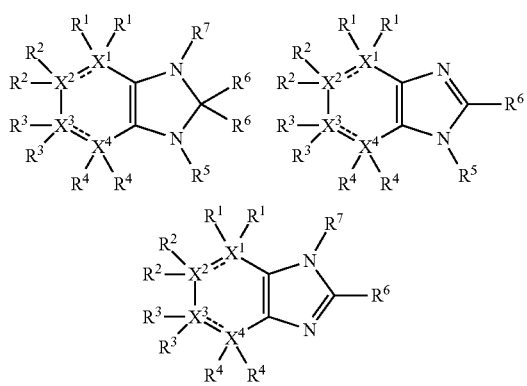

In other embodiments, $X^5$ is O, in which case the compounds have one of the following formulae:

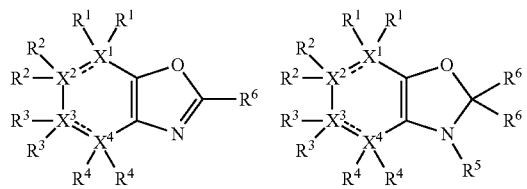

In the present compounds it is typical that the $X^1$, $X^2$, $X^3$, and/or $X^4$ groups are C, in which case the compounds have one of the following formulae:

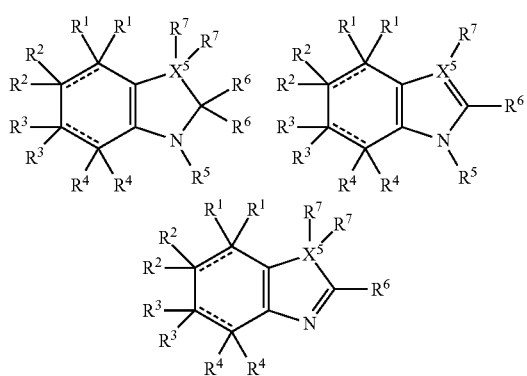

In these formulae, $X^5$ may be C, N or O (preferably C) as mentioned above, such that the compounds have the following formulae:

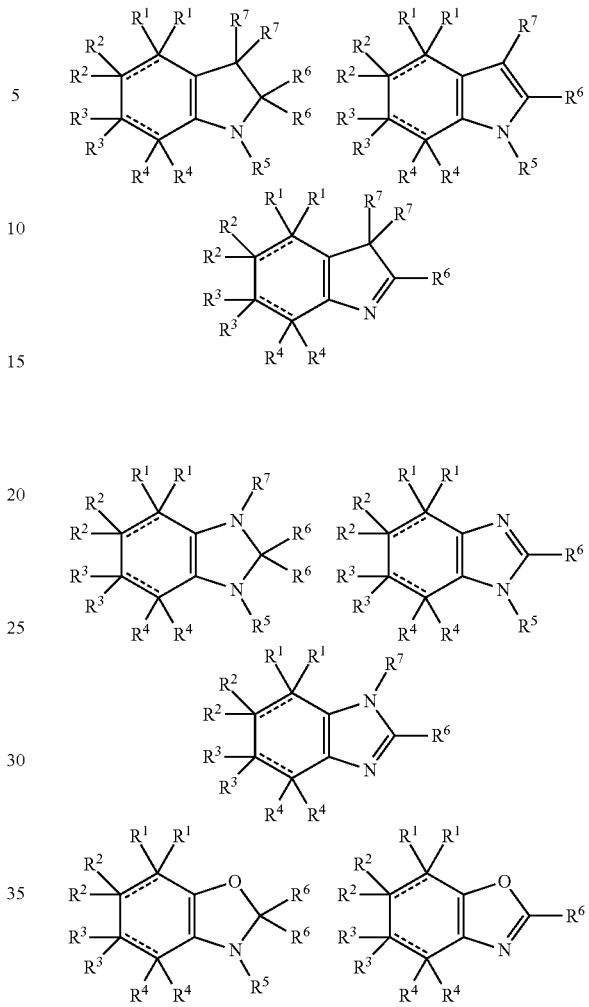

In certain of the embodiments represented by all of the structures above, when present $R^1$ and $R^4$ are both H, or $R^1$ and $R^4$ are both not H, or $R^1$ is not H and $R^4$ is H, or $R^4$ is not H and $R^1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H.

In the context of the present invention, maintaining the valency means ensuring that an atom has its normal (typically most common) valency in organic compounds (i.e. 2 for oxygen, 3 for nitrogen and 4 for carbon). Nitrogen atoms may, in some instances, have 4 bonds, but in such cases they are typically positively charged such that the compound may have a counter-ion. Such compounds are also part of the invention, and in these cases, due to the positive charge, it will be clear that the nitrogen atom still maintains its normal valency of 3. For the avoidance of doubt, where the number of R groups may vary according to the choice of X group, it may vary as follows.

Each $R^1$ may be the same or different, provided that: $R^1$ is absent when $X^1$ is O; $R^1$ is absent when $X^1$ is N and is double bonded to a ring atom; one $R^1$ is present when $X^1$ is N and is not double bonded to a ring atom; one $R^1$ is present when $X^1$ is C and is double bonded to a ring atom; and two $R^1$ are present when $X^1$ is C and is not double bonded to a ring atom. Preferably $R^1$ (or both $R^1$ if there are two such groups) is H.

Each $R^2$ may be the same or different, provided that: $R^2$ is absent when $X^2$ is O; $R^2$ is absent when $X^2$ is N and is double bonded to a ring atom; one $R^2$ is present when $X^2$ is N and is not double bonded to a ring atom; one $R^2$ is present when $X^2$ is C and is double bonded to a ring atom; and two $R^2$ are present when $X^2$ is C and is not double bonded to a ring atom. Each $R^3$ may be the same or different, provided that: $R^3$ is absent when $X^3$ is O; $R^3$ is absent when $X^3$ is N and is double bonded to a ring atom; one $R^3$ is present when $X^3$ is N and is not double bonded to a ring atom; one $R^3$ is present when $X^3$ is C and is double bonded to a ring atom; and two $R^3$ are present when $X^3$ is C and is not double bonded to a ring atom. Preferably one of $R^2$ and $R^3$ (or, if appropriate one of the two $R^2$s or one of the two $R^3$s) is not H.

Each $R^4$ may be the same or different, provided that: $R^4$ is absent when $X^4$ is O; $R^4$ is absent when $X^4$ is N and is double bonded to a ring atom; one $R^4$ is present when $X^4$ is N and is not double bonded to a ring atom; one $R^4$ is present when $X^4$ is C and is double bonded to a ring atom; and two $R^4$ are present when $X^4$ is C and is not double bonded to a ring atom. Preferably $R^4$ (or both $R^4$ if there are two such groups) is H.

Each $R^6$ may be the same or different, provided that two $R^6$ are present when the carbon to which they are attached is not double bonded to a ring atom, and one $R^6$ is present when the carbon to which it is attached is double bonded to a ring atom. If there are two $R^6$ groups, one may be H or an organic group, whilst the other is the organic group comprising an atom double-bonded to an oxygen atom at an α-, β-, or γ-position to the carbon atom to which the $R^6$ is attached, as defined above. When there are two $R^6$ groups, preferably one of them is H. In all of the embodiments herein, at least one $R^6$ comprises an organic group comprising an atom double-bonded to an oxygen atom (preferably forming a carbonyl group or a sulphonyl group) at an α-, β-, or γ-position to the carbon atom to which the $R^6$ is attached. In this context, the teens α-, β-, or γ-position have the common meaning in organic chemistry, that is to say that they refer to the adjacent atom (α-), or the next-but-one atom (β-), or the next-but-two atom (γ-). Thus, the atom double-bonded to the oxygen atom may be the atom adjacent to the ring carbon to which $R^6$ is attached, or may be the next-but-one atom to the ring carbon to which $R^6$ is attached, or may be the next-but-two atom to the ring carbon to which $R^6$ is attached. For the purposes of clarity, the α-, β-, and γ-positions are illustrated below:

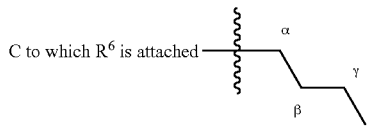

The atom double-bonded to an oxygen atom may be any atom common to organic groups (except oxygen and halogen), such as C, S, or P. As has been mentioned, preferably the atom double bonded to the oxygen forms a carbonyl group or a sulphonyl group. In the compounds of the invention, the atom double-bonded to an oxygen atom (or the carbonyl group or sulphonyl group as the case may be) is further attached to an adjacent heteroatom. The adjacent heteroatom in this case may be any heteroatom common to organic groups (i.e. any non-carbon atom common to organic groups) and is typically an atom selected from N, O, S, P, B or Si, although in more preferred embodiments it is N.

Each $R^7$ may be the same or different, provided that: $R^7$ is absent when $X^5$ is O; $R^7$ is absent when $X^5$ is N and is double bonded to a ring atom; one $R^7$ is present when $X^5$ is N and is not double bonded to a ring atom; one $R^7$ is present when $X^5$ is C and is double bonded to a ring atom, and two $R^7$ are present when $X^5$ is C and is not double bonded to a ring atom. Preferably $R^7$ (or both $R^7$ if there are two such groups) is H.

In these compounds, and elsewhere herein, in some embodiments any R group may form a ring with any other R group on an adjacent and/or proximal atom, although in most embodiments this is not preferred. Thus, in some embodiments the following substituents may together form a ring: $R^1$ and $R^2$, $R^1$ and $R^7$, $R^2$ and $R^3$, $R^3$ and $R^4$, $R^4$ and $R^5$, $R^5$ and $R^6$, and/or $R^6$ and $R^7$. In the context of the present invention, an adjacent and/or proximal atom may mean another atom directly bonded to an atom (adjacent), or may be two atoms with only a single atom in between (proximal), or may mean two atoms close enough sterically to be capable of Raining a ring (proximal). Accordingly the definition includes $R^1$ and $R^7$. Preferably R groups attached to the same atom do not together form a ring, although this is not excluded. Preferably $R^5$ and $R^7$ do not form a ring with another R group, and typically $R^5$ is a substituted or unsubstituted lower ($C_1$-$C_6$) alkyl group, more typically H or Me.

In any compound where there are two R groups attached to the same atom, the invention includes compounds in which two R groups (except in the case of $R^5$ and $R^6$) together form a group which is double bonded to that atom. Accordingly, two R groups attached to the same atom may together form a =O group, or a =C(R')$_2$ group (wherein each R' group is the same or different and is H or an organic group, preferably H or a straight or branched $C_1$-$C_6$ alkyl group). This is more typical in cases where the R groups are attached to a C atom, such that together they form a C=O group or a C=C(R')$_2$ group. $R^1$, $R^2$, $R^3$, $R^4$ and $R^7$ may thus typically be =O groups, as may $R^{63}$, $R^{64}$ and $R^{66}$ in structures discussed below.

In the context of the present invention, a compound is considered to be a TDO inhibitor if its presence is capable of preventing, reducing or slowing the conversion of tryptophan into N-formylkynurenine by TDO as compared to the same conversion in its absence. Similarly, in the context of the present invention, a compound is considered to be an IDO inhibitor if its presence is capable of preventing, reducing or slowing the conversion of tryptophan into N-formylkynurenine by IDO as compared to the same conversion in its absence. Preferably, a compound is considered to be a TDO inhibitor if its inhibitory activity is sufficiently high to score a '+' in the A172 human glioblastoma cell-based assay as set out in the examples. Preferably a compound is considered to be a IDO inhibitor if its inhibitory activity is sufficiently high to score a '+' in the SKOV-3 ovary adenocarcinoma cell-based assay as set out in the examples. The compounds of the invention may be selective TDO inhibitors, or selective IDO inhibitors, or may be inhibitors of both IDO and TDO.

In all of the embodiments of this invention (both above and below herein), unless otherwise specified, a substituent (such as any R group, X group, or any other substituent) is not especially limited, provided that it does not prevent the TDO or IDO inhibitory function from occurring. In all of the embodiments mentioned in connection with this invention, both above and in the following, unless otherwise specified, the substituents are selected from H and an organic group. Thus, both above and in the following, the terms 'substituent' and 'organic group' are not especially limited and may be any functional group or any atom, especially any functional group or atom common in organic chemistry. Thus, 'substituent' and 'organic group' may have any of the following meanings.

The substituent or organic group may comprise any organic group and/or one or more atoms from any of groups IIIA, IVA, VA, VIA or VIIA of the Periodic Table, such as a B, Si, N, P, O, or S atom (e.g. OH, OR, $NH_2$, NHR, $NR_2$, SH, SR, $SO_2R$, $SO_3H$, $PO_4H_2$) or a halogen atom (e.g. F, Cl, Br or I) where R is a substituted or unsubstituted linear or branched lower hydrocarbon (1-6 C atoms) or a substituted or unsubstituted linear or branched higher hydrocarbon (7 C atoms or more, e.g. 7-40 C atoms).

When the substituent comprises an organic group, the organic group preferably comprises a hydrocarbon group. The hydrocarbon group may comprise a straight chain, a branched chain, or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups.

When the hydrocarbon comprises a cyclic group it may comprise an aromatic ring, a non-aromatic ring, an aliphatic ring, a heterocyclic group, and/or fused ring derivatives of these groups. The ring may be fully saturated, partially saturated, or fully unsaturated. The cyclic group may thus comprise a benzene, naphthalene, anthracene, phenanthrene, phenalene, biphenylene, pentalene, indene, as-indacene, s-indacene, acenaphthylene, fluorene, fluoranthene, acephenanthrylene, azulene, heptalene, pyrrole, pyrazole, imidazole, 1,2,3-triazole, 1,2,4-triazole, tetrazole, pyrrolidine, furan, tetrahydrofuran, 2-aza-tetrahydrofuran, 3-aza-tetrahydrofuran, oxazole, isoxazole, furazan, 1,2,4-oxadiazol, 1,3,4-oxadiazole, thiophene, isothiazole, thiazole, thiolane, pyridine, pyridazine, pyrimidine, pyrazine, piperidine, 2-azapiperidine, 3-azapiperidine, piperazine, pyran, tetrahydropyran, 2-azapyran, 3-azapyran, 4-azapyran, 2-aza-tetrahydropyran, 3-aza-tetrahydropyran, morpholine, thiopyran, 2-azathiopyran, 3-azathiopyran, 4-azathiopyran, thiane, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene, as well as regioisomers of the above groups. These groups may generally be attached at any point in the group, and also may be attached at a hetero-atom or at a carbon atom. In some instances particular attachment points are preferred, such as at 1-yl, 2-yl and the like, and these are specified explicitly where appropriate. All tautomeric ring forms are included in these definitions. For example pyrrole is intended to include 1H-pyrrole, 2H-pyrrole and 3H-pyrrole.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The lower hydrocarbon group may be a methyl, ethyl, propyl, butyl, pentyl or hexyl group or regioisomers of these, such as isopropyl, isobutyl, tert-butyl, etc. The number of atoms in the ring of the cyclic group is not especially limited, but preferably the ring of the cyclic group comprises from 3-10 atoms, such as 3, 4, 5, 6, 7, 8, 9 or 10 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, sulphonyl groups, and phosphate groups etc. The substituent may also comprise derivatives of these groups, such as carboxylic acid anhydrides and carboxylic acid halides.

In addition, any substituent may comprise a combination of two or more of the substituents and/or functional groups defined above.

The invention will now be explained in more detail, by way of example only, with reference to the following Figures.

FIG. 1 shows a schematic diagram of tryptophan catabolism along the KP (from "The Kynurenine Pathway in Brain Tumour Pathogenesis", Adam et al., 2012, Cancer Res 72:5649-57).

Figure 2:
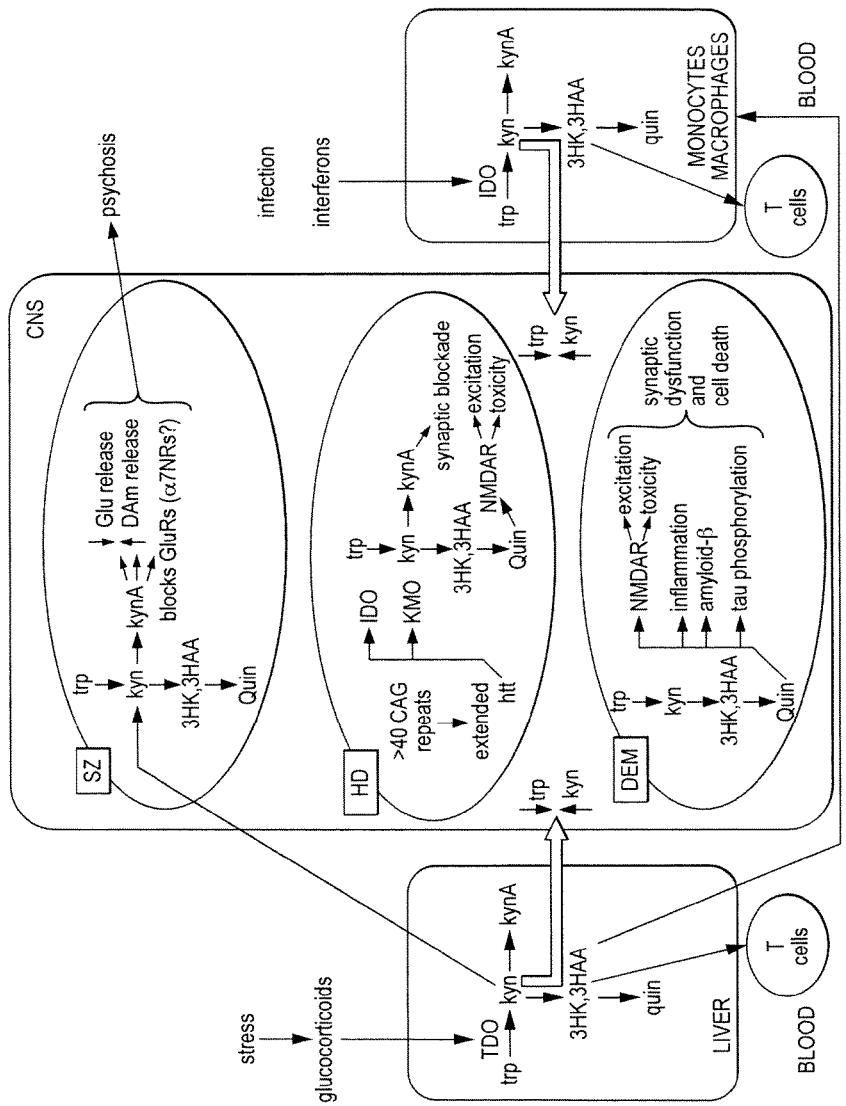

FIG. 2 shows a schematic summary of the involvement of kynurenine in CNS disorders (from "The kynurenine pathway as a therapeutic target in cognitive and neurodegenerative disorders", Stone and Darlington. Br. J. Pharmacol. 2013 169(6):1211-27.

The compounds used in the invention will now be described in more detail.

As has been described, the invention relates to a tryptophan-2,3-dioxygenase (TDO) and/or indoleamine-2,3-dioxygenase (IDO) inhibitor compound for use in medicine, which compound comprises the following formula:

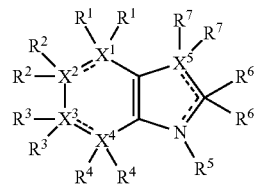

wherein $X^1$, $X^2$, $X^3$, $X^4$, and $X^5$ may be the same or different and each is independently selected from C, N, and O; each atom having a dotted line may independently have a double bond or a single bond, provided that valencies at each atom are maintained; each $R^1$, $R^2$, $R^3$, $R^4$, $R^5$, and $R^7$ may be present or absent and may be the same or different and is selected from H and a substituted or unsubstituted organic group, provided that the number of such R groups present is such that the valencies of $X^1$, $X^2$, $X^3$, $X^4$, and $X^5$ are maintained; one or two $R^6$ groups may be present and are selected from H and a substituted or unsubstituted organic group, provided that the number of $R^6$ groups present is such that the valency of the carbon atom to which they are attached is maintained, and provided that at least one $R^6$ is an organic group comprising an atom double-bonded to an oxygen atom (preferably forming a carbonyl group or a sulphonyl group) at an $\alpha$-, $\beta$-, or $\gamma$-position to the carbon atom to which the $R^6$ is attached and in which the atom double-bonded to an oxygen atom is also bonded to a hetero-atom.

All tautomeric forms of the ring system (including the tautomeric forms of the 6-membered ring and the tautomeric forms of the 5-membered ring, and all combinations thereof), are included.

As has been mentioned, this definition includes compounds in which, where there are two R groups attached to the same atom, except for $R^5$ and $R^6$, they may together form a group which is double bonded to that atom, such as a carbonyl group (=O) or an alkene group (=C(R')$_2$) (wherein each R' group is the same or different and is H or an organic group, preferably H or a straight or branched $C_1$-$C_6$ alkyl group). Accordingly, in some embodiments $R^1$, $R^2$, $R^3$, $R^4$, and/or $R^7$ may be a =O group, as may $R^{63}$, $R^{64}$ and/or $R^{66}$ in some embodiments discussed below.

As has been mentioned, previously, Dolusic et al. have tested indole compounds to determine their IDO inhibitory activity and that study determined that certain indole compounds with ketone substituents at the 2-position might be useful IDO inhibitors, although marginally. Dolusic et al. concluded that a similar amide compound was not an effective inhibitor as compared with the ketone compounds. However, the inventors have now determined that Dolusic et al. were mistaken about amide compounds in that certain carbonyl compounds with adjacent hetero atoms are highly active. The amide compound in the Dolusic paper (compound REF) is not active and is therefore not claimed by the present invention, which only extends to active compounds. It has however been used as a reference compound in testing compounds of the invention.

In the present context, preferably $R^5$ and $R^7$ do not comprise a cyclic group. Typically $R^5$ and $R^7$ are selected from H and a substituted or unsubstituted, linear or branched, $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl). More preferably both of $R^5$ and $R^7$ are H, or one of $R^5$ and $R^7$ is H and the other is Me (e.g. $R^5$=H and $R^7$=Me, or $R^5$=Me and $R^7$=H), or both of $R^5$ and $R^7$ are Me.

In the above formula, in certain embodiments, when present $R^1$ and $R^4$ are both H, or $R^1$ and $R^4$ are both not H, or $R^1$ is not H and $R^4$ is H, or $R^4$ is not H and $R^1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H.

It follows from the formula that $X^1$, $X^2$, $X^3$ and $X^4$ form a ring together with two C atoms, and all are present such that the ring is a 6-membered ring. This ring has at least one unsaturated bond between the two adjacent C atoms bridging the ring system, but may also have two or three unsaturated bonds, depending upon the bonding between the X atoms. $X^1$, $X^2$, $X^3$ and $X^4$ are selected from C, N and O. Typically all of $X^1$, $X^2$, $X^3$ and $X^4$ are C, but alternatively three of $X^1$, $X^2$, $X^3$ and $X^4$ may be C, two of $X^1$, $X^2$, $X^3$ and $X^4$ may be C, one of $X^1$, $X^2$, $X^3$ and $X^4$, may be C or all of $X^1$, $X^2$, $X^3$ and $X^4$ may be N. In some embodiments one of $X^1$, $X^2$, $X^3$ and $X^4$, may be N or two of $X^1$, $X^2$, $X^3$ and $X^4$, may be N. In some embodiments one of $X^1$, $X^2$, $X^3$ and $X^4$, may be O or two of $X^1$, $X^2$, $X^3$ and $X^4$, may be O.

$X^5$ forms a 5-membered ring together with one N atom and three C atoms. The ring has at least one unsaturated bond between the two adjacent C atoms bridging the ring system, but may also have a further unsaturated bond depending upon the bonding at $X^5$, and depending upon the bonding at the N atom. Thus, in some embodiments there may be a double bond between $X^5$ and the carbon atom bearing $R^6$, whilst in other embodiments there may be a double bond between the N atom and the carbon atom bearing $R^6$. In still further embodiments, the only double bond in the 5-membered ring is the one between the two adjacent C atoms bridging the ring system. Typically $X^5$ is a C atom, and typically it is double-bonded to the adjacent C-atom. However, in certain embodiments, $X^5$ is C and is single bonded to the adjacent C atom, or $X^5$ is N and is double-bonded to the adjacent C atom, or $X^5$ is N and is single bonded to the adjacent C atom, or $X^5$ is O and is single bonded to the adjacent C atom.

Thus, in view of the typical embodiments already described, in certain embodiments the invention relates to a compound as defined above, which compound comprises one of the following formulae:

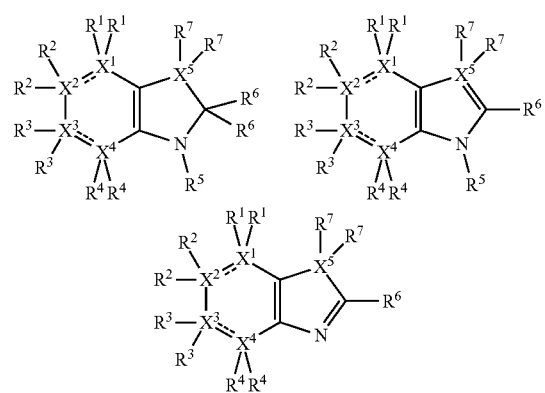

In some more preferred embodiments $X^5$ is C, in which case the compounds have one of the following formulae:

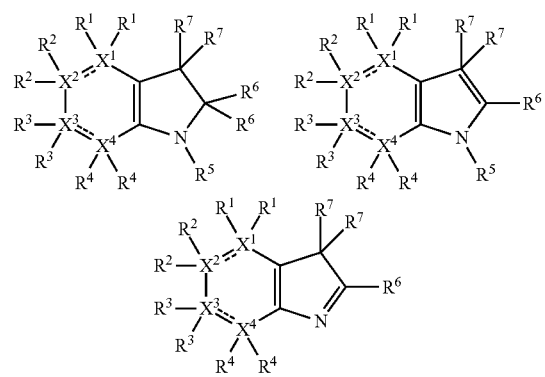

In other embodiments $X^5$ is N, in which case the compounds have one of the following formulae:

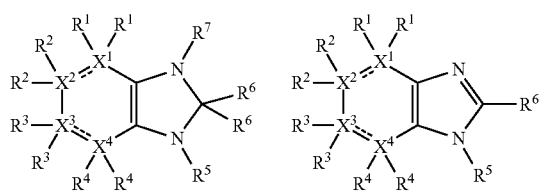

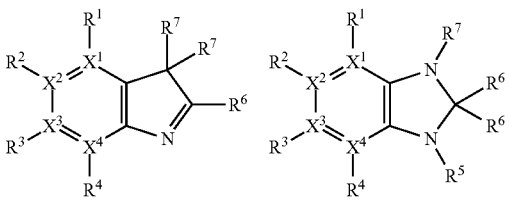

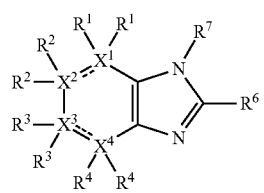

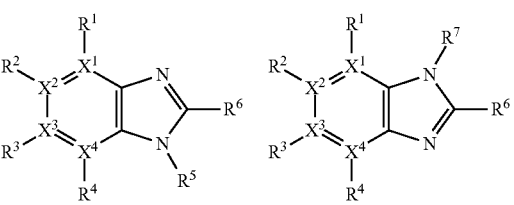

In other embodiments, $X^5$ is O, in which case the compounds have one of the following formulae:

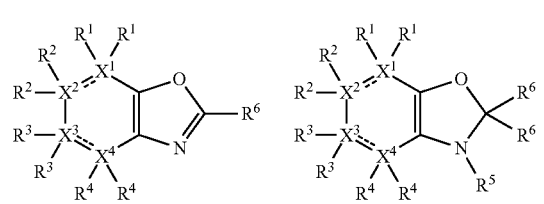

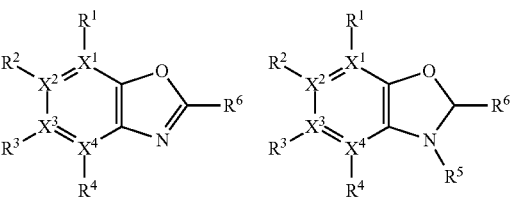

In further preferred embodiments, the six membered ring is fully unsaturated such that the compounds have one of the following formulae:

In still further preferred embodiments, in any of the above formulae, the five-membered ring has at least one double bond, and/or the 6-membered ring is fully unsaturated, and/or all of $X^1$, $X^2$, $X^3$, and $X^4$ are C or one of $X^1$, $X^2$, $X^3$, and $X^4$ is N.

More preferred compounds of this type include the following:

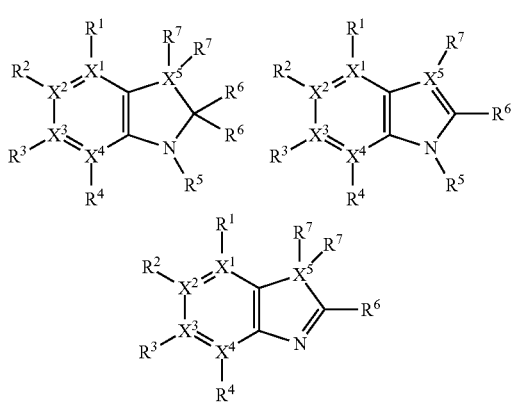

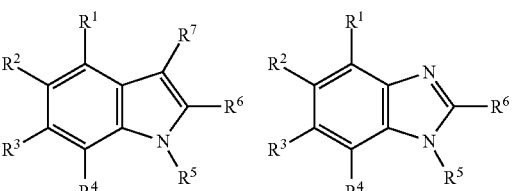

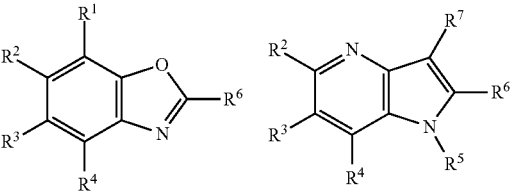

and when $X^5$ is C, N or O the following formulae:

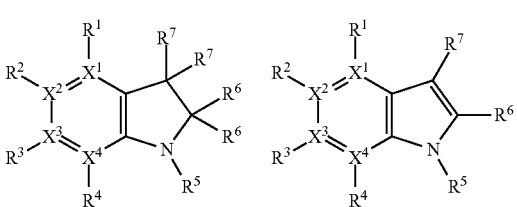

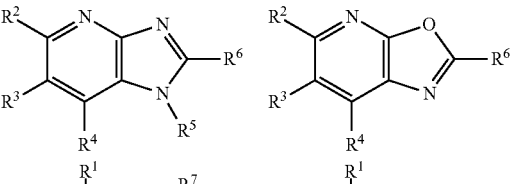

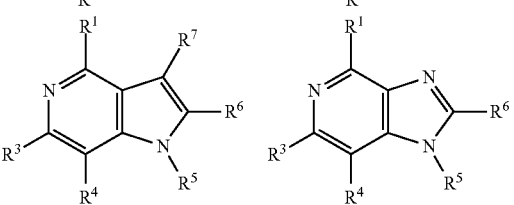

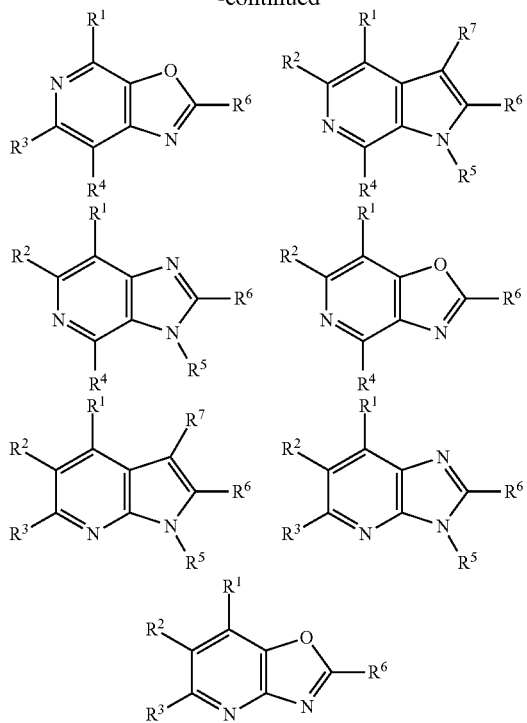

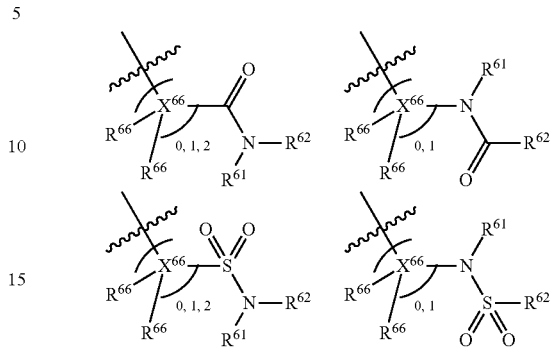

wherein $R^{61}$ is selected from H and a substituted or unsubstituted organic group; $R^{62}$ is selected from H and a substituted or unsubstituted organic group; $X^{66}$ is selected from C, O, N and S ($X^{66}$ is preferably C and if more than one $X^{66}$ is present, preferably at least one $X^{66}$ is C); and if present each $R^{66}$ may be the same or different and is selected from H and a substituted or unsubstituted organic group, wherein the number of $R^{66}$ present is sufficient to maintain the valency of $X^{66}$, in the manner already explained above. The number of $X^{66}$ atoms present may determine whether the atom double-bonded to the oxygen atom is α-, β-, or γ- to the ring system, and may be selected accordingly. When there are two $X^{66}$ atoms present they may be joined by a double bond or a single bond.

In the present context, and in general herein, the part of the structure present in brackets may be repeated the number of times given by the numbers next to the brackets. For example, in the case of $(X^{66}(R^{66})_2)_{0,1,2}$ the $X^{66}(R^{66})_2$ group may be absent, or may be present once: $-X^{66}(R^{66})_2-$; or may be present twice: $-X^{66}(R^{66})_2-X^{66}(R^{66})_2-$; or $-X^{66}(R^{66})=X^{66}(R^{66})-$.

In typical embodiments $R^{62}$ comprises a group having the following formula:

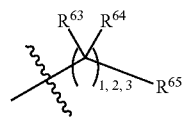

wherein $R^{63}$ and $R^{64}$ may be the same or different and are independently selected from H and a substituted or unsubstituted organic group, and wherein $R^{65}$ is selected from H and a substituted or unsubstituted organic group. Thus there may be one $-C(R^{63}R^{64})-$ group, or two such groups or three such groups present between the bicyclic ring system and the $R^{65}$ group. When there is one $-C(R^{63}R^{64})-$ group (most preferred), typically at least one of $R^{63}$ and $R^{64}$ is not H. More typically $R^{63}$ and $R^{64}$ together form a 3-6 membered substituted or unsubstituted saturated or unsaturated carbocyclic or heterocyclic ring (such as a cyclopropyl, cyclobutyl, cyclopentyl, cyclopentenyl, cyclohexyl, cyclohexenyl, aziridine, azetidine, pyrrolidine, piperidine, piperazine, oxetane, tetrahydrofuran or tetrahydropyran ring).

When there is more than one $-C(R^{63}R^{64})-$ group typically at least one of any of the $R^{63}$ and $R^{64}$ groups present is not H. More typically at least one $R^{63}$ and $R^{64}$ In these compounds, in certain embodiments, when present $R^1$ and $R^4$ are both H, or $R^1$ and $R^4$ are both not H, or $R^1$ is not H and $R^4$ is H, or $R^4$ is not H and $R^1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H.

In all of the embodiments herein, as has been described, $R^6$ comprises an organic group comprising an atom double-bonded to an oxygen atom (preferably forming a carbonyl group or a sulphonyl group) at an α-, β-, or γ-position to the carbon atom to which the $R^6$ is attached. In this context, the terms α-, β-, and γ-position have the common meaning in organic chemistry, that is to say that they refer to the adjacent atom (α-) or the next-but-one atom (β-), or the next-but-two atom (γ-). Thus, atom double-bonded to an oxygen atom may be an atom adjacent to the ring carbon to which $R^6$ is attached, or may be the next-but-one atom to the ring carbon to which $R^6$ is attached, or may be the next-but-two atom to the ring carbon to which $R^6$ is attached. The atom double-bonded to an oxygen atom may be any atom common to organic groups (except oxygen and halogen), such as C, S, or P. As has been mentioned, preferably the atom double bonded to the oxygen forms a carbonyl group or a sulphonyl group. In the present compounds, the atom double-bonded to an oxygen atom (or the carbonyl group or sulphonyl group as the case may be) is further attached to an adjacent heteroatom. The adjacent heteroatom in this case may be any heteroatom common to organic groups (i.e. any non-carbon atom common to organic groups) and is typically an atom selected from N, O, S, P, B or Si, although in more preferred embodiments it is N.

The carbonyl group or sulphonyl group may be any carbonyl group or sulphonyl group as long as it is a carbonyl group or a sulphonyl group attached to an adjacent heteroatogether form a 3-6 membered substituted or unsubstituted saturated or unsaturated carbocyclic or heterocyclic ring (such as a cyclopropyl, cyclobutyl, cyclopentyl, cyclopentenyl, cyclohexyl, cyclohexenyl, aziridine, azetidine, pyrrolidine, piperidine, piperazine, oxetane, tetrahydrofuran or tetrahydropyran ring). In these compounds the $R^{63}$ or $R^{64}$ group that is not H, or the 3-6 membered substituted or unsubstituted saturated or unsaturated carbocyclic or heterocyclic ring, may be on any of the —C($R^{63}R^{64}$)— groups, including the central one, but is preferably on the —C($R^{63}R^{64}$)— group closest to the bicyclic ring system, or on the —C($R^{63}R^{64}$)— group next to the $R^{65}$ group. When there are two or more $R^{63}$ groups, or two or more $R^{64}$ groups, each $R^{63}$ may be the same or different and each $R^{64}$ may be the same or different. In some embodiments $R^{63}$ and $R^{64}$ may together form a group which is double bonded to the carbon atom to which they are attached (such as a carbonyl group (=O) or an alkene group (=C(R')$_2$) wherein each R' group is the same or different and is H or an organic group, preferably H or a straight or branched $C_1$-$C_6$ alkyl group).

Thus, in view of the typical embodiments already described, in certain embodiments the invention relates to a compound as defined above, which compound comprises one or other of the following formulae:

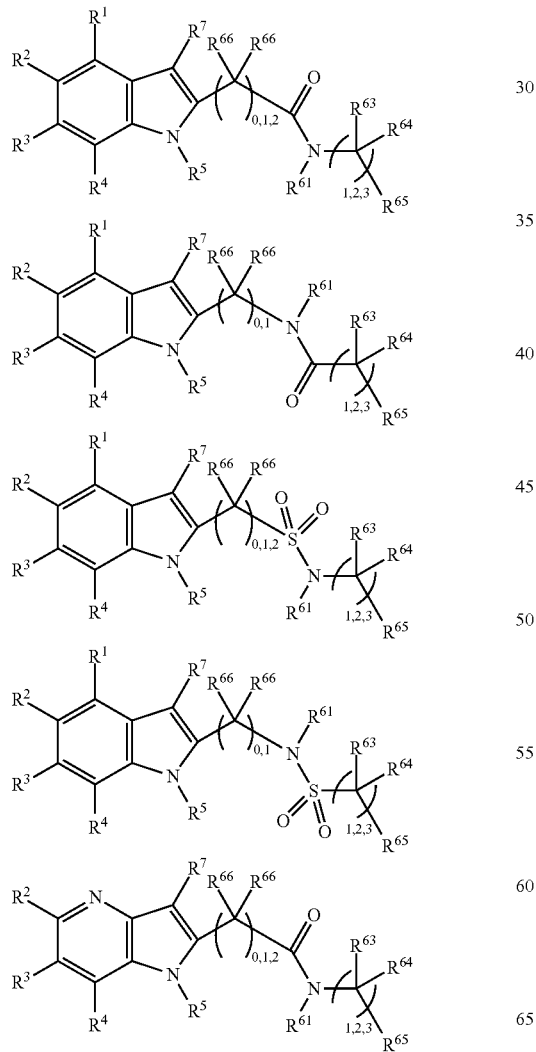

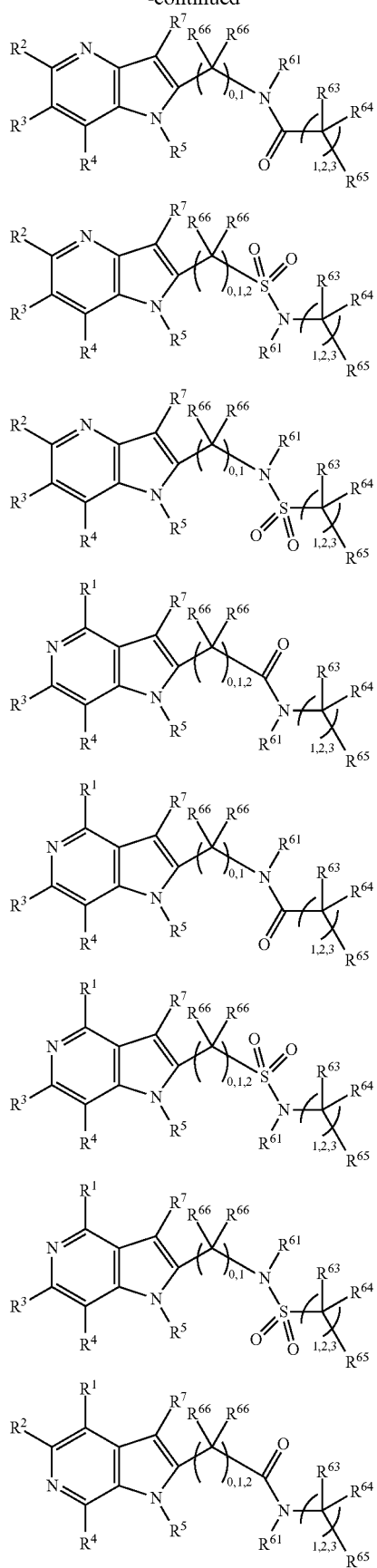

-continued

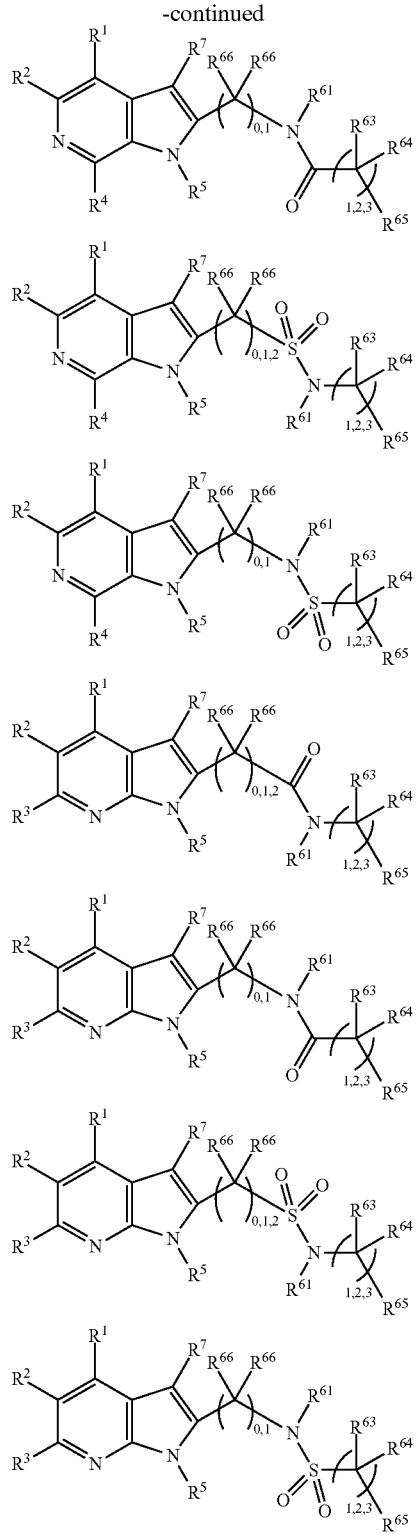

wherein $R^1$, $R^2$, $R^3$, $R^4$, $R^5$, $R^7$, $R^{61}$, $R^{63}$, $R^{64}$, $R^{65}$ and $R^{66}$ are as defined herein. In these compounds, in certain embodiments, when present $R^1$ and $R^4$ are both H, or $R^1$ and $R^4$ are both not H, or $R^1$ is not H and $R^4$ is H, or $R^4$ is not H and $R^1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H.

In further view of the typical embodiments already described, in certain embodiments the invention relates to a compound as defined above, which compound comprises one or other of the following formulae:

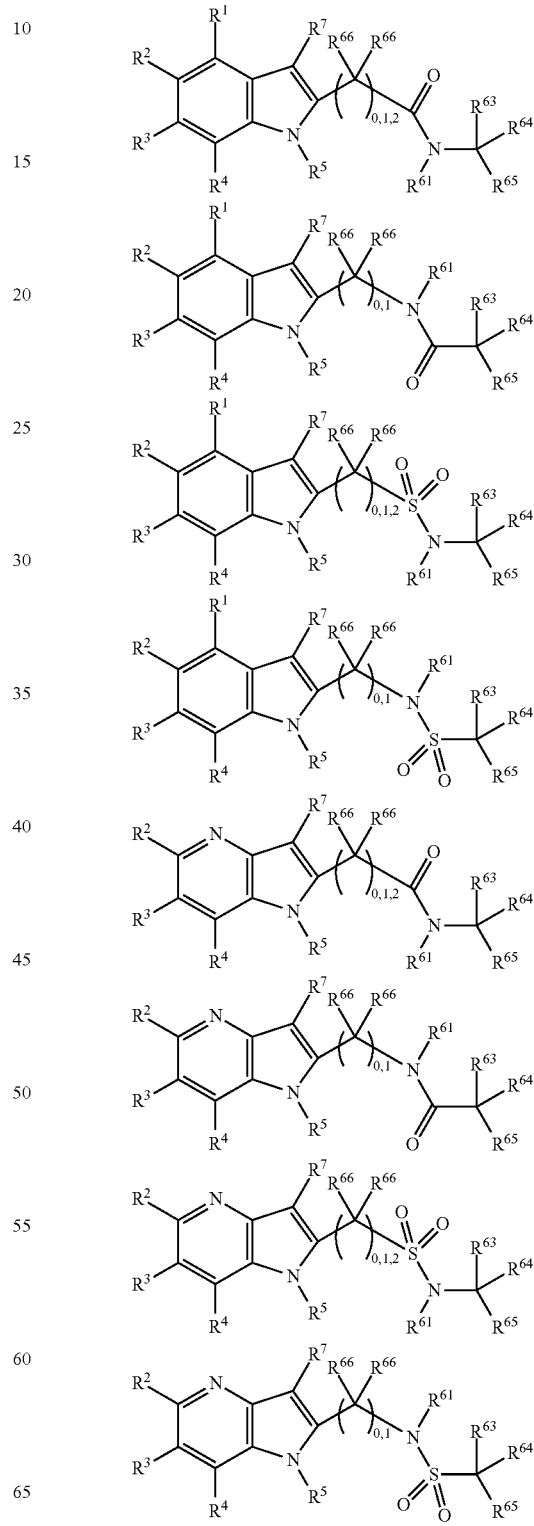

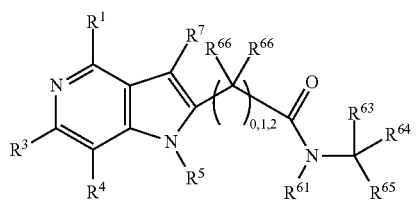
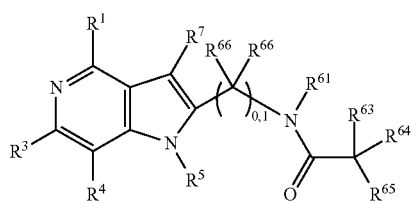
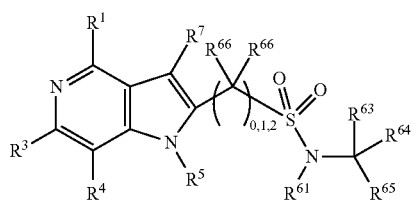
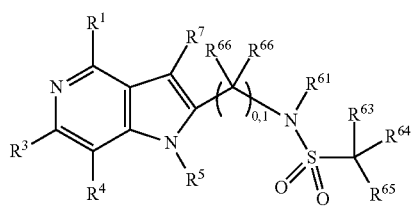
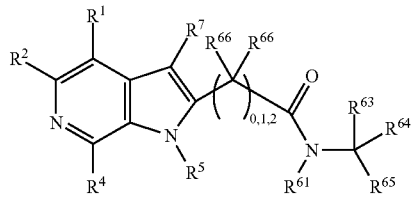
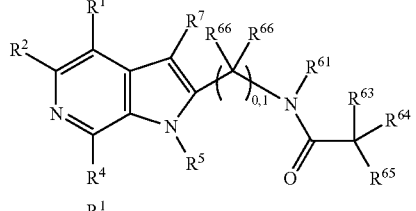
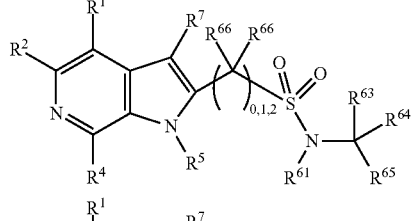
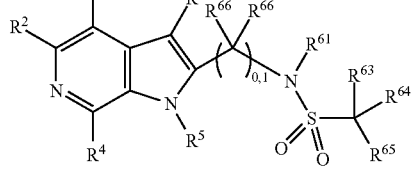

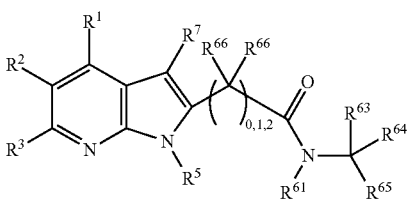
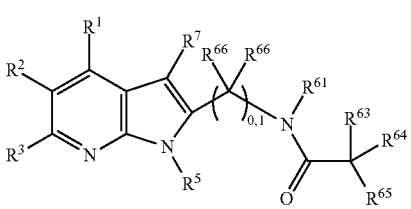
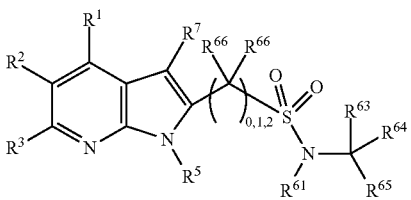
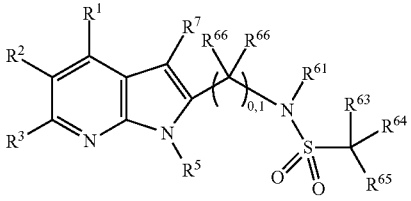

$R^1$, $R^2$, $R^3$, $R^4$, $R^5$, $R^7$, $R^{61}$, $R^{63}$, $R^{64}$, $R^{65}$ and $R^{66}$ are as defined herein. In these compounds, in certain embodiments, when present $R^1$ and $R^4$ are both H, or $R^1$ and $R^4$ are both not H, or $R^1$ is not H and $R^4$ is H, or $R^4$ is not H and $R_1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H.

In more preferred embodiments, in certain embodiments the invention relates to a compound as defined above, which compound comprises one or other of the following formulae:

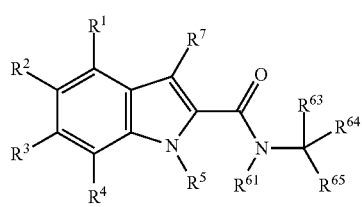
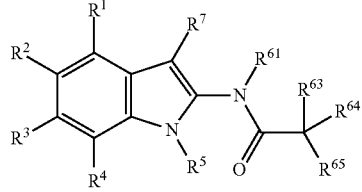

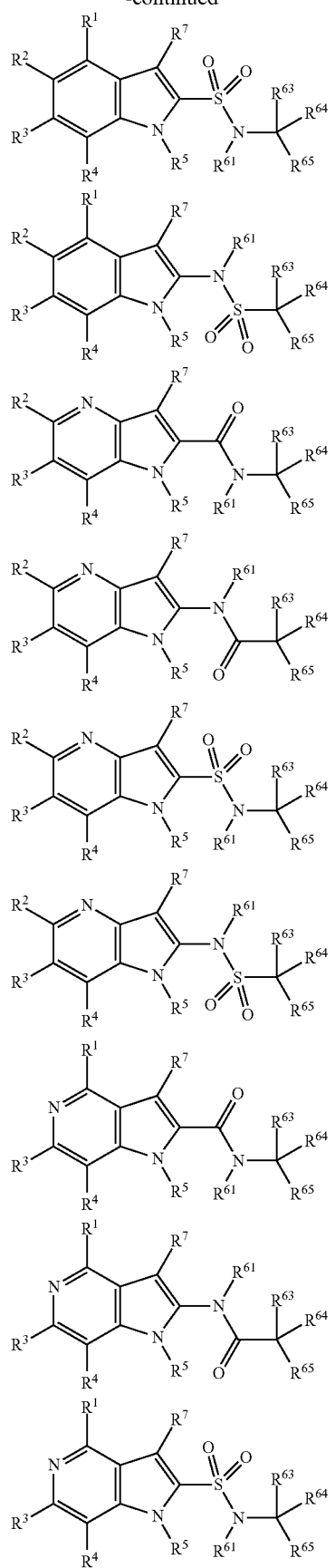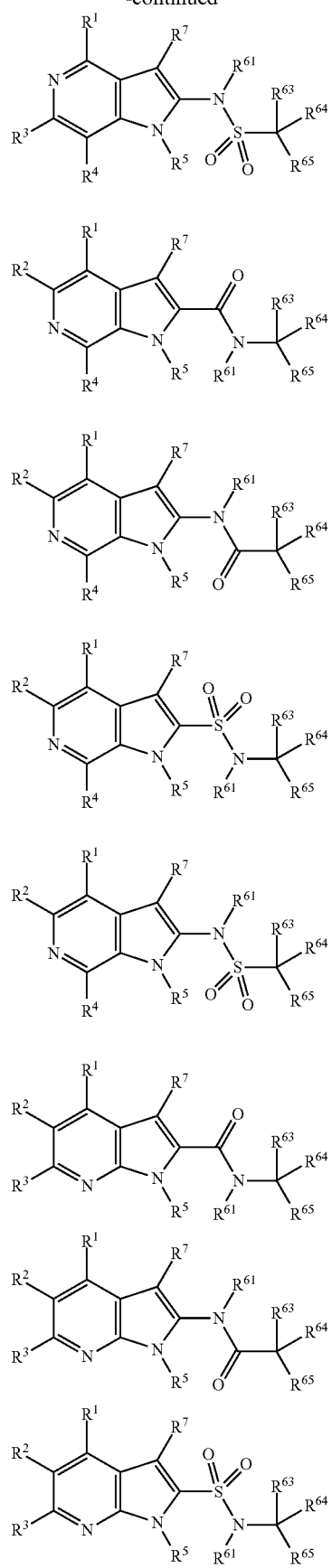

-continued

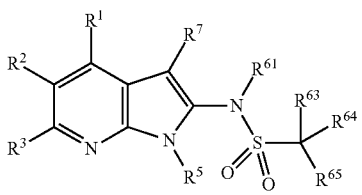

wherein R¹, R², R³, R⁴, R⁵, R⁷, R⁶¹, R⁶³, R⁶⁴, and R⁶⁵ are as defined herein. In these compounds, in certain embodiments, when present R¹ and R⁴ are both H, or R¹ and R⁴ are both not H, or R¹ is not H and R⁴ is H, or R⁴ is not H and R¹ is H. Furthermore, in certain embodiments when present R⁷ is H. Furthermore, in certain embodiments when present R⁵ is H. Still further, in certain embodiments, where present R² and R³ are both H, or R² and R³ are both not H, or R² is not H and R³ is H, or R³ is not H and R² is H.

In other embodiments which are less preferred, but not excluded, the invention relates to a compound as defined above, which compound comprises one or other of the following formulae:

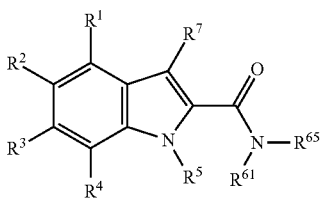

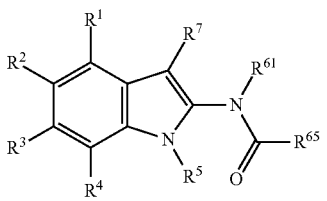

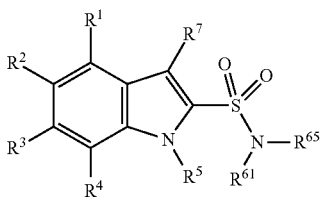

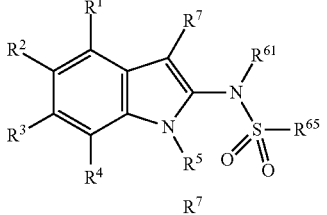

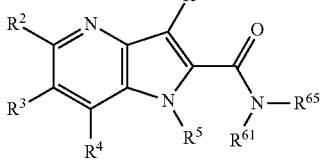

-continued

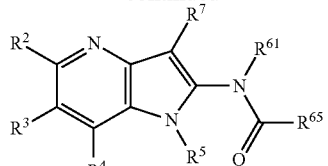

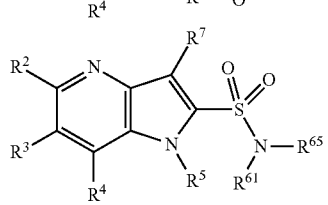

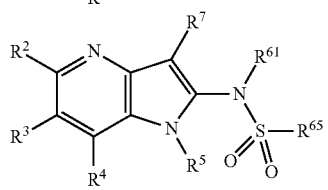

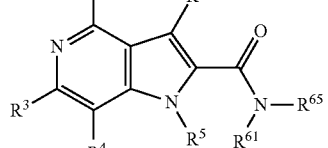

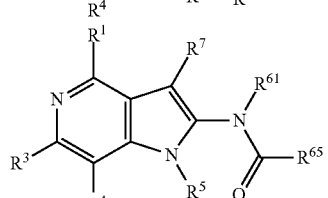

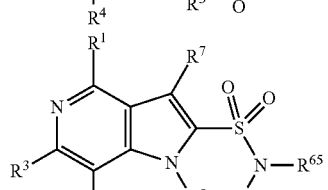

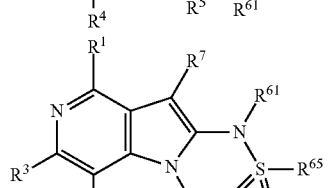

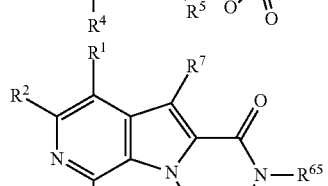

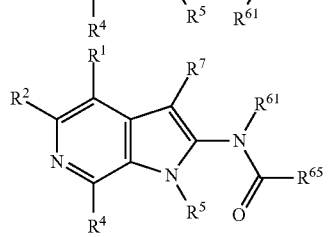

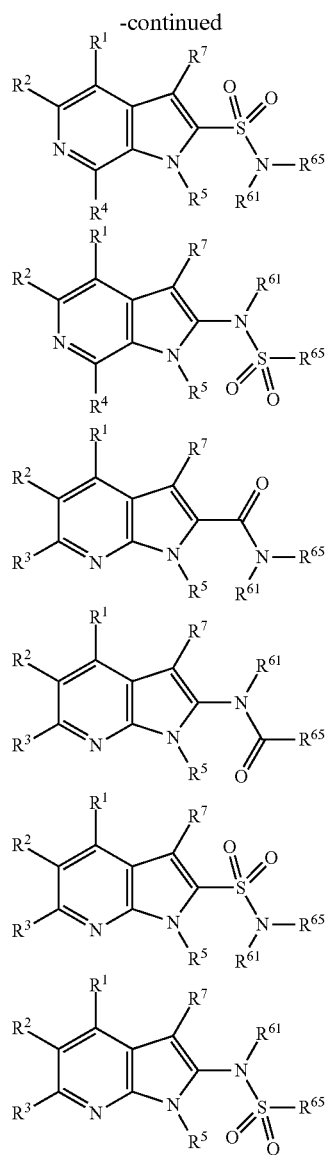

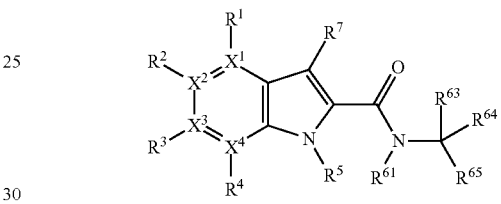

wherein, in these compounds (unlike in the more preferred compounds above) the $R^{65}$ is not attached to the rest of the structure via a group of the type —C($R^{63}$)($R^{64}$)—, and wherein $R^1$, $R^2$, $R^3$, $R^4$, $R^5$, $R^7$, $R^{61}$, and $R^{65}$ are otherwise as defined herein. In these compounds, typically $R^{65}$ is not a monocyclic heterocyclic group. In these compounds, in certain embodiments, when present $R^1$ and $R^4$ are both H, or $R^1$ and $R^4$ are both not H, or $R^1$ is not H and $R^4$ is H, or $R^4$ is not H and $R^1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H.

Although these other embodiments are less preferred, they are slightly more preferred when $R^{65}$ comprises a fused ring group attached directly through one of the ring atoms. Thus, in such slightly more preferred compounds, $R^{65}$ may typically be selected from:

fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene).

In more preferred embodiments, the invention relates to a compound as defined above, which compound comprises one of the following formulae:

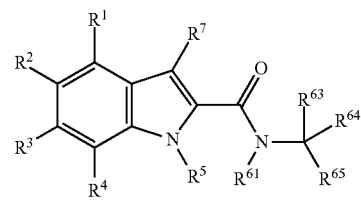

wherein $R^1$, $R^2$, $R^3$, $R^4$, $R^5$, $R^7$, $R^{61}$, $R^{63}$, $R^{64}$, and $R^{65}$ are as defined herein, provided that all of $X^1$, $X^2$, $X^3$ and $X^4$ are C, or one of $X^1$, $X^2$, $X^3$ and $X^4$ is N and the rest of $X^1$, $X^2$, $X^3$ and $X^4$ are C, for example:

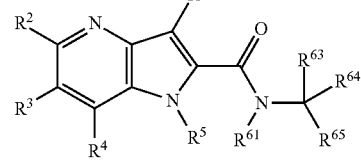

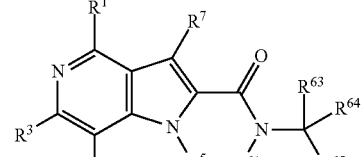

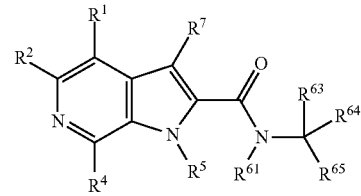

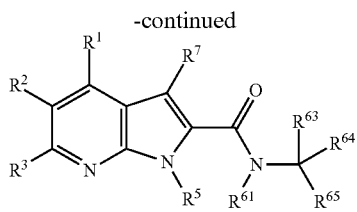

wherein $R^1$, $R^2$, $R^3$, $R^4$, $R^5$, $R^7$, $R^{61}$, $R^{63}$, $R^{64}$ and $R^{65}$ are as defined herein. In these compounds, in certain embodiments, when present $R^1$ and $R^4$ are both H, or $R^1$ and $R^4$ are both not H, or $R^1$ is not H and $R^4$ is H, or $R^4$ is not H and $R^1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H.

In any of the embodiments herein, and in particular in the preferred and more preferred embodiments described above, $R^1$, $R^2$, $R^3$, $R^4$, and $R^7$ are preferably independently selected from H and:

a halogen such as —F, —Cl, —Br and —I, preferably —F and —Cl;

—CN;

a substituted or unsubstituted linear or branched $C_1$-$C_6$ alkyl group such as such as methyl (Me), ethyl (Et), propyl (Pr), iso-propyl (i-Pr), cyclopropyl (cy-Pr), n-butyl (n-Bu), iso-butyl (i-Bu), tert-butyl (t-Bu), pentyl and hexyl, preferably -Me;

a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$, —$CBr_3$, —$CI_3$, —$CH_2CF_3$, —$CH_2CCl_3$, —$CH_2CBr_3$, and —$CH_2CI_3$), preferably —$CF_3$; and a substituted or unsubstituted linear or branched $C_1$-$C_7$ alkoxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —$OCH_2Cl$, —$OCHCl_2$, —$OCCl_3$, —O-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$), preferably —OMe;

and $R^5$ and $R^{61}$ are preferably independently selected from H and:

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ halogenated alkyl group (such as —$CH_2F$, —$CHF_2$, —$CF_3$, —$CCl_3$, —$CBr_3$, —$CI_3$, —$CH_2CF_3$, —$CH_2CCl_3$, —$CH_2CBr_3$, and —$CH_2CI_3$), preferably a linear or branched $C_1$-$C_6$ fluorinated alkyl group (such as —$CH_2F$, —$CHF_2$, —$CF_3$, —$CH_2CH_2F$, —$CH_2CHF_2$, and —$CH_2CF_3$); and a substituted or unsubstituted linear or branched $C_2$-$C_6$ alcohol group (such as —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);

and $R^{61}$ may further be selected from a substituted or unsubstituted cyclic $C_3$-$C_8$ alkyl group (such as cyclopropyl, cyclobutyl, cyclopentyl, cyclohexyl, cycloheptyl and cyclooctyl);

wherein $R^5$ is preferably H and $R^{61}$ is preferably H;

and $R^{65}$ is preferably selected from H and:

a cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, 4-keto-piperidinyl), 2-keto-piperazinyl, and 3-keto-piperazinyl;

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)-$I_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl); and fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene);

and $R^{63}$ and $R^{64}$ are preferably independently selected from H and:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$ —$CBr_3$, —$CI_3$, —$CH_2CF_3$, —$CH_2CCl_3$, —$CH_2CBr_3$, and —$CH_2CI_3$);

an —$NH_2$ group or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —$CH_2OH$, —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);

a substituted or unsubstituted cyclic amine or amido group (such as pyrrolidin-2-yl, pyrrolidin-3-yl, piperidin-2-yl, piperidin-3-yl, piperidin-4-yl, piperazin-1-yl, piperazin-2-yl, piperazin-3-yl, morpholin-2-yl, morpholin-3-yl, 2-keto-pyrrolidinyl, 3-keto-pyrrolidinyl, 2-keto-piperidinyl, 3-keto-piperidinyl, 4-keto-piperidinyl), 2-keto-piperazinyl, and 3-keto-piperazinyl;

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph-, 4-I-Ph-, 2,(3,4,5 or 6)-$F_2$-Ph-, 2,(3,4,5 or 6)-$Cl_2$-Ph-, 2,(3,4,5 or 6)-$Br_2$-Ph-, 2,(3,4,5 or 6)$4_2$-Ph-, 2,(3,4,5 or 6)-$Me_2$-Ph-, 2,(3,4,5 or 6)-$Et_2$-Ph-, 2,(3,4,5 or 6)-$Pr_2$-Ph-, 2,(3,4,5 or 6)-$Bu_2$-Ph-, 2,(3,4,5 or 6)-$(CN)_2$-Ph-, 2,(3,4,5 or 6)-$(NO_2)_2$-Ph-, 2,(3,4,5 or 6)-$(NH_2)_2$-Ph-, 2,(3,4,5 or 6)-$(MeO)_2$-Ph-, 2,(3,4,5 or 6)-$(CF_3)_2$-Ph-, 3,(4 or 5)-$F_2$-Ph-, 3,(4 or 5)-$Cl_2$-Ph-, 3,(4 or 5)-$Br_2$-Ph-, 3,(4 or 5)-$I_2$-Ph-, 3,(4 or 5)-$Me_2$-Ph-, 3,(4 or 5)-$Et_2$-Ph-, 3,(4 or 5)-$Pr_2$-Ph-, 3,(4 or 5)-$Bu_2$-Ph-, 3,(4 or 5)-$(CN)_2$-Ph-, 3,(4 or 5)-$(NO_2)_2$-Ph-, 3,(4 or 5)-$(NH_2)_2$-Ph-, 3,(4 or 5)-$(MeO)_2$-Ph-, 3,(4 or 5)-$(CF_3)_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-($NO_2$)-Ph-, 3-($NO_2$)-Ph-, 4-($NO_2$)-Ph-, 2-($NH_2$)-Ph-, 3-($NH_2$)-Ph-, 4-($NH_2$)-Ph-, 2-MeO-Ph-, 3-MeO-Ph-, 4-MeO-Ph-, 2-($NH_2$—CO)-Ph-, 3-($NH_2$—CO)-Ph-, 4-($NH_2$—CO)-Ph-, 2-$CF_3$-Ph-, 3-$CF_3$-Ph-, 4-$CF_3$-Ph-, 2-$CF_3$O-Ph-, 3-$CF_3$O-Ph-, and 4-$CF_3$O-Ph-);

a substituted or unsubstituted saturated or unsaturated heterocyclic group such as an aromatic heterocyclic group (such as pyridin-2-yl, pyridin-3-yl, pyridin-4-yl, thiophen-2-yl, thiophen-3-yl, pyrimidin-2-yl, pyrimidin-4-yl, pyrimidin-5-yl, pyrimidin-6-yl, tetrazole-1yl, tetrazole-2-yl, tetrazole-5-yl, oxazol-2-yl, oxazol-4-yl, oxazol-5-yl, isoxazol-3-yl, isoxazol-4-yl, isoxazol-5-yl, (1,3,4-oxadiazol)-2-yl, (1,3,4-oxadiazol)-4-yl, (1,3,4-oxadiazol)-5-yl, thiazol-2-yl, thiazol-4-yl, thiazol-5-yl, furan-2-yl, and furan-3-yl); or such as a substituted or unsubstituted saturated heterocyclic group (such as piperidin-2-yl, piperidin-3-yl, piperidin-4-yl, piperazin-1-yl, piperazin-2-yl, piperazin-3-yl, tetrahydrofuran-2-yl, and tetrahydrofuran-3-yl, tetrahydropyran-2-yl, tetrahydropyran-3-yl, tetrahydropyran-4-yl); and a group where $R^{63}$ and $R^{64}$ together form a 3-6 membered substituted or unsubstituted saturated or unsaturated carbocyclic or heterocyclic ring (such as a cyclopropyl, cyclobutyl, cyclopentyl, cyclopentenyl, cyclohexyl, cyclohexenyl, aziridine, azetidine, pyrrolidine, piperidine, piperazine, oxetane, tetrahydrofuran or tetrahydropyran ring);

and further preferably one of $R^{63}$ and $R^{64}$ is not H.

In any of the embodiments herein, and in particular in the preferred and more preferred embodiments described above, it is still more preferred that $R^1$, $R^3$, and $R^4$ are each independently selected from H and F, most preferably H; and/or $R^2$ is selected from —Cl, Br, —CN, —OMe and —OEt; and/or and $R^7$ is H; and/or $R^5$ and $R^{61}$ are selected from H and $C_1$-$C_6$ alkyl, most preferably $R^5$ and $R^{61}$ are both H; and/or $R^{65}$ is selected from a substituted or unsubstituted phenyl group, a substituted or unsubstituted pyrazol-4-yl group, a substituted or unsubstituted oxazol-4-yl group, and a substituted or unsubstituted isoxazol-3-yl group; and/or $R^{63}$ and $R^{64}$ are selected from groups in which $R^{63}$ and $R^{64}$ together form a 3-6 membered substituted or unsubstituted saturated or unsaturated carbocyclic or heterocyclic ring (such as a cyclopropyl, cyclobutyl, cyclopentyl, cyclopentenyl, cyclohexyl, cyclohexenyl, aziridine, azetidine, pyrrolidine, piperidine, piperazine, oxetane, tetrahydrofuran or tetrahydropyran ring). Furthermore, in certain of these more preferred embodiments $R^7$ is H. Furthermore, in certain of these more preferred embodiments $R^5$ is H. Still further, in these more preferred embodiments, $R^2$ and $R^3$ are both not H, or $R^2$ is not H and $R^3$ is H, or $R^3$ is not H and $R^2$ is H.

Some of the more preferred of the R substituents have been discussed above. However, the R substituents referred to in all of the compounds and structures herein will now be described generally and in more detail.

Typically, as has been described, the R substituents in any of the compounds herein, unless otherwise specified, are selected from H and an organic group, and may themselves be substituted or unsubstituted. An organic group may be any group common to organic chemistry, and has already been defined in detail above. In typical embodiments, where present $R^1$, $R^2$, $R^3$, $R^4$, $R^5$, $R^6$, $R^7$, $R^{61}$, $R^{62}$, $R^{63}$, $R^{64}$, $R^{65}$ and $R^{66}$ are each the same or different, and in some embodiments adjacent and/or proximal groups may form rings, as already mentioned above in detail in respect of $R^1$-$R^7$, although in the case of $R^5$ and $R^7$ it is preferred if $R^5$ and $R^7$ do not form rings and do not comprise rings. For the avoidance of doubt, in any of the compounds herein $R^{61}$ may form a ring with an $R^{66}$ or with $R^{63}$, $R^{64}$ or $R^{65}$. Similarly $R^{63}$ may form a ring with $R^{64}$ or $R^{65}$, and $R^{64}$ may for a ring with $R^{65}$. In addition, $R^{66}$ may form a ring with another $R^{66}$.

In more typical embodiments $R^1$, $R^2$, $R^3$, and $R^4$ are independently selected from H and a group selected from the following groups:

a halogen (such as F, Cl, Br and I);

a —CN group;

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ alkyl-aryl group (such as —$CH_2Ph$, —$CH_2(2,3$ or $4)F$-Ph, —$CH_2(2,3$ or $4)Cl$-Ph, —$CH_2(2,3$ or $4)Br$-Ph, —$CH_2(2,3$ or $4)I$-Ph, —$CH_2CH_2Ph$, —$CH_2CH_2CH_2Ph$, —$CH_2CH_2CH_2CH_2Ph$, —$CH_2CH_2CH_2CH_2CH_2Ph$, and —$CH_2CH_2CH_2CH_2CH_2CH_2Ph$);

a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$, —$CBr_3$, —$CI_3$, —$CH_2CF_3$, —$CH_2CCl_3$, —$CH_2CBr_3$, and —$CH_2CI_3$);

an —$NH_2$ group or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —NBuH, —$NPr_2$, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, —NH-2,(3,4,5 or 6)$Bu_2$-Ph;

a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl 4-keto-piperidinyl), 2-keto-piperazinyl, and 3-keto-piperazinyl;

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —$CH_2OH$, —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);

a substituted or unsubstituted linear or branched $C_1$-$C_6$ carboxylic acid group (such as —COOH, —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2Ph$, —(CO)$CH_2OH$, —(CO)$CH_2OCH_3$, —(CO)$CH_2NH_2$, —(CO)$CH_2NHMe$, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)$NHCH_2CH_2OH$, —(CO)$NHCH_2CH_2OMe$, —(CO)$NHCH_2CH_2NH_2$, —(CO)$NHCH_2CH_2NHMe$, and —(CO)$NHCH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2COOMe$, —$CH_2CH_2COOMe$, —$CH_2CH_2CH_2COOMe$, and —$CH_2CH_2CH_2CH_2COOMe$);

a substituted or unsubstituted linear or branched $C_1$-$C_6$ amide group (such as —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —$OCH_2Cl$, —$OCHCl_2$, —$OCCl_3$, —O-Ph, —O—$CH_2$-Ph, —O—$CH_2$-(2,3 or 4)-F-Ph, —O—$CH_2$-(2,3 or 4)-Cl-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$);

a substituted or unsubstituted linear or branched amino-alkoxy group (such as —$OCH_2CH_2NH_2$, —$OCH_2CH_2NHMe$, —$OCH_2CH_2NMe_2$, —$OCH_2CH_2NHEt$, and —$OCH_2CH_2NEt_2$;

a substituted or unsubstituted linear or branched sulphonyl group (such as —$SO_2Me$, —$SO_2Et$, —$SO_2Pr$, —$SO_2iPr$, —$SO_2Ph$, —$SO_2$-(2,3 or 4)-F-Ph, —$SO_2$-cyclopropyl, —$SO_2CH_2CH_2OCH_3$;

a substituted or unsubstituted linear or branched sulphonylamino group (such as —$SO_2NH_2$, —$SO_2NHMe$, —$SO_2NMe_2$, —$SO_2NHEt$, —$SO_2NEt_2$, —$SO_2$-pyrrolidine-N-yl, —$SO_2$-morpholine-N-yl, —$SO_2NHCH_2OMe$, and —$SO_2NHCH_2CH_2OMe$);

a substituted or unsubstituted linear or branched amino-sulphonyl group (such as —$NHSO_2Me$, —$NHSO_2Et$, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a substituted or unsubstituted cyclic aminosulphonyl-group (such as —N(SO$_2$)(CH$_2$)$_3$ and —N(SO$_2$)(CH$_2$)$_4$);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)2-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene); and where there are two R groups attached to the same atom, they may together form a group which is double bonded to that atom, (such as a carbonyl group (=O) or an alkene group (=C(R')$_2$) wherein each R' group is the same or different and is H or an organic group, preferably H or a straight or branched C$_1$-C$_6$ alkyl group).

In more typical embodiments R$^7$ is independently selected from H and a group selected from the following groups:

a halogen (such as F, Cl, Br and I);

a —CN group;

a substituted or unsubstituted linear or branched C$_1$-C$_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched C$_1$-C$_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched C$_1$-C$_6$ halogenated alkyl group (such as —CH$_2$F, —CHF$_2$, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$);

an —NH$_2$ group or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph;

an —OH group or a substituted or unsubstituted linear or branched C$_1$-C$_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched C$_1$-C$_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched C$_1$-C$_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched C$_1$-C$_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —OCH$_2$Cl, —OCHCl$_2$, —OCCl$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$);

a substituted or unsubstituted linera or branched sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$;

a substituted or unsubstituted linear or branched sulphonylamino group (such as —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe);

a substituted or unsubstituted linear or branched aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$).

In more typical embodiments $R^1$, $R^2$, $R^3$, $R^4$, and $R^7$ may be selected from more common small organic substituents. It is particularly preferred that at least one of $R^1$, $R^2$, $R^3$, and $R^4$ is not H. Thus, in certain embodiments $R^1$, $R^2$, $R^3$, $R^4$ and $R^7$ are independently selected from H and:

a halogen such as —F, —Cl, —Br and —I, preferably —F and —Cl, (more preferably wherein $R^2$ is selected from —Cl and Br, and $R^1$, $R^3$, and $R^4$ are selected from —H and —F);

—CN;

a substituted or unsubstituted linear or branched C$_1$-C$_6$ alkyl group such as such as methyl (Me), ethyl (Et), propyl (Pr), iso-propyl (i-Pr), cyclopropyl (cy-Pr), n-butyl (n-Bu), iso-butyl (i-Bu), tert-butyl (t-Bu), pentyl and hexyl, preferably -Me;

a substituted or unsubstituted linear or branched C$_1$-C$_6$ halogenated alkyl group (such as —CH$_2$F, —CHF$_2$, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$), preferably —CF$_3$; and a substituted or unsubstituted linear or branched C$_1$-C$_7$ alkoxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —OCH$_2$Cl, —OCHCl$_2$, —OCCl$_3$, —O-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe), preferably —OMe or —OEt.

In these compounds, and the other compounds herein, in certain embodiments, when present $R^1$ and $R^4$ are both H, or $R^1$ and $R^4$ are both not H, or $R^1$ is not H and $R^4$ is H, or $R^4$ is not H and $R^1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H. In these and other embodiments, when one of these groups is not H it is more typically selected from —F, —Cl, —Br, -Me, -MeO and —CN. Still further, where present both $R^{66}$ may be H or one $R^{66}$ may be H or both $R^{66}$ are not H. Where there are three or four $R^{66}$ groups, all three or four may be H or one, two, three or four may be not H.

In more typical embodiments $R^{66}$, may be selected from more common small organic substituents. It is particularly preferred that $R^{66}$ is selected from H and:

—F;

a substituted or unsubstituted linear or branched C$_1$-C$_6$ alkyl group such as such as methyl (Me), ethyl (Et), propyl (Pr), iso-propyl (i-Pr), cyclopropyl (cy-Pr), n-butyl (n-Bu), iso-butyl (i-Bu), tert-butyl (t-Bu), pentyl and hexyl, preferably -Me;

an —NH$_2$ group or a substituted or unsubstituted linear or branched primary secondary or tertiary C$_1$-C$_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted linear or branched C$_1$-C$_6$ halogenated alkyl group (such as —CH$_2$F, —CHF$_2$, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$), preferably —CF$_3$;

a substituted or unsubstituted linear or branched $C_1$-$C_7$ alkoxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —OCH$_2$Cl, —OCHCl$_2$, —OCCl$_3$, —O-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe), preferably —OMe; and where there are two $R^{66}$ groups attached to the same atom, they may together form a group which is double bonded to that atom, (such as a carbonyl group (=O) or an alkene group (=C(R')$_2$) wherein each R' group is the same or different and is H or an organic group, preferably H or a straight or branched $C_1$-$C_6$ alkyl group).

In these compounds, and the other compounds herein, in certain embodiments, when present $R_1$ and $R^4$ are both H, or $R_1$ and $R^4$ are both not H, or $R_1$ is not H and $R^4$ is H, or $R^4$ is not H and $R_1$ is H. Furthermore, in certain embodiments when present $R^7$ is H. Furthermore, in certain embodiments when present $R^5$ is H. Still further, in certain embodiments, where present $R^2$ and $R^3$ are both H, or $R^2$ and $R^3$ are both not H, or $R^2$ is not H and $R^3$ is H, or $R^3$ is not H and $R^2$ is H. In these and other embodiments, when one of these groups is not H it is more typically selected from —F, —Cl, —Br, -Me, -MeO, —OEt and —CN. Still further, where present both $R^{66}$ may be H or one $R^{66}$ may be H or both $R^{66}$ are not H.

In more typical embodiments $R^5$ and $R^{61}$ are groups attached to N atoms in the compounds of the invention. In preferred embodiments they are not large groups, nor do they contain hetero atoms attached directly to the N atom. They are typically selected from H and lower alkyl groups, or the like. Thus, in typical embodiments, $R^5$ and $R^{61}$ may be the same or different and may be independently selected from H and:

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ halogenated alkyl group (such as —CH$_2$F, —CHF$_2$, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$), preferably a linear or branched $C_1$-$C_6$ fluorinated alkyl group (such as —CH$_2$F, —CHF$_2$, —CF$_3$, —CH$_2$CH$_2$F, —CH$_2$CHF$_2$, and —CH$_2$CF$_3$); and a substituted or unsubstituted linear or branched $C_2$-$C_6$ alcohol group (such as —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH).

$R^{61}$ may further be selected from a substituted or unsubstituted cyclic $C_3$-$C_8$ alkyl group (such as cyclopropyl, cyclobutyl, cyclopentyl, cyclohexyl, cycloheptyl and cyclooctyl).

More preferably, $R^5$ is H. Further (independently) preferably $R^{61}$ is H. More preferably both $R^5$ and $R^{61}$ are H.

In more typical embodiments $R^{63}$, $R^{64}$, and $R^{65}$ are independently selected from H and a group selected from the following groups:

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CHF$_2$, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$);

an —NH$_2$ group or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted cyclic amine or amido group (such as pyrrolidin-1-yl, pyrrolidin-2-yl, piperidin-1-yl, piperidin-2-yl, piperidin-3-yl, piperidin-4-yl, piperazin-1-yl, piperazin-2-yl, piperazin-3-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, 4-keto-piperidinyl, 2-keto-piperazinyl, and 3-keto-piperazinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; ≥(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene); and $R^{63}$ and $R^{64}$ may together form a group which is double bonded to the carbon atom to which they are attached, (such as a carbonyl group (=O) or an alkene group (=C(R')$_2$) wherein each R' group is the same or different and is H or an organic group, preferably H or a straight or branched C$_1$-C$_6$ alkyl group).

Whilst in some embodiments $R^{65}$ may be H or an organic group, or the more typical groups described above, in preferred embodiments $R^{65}$ is selected from: a substituted or unsubstituted, straight or branched chain organic group; and a substituted or unsubstituted cyclic organic group. More typically $R^{65}$ comprises a cyclic group. Accordingly, $R^{65}$ may be selected from: a substituted or unsubstituted, saturated or unsaturated, aliphatic cyclic group; a substituted or unsubstituted, aromatic cyclic group; a substituted or unsubstituted, saturated or unsaturated, non-aromatic or aromatic, heterocyclic group; and fused ring systems comprising two or more fused rings selected from one or more of the above.

In certain embodiments $R^{65}$ is selected from:

a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, 4-keto-piperidinyl, 2-keto-piperazinyl, and 3-keto-piperazinyl);

a substituted or unsubstituted cyclic C$_3$-C$_8$ alkyl group (such as cyclopropyl, cyclobutyl, cyclopentyl, cyclohexyl, cycloheptyl and cyclooctyl);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl); and fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene).

In some preferred embodiments, the invention therefore provides a tryptophan-2,3-dioxygenase (TDO) and/or indoleamine-2,3-dioxygenase (IDO) inhibitor compound for use in medicine, which compound comprises the following formula:

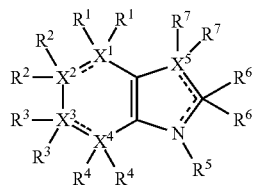

wherein $X^1$, $X^2$, $X^3$, $X^4$, and $X^5$ may be the same or different and each is independently selected from C, N and O; each atom having a dotted line may independently have a double bond or a single bond, provided that valencies at each atom are maintained; each $R^1$, $R^2$, $R^3$, $R^4$, $R^5$, and $R^7$ may be present or absent and may be the same or different and is selected from the groups as defined below, provided that the number of such R groups present is such that the valencies of $X^1$, $X^2$, $X^3$, $X^4$, and $X^5$ are maintained; one or two $R^6$ groups may be present and are selected from the groups as defined below, provided that the number of $R^6$ groups present is such that the valency of the carbon atom to which they are attached is maintained, and provided that at least one $R^6$ is an organic group comprising an atom double-bonded to an oxygen atom at an α-, β-, or γ-position to the carbon atom to which the $R^6$ is attached and in which the atom double-bonded to an oxygen atom is also bonded to a hetero-atom;

and wherein $R^5$ and $R^7$ do not comprise a cyclic group;

and wherein, where present, $R_1$, $R^2$, $R^3$, and $R^4$ are independently selected from H and a group selected from the following groups:

a halogen (such as F, Cl, Br and I);

a —CN group;

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ alkyl-aryl group (such as —CH$_2$Ph, —CH$_2$(2,3 or 4)F-Ph, —CH$_2$(2,3 or 4)Cl-Ph, —CH$_2$(2,3 or 4)Br-Ph, —CH$_2$(2,3 or 4)I-Ph, —CH$_2$CH$_2$Ph, —CH$_2$CH$_2$CH$_2$Ph, —CH$_2$CH$_2$CH$_2$CH$_2$Ph, —CH$_2$CH$_2$CH$_2$CH$_2$CH$_2$Ph, and —CH$_2$CH$_2$CH$_2$CH$_2$CH$_2$CH$_2$Ph);

a substituted or unsubstituted linear or branched $C_1$-$C_6$ halogenated alkyl group (such as —CH$_2$F, —CHF$_2$, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$);

an —NH$_2$ group or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)F$_2$-Ph, —NH-2,(3,4,5 or 6)Cl$_2$-Ph, —NH-2,(3,4,5 or 6)Br$_2$-Ph, —NH-2,(3,4,5 or 6)I$_2$-Ph, —NH-2,(3,4,5 or 6)Me$_2$-Ph, —NH-2,(3,4,5 or 6)Et$_2$-Ph, —NH-2,(3,4,5, or 6)Pr$_2$-Ph, —NH-2,(3,4,5 or 6)Bu$_2$-Ph;

a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, 4-keto-piperidinyl, 2-keto-piperazinyl, and 3-keto-piperazinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$OH, and —CH$_2$CH$_2$CH$_2$CH$_2$CH$_2$OH);

a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)CH$_2$Ph, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)-cyclopropyl, —(CO)-1,3-epoxypropan-2-yl; —(CO)NH$_2$, —(CO)NHMe, —(CO)NMe$_2$, —(CO)NHEt, —(CO)NEt$_2$, —(CO)-pyrollidine-N-yl, —(CO)-morpholine-N-yl, —(CO)-piperazine-N-yl, —(CO)—N-methyl-piperazine-N-yl, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —OCH$_2$Cl, —OCHCl$_2$, —OCCl$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted linear or branched sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$;

a sulphonylamino group (such as —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe);

an aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a cyclic aminosulphonyl-group (such as —N(SO$_2$)(CH$_2$)$_3$ and —N(SO$_2$)(CH$_2$)$_4$);

an aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)2-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene); and where there are two R groups attached to the same atom, they may together form a group which is double bonded to that atom, (such as a carbonyl group (=O) or an alkene group (=C(R')$_2$) wherein each R' group is the same or different and is H or an organic group, preferably H or a straight or branched $C_1$-$C_6$ alkyl group);

and wherein, where present, $R^7$ is independently selected from H and a group selected from the following groups:

a halogen (such as F, Cl, Br and I);

a —CN group;

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ halogenated alkyl group (such as —CH$_2$F, —CHF$_2$, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$);

an —NH$_2$ group or a substituted or unsubstituted linear or branched primary secondary or tertiary $C_1$-$C_6$ amine group (such as —NMeH, —NMe$_2$, —NEtH, —NEtMe, —NEt$_2$, —NPrH, —NPrMe, —NPrEt, —NPr$_2$, —NBuH, —NBuMe, —NBuEt, —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

an —OH group or a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$OH);

a substituted or unsubstituted linear or branched $C_1$-$C_6$ carboxylic acid group (such as —COOH, —CH$_2$COOH, —CH$_2$CH$_2$COOH, —CH$_2$CH$_2$CH$_2$COOH, —CH$_2$CH$_2$CH$_2$CH$_2$COOH, and —CH$_2$CH$_2$CH$_2$CH$_2$CH$_2$COOH);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)CH$_2$OH, —(CO)CH$_2$OCH$_3$, —(CO)CH$_2$NH$_2$, —(CO)CH$_2$NHMe, —(CO)CH$_2$NMe$_2$, —(CO)NH$_2$, —(CO)NHMe, —(CO)NMe$_2$, —(CO)NHEt, —(CO)NEt$_2$, —(CO)NHCH$_2$CH$_2$OH, —(CO)NHCH$_2$CH$_2$OMe, —(CO)NHCH$_2$CH$_2$NH$_2$, —(CO)NHCH$_2$CH$_2$NHMe, and —(CO)NHCH$_2$CH$_2$NMe$_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —CH$_2$COOMe, —CH$_2$CH$_2$COOMe, —CH$_2$CH$_2$CH$_2$COOMe, and —CH$_2$CH$_2$CH$_2$CH$_2$COOMe);

a substituted or unsubstituted linear or branched $C_1$-$C_6$ amide group (such as —CO—NH$_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NMe-CO-Me, —NMe-CO-Et, —NMe-CO-Pr, —NMe-CO-Bu, —NMe-CO-pentyl, —NMe-CO-hexyl;

a substituted or unsubstituted linear or branched $C_1$-$C_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —OCH$_2$Cl, —OCHCl$_2$, —OCCl$_3$—CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted linear or branched sulphonyl group (such as —SO$_2$Me, —SO$_2$Et, —SO$_2$Pr, —SO$_2$iPr, —SO$_2$CH$_2$CH$_2$OCH$_3$;

a substituted or unsubstituted linear or branched sulphonylamino group (such as —SO$_2$NH$_2$, —SO$_2$NHMe, —SO$_2$NMe$_2$, —SO$_2$NHEt, —SO$_2$NEt$_2$, —SO$_2$NHCH$_2$OMe, and —SO$_2$NHCH$_2$CH$_2$OMe);

a substituted or unsubstituted linear or branched aminosulphonyl group (such as —NHSO$_2$Me, —NHSO$_2$Et, —NHSO$_2$Pr, —NHSO$_2$iPr, —NHSO$_2$CH$_2$CH$_2$OCH$_3$);

preferably wherein $R^1$, $R^2$, $R^3$, $R^4$, and $R^7$ are selected from H and:

a halogen such as —F, —Cl, —Br and —I, preferably —F and —Cl, (more preferably wherein $R^2$ is selected from —Cl and Br, and $R^1$, $R^3$, and $R^4$ are selected from —H and —F);

—CN;

a substituted or unsubstituted linear or branched $C_1$-$C_6$ alkyl group such as such as methyl (Me), ethyl (Et), propyl (Pr), iso-propyl (i-Pr), cyclopropyl (cy-Pr), n-butyl (n-Bu), iso-butyl (i-Bu), tert-butyl (t-Bu), pentyl and hexyl, preferably -Me;

a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$, —$CBr_3$, —$CI_3$, —$CH_2CF_3$, —$CH_2CCl_3$, —$CH_2CBr_3$, and —$CH_2CI_3$), preferably —$CF_3$; and a substituted or unsubstituted linear or branched $C_1$-$C_7$ alkoxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —$OCH_2Cl$, —$OCHCl_2$, —$OCCl_3$, —O-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$), preferably —OMe or —OEt;

and wherein, where present, $R^5$ is independently selected from H and:

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ halogenated alkyl group (such as —$CH_2F$, —$CHF_2$, —$CF_3$, —$CCl_3$, —$CBr_3$, —$CI_3$, —$CH_2CF_3$, —$CH_2CCl_3$, —$CH_2CBr_3$, and —$CH_2CI_3$), preferably a linear or branched $C_1$-$C_6$ fluorinated alkyl group (such as —$CH_2F$, —$CHF_2$, —$CF_3$, —$CH_2CH_2F$, —$CH_2CHF_2$, and —$CH_2CF_3$); and a unsubstituted linear or branched $C_2$-$C_6$ alcohol group (such as —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);

preferably wherein $R^5$ is H.

In some still further preferred embodiments, the invention therefore provides a tryptophan-2,3-dioxygenase (TDO) and/or indoleamine-2,3-dioxygenase (IDO) inhibitor compound for use in medicine, which compound comprises the following formula:

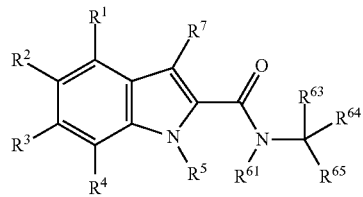

wherein $R^1$, $R^2$, $R^3$, $R^4$, $R^5$, $R^7$, $R^{61}$, $R^{63}$, $R^{64}$, and $R^{65}$ are as defined below, provided that neither $R^5$ nor $R^7$ comprises a cyclic group:

wherein, $R_1$, $R^2$, $R^3$, and $R^4$ are independently selected from H and a group selected from the following groups:

a halogen (such as F, Cl, Br and I);

a —CN group;

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ alkyl-aryl group (such as —$CH_2Ph$, —$CH_2(2,3$ or $4)F$-Ph, —$CH_2(2,3$ or $4)Cl$-Ph, —$CH_2(2,3$ or $4)Br$-Ph, —$CH_2(2,3$ or $4)I$-Ph, —$CH_2CH_2Ph$, —$CH_2CH_2CH_2Ph$, —$CH_2CH_2CH_2CH_2Ph$, —$CH_2CH_2CH_2CH_2CH_2Ph$, and —$CH_2CH_2CH_2CH_2CH_2CH_2Ph$);

a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$, —$CBr_3$, —$CI_3$, —$CH_2CF_3$, —$CH_2CCl_3$, —$CH_2CBr_3$, and —$CH_2CI_3$);

an —$NH_2$ group or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

a substituted or unsubstituted amino-aryl group (such as —NH-Ph, —NH-(2,3 or 4)F-Ph, —NH-(2,3 or 4)Cl-Ph, —NH-(2,3 or 4)Br-Ph, —NH-(2,3 or 4)I-Ph, —NH-(2,3 or 4)Me-Ph, —NH-(2,3 or 4)Et-Ph, —NH-(2,3 or 4)Pr-Ph, —NH-(2,3 or 4)Bu-Ph, NH-(2,3 or 4)OMe-Ph, —NH-(2,3 or 4)OEt-Ph, —NH-(2,3 or 4)OPr-Ph, —NH-(2,3 or 4)OBu-Ph, —NH-2,(3,4,5 or 6)$F_2$-Ph, —NH-2,(3,4,5 or 6)$Cl_2$-Ph, —NH-2,(3,4,5 or 6)$Br_2$-Ph, —NH-2,(3,4,5 or 6)$I_2$-Ph, —NH-2,(3,4,5 or 6)$Me_2$-Ph, —NH-2,(3,4,5 or 6)$Et_2$-Ph, —NH-2,(3,4,5, or 6)$Pr_2$-Ph, —NH-2,(3,4,5 or 6)$Bu_2$-Ph;

a substituted or unsubstituted cyclic amine or amido group (such as pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, piperazin-3-yl, morpholin-2-yl, morpholin-3-yl, morpholin-4-yl, 2-keto-pyrrolidinyl, 3-keto-pyrrolidinyl, 2-keto-piperidinyl, 3-keto-piperidinyl, 4-keto-piperidinyl, 2-keto-piperazinyl, and 3-keto-piperazinyl);

a substituted or unsubstituted cyclic $C_3$-$C_8$ alkyl group (such as cyclopropyl, cyclobutyl, cyclopentyl, cyclohexyl, cycloheptyl and cyclooctyl);

an —OH group or a substituted or unsubstituted linear or branched $C_1$-$C_6$ alcohol group (such as —$CH_2OH$, —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)_2CH_2OH$, —$CH_2CH_2CH_2CH_2CH_2OH$, and —$CH_2CH_2CH_2CH_2CH_2CH_2OH$);

a substituted or unsubstituted linear or branched $C_1$-$C_6$ carboxylic acid group (such as —COOH, —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)Ph, —(CO)$CH_2Ph$, —(CO)$CH_2OH$, —(CO)$CH_2OCH_3$, —(CO)$CH_2NH_2$, —(CO)$CH_2NHMe$, —(CO)$CH_2NMe_2$, —(CO)-cyclopropyl, —(CO)-1,3-epoxypropan-2-yl; —(CO)$NH_2$, —(CO)NHMe, —(CO)$NMe_2$, —(CO)NHEt, —(CO)$NEt_2$, —(CO)-pyrollidine-N-yl, —(CO)-morpholine-N-yl, —(CO)-piperazine-N-yl, —(CO)—N-methyl-piperazine-N-yl, —(CO)$NHCH_2CH_2OH$, —(CO)$NHCH_2CH_2OMe$, —(CO)$NHCH_2CH_2NH_2$, —(CO)$NHCH_2CH_2NHMe$, and —(CO)$NHCH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2COOMe$, —$CH_2CH_2COOMe$, —$CH_2CH_2CH_2COOMe$, and —$CH_2CH_2CH_2CH_2COOMe$);

a substituted or unsubstituted linear or branched $C_1$-$C_6$ amide group (such as —CO—$NH_2$, —CO—NMeH, —CO—NMe$_2$, —CO—NEtH, —CO—NEtMe, —CO—NEt$_2$, —CO—NPrH, —CO—NPrMe, and —CO—NPrEt);

a substituted or unsubstituted linear or branched C$_1$-C$_7$ amino carbonyl group (such as —NH—CO-Me, —NH—CO-Et, —NH—CO-Pr, —NH—CO-Bu, —NH—CO-pentyl, —NH—CO-hexyl, —NH—CO-Ph, —NMe-CO-Me, —NMe-CO-Et, —NMe-CO-Pr, —NMe-CO-Bu, —NMe-CO-pentyl, —NMe-CO-hexyl, —NMe-CO-Ph;

a substituted or unsubstituted linear or branched C$_1$-C$_7$ alkoxy or aryloxy group (such as —OMe, —OEt, —OPr, —O-i-Pr, —O-n-Bu, —O-i-Bu, —O-t-Bu, —O-pentyl, —O-hexyl, —OCH$_2$F, —OCHF$_2$, —OCF$_3$, —OCH$_2$Cl, —OCHCl$_2$, —OCCl$_3$, —O-Ph, —O—CH$_2$-Ph, —O—CH$_2$-(2,3 or 4)-F-Ph, —O—CH$_2$-(2,3 or 4)-Cl-Ph, —CH$_2$OMe, —CH$_2$OEt, —CH$_2$OPr, —CH$_2$OBu, —CH$_2$CH$_2$OMe, —CH$_2$CH$_2$CH$_2$OMe, —CH$_2$CH$_2$CH$_2$CH$_2$OMe, and —CH$_2$CH$_2$CH$_2$CH$_2$CH$_2$OMe);

a substituted or unsubstituted linear or branched aminoalkoxy group (such as —OCH$_2$CH$_2$NH$_2$, —OCH$_2$CH$_2$NHMe, —OCH$_2$CH$_2$NMe$_2$, —OCH$_2$CH$_2$NHEt, and —OCH$_2$CH$_2$NEt$_2$;

a substituted or unsubstituted linear or branched sulphonyl group (such as —SO$_2$Me, —SO$_2$Et, —SO$_2$Pr, —SO$_2$iPr, —SO$_2$Ph, —SO$_2$-(2,3 or 4)-F-Ph, —SO$_2$-cyclopropyl, —SO$_2$CH$_2$CH$_2$OCH$_3$;

a sulphonylamino group (such as —SO$_2$NH$_2$, —SO$_2$NHMe, —SO$_2$NMe$_2$, —SO$_2$NHEt, —SO$_2$NEt$_2$, —SO$_2$-pyrrolidine-N-yl, —SO$_2$-morpholine-N-yl, —SO$_2$NHCH$_2$OMe, and —SO$_2$NHCH$_2$CH$_2$OMe);

an aminosulphonyl group (such as —NHSO$_2$Me, —NHSO$_2$Et, —NHSO$_2$Pr, —NHSO$_2$iPr, —NHSO$_2$Ph, —NHSO$_2$-(2,3 or 4)-F-Ph, —NHSO$_2$-cyclopropyl, —NHSO$_2$CH$_2$CH$_2$OCH$_3$);

a cyclic aminosulphonyl-group (such as —N(SO$_2$)(CH$_2$)$_3$ and —N(SO$_2$)(CH$_2$)$_4$);

an aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)2-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a saturated or unsaturated, substituted or unsubstituted, heterocyclic group including an aromatic heterocyclic group and/or a non-aromatic heterocyclic group (such as pyrrole-1-yl, pyrrole-2-yl, pyrrole-3-yl, pyrazole-1-yl, pyrazole-3-yl, pyrazole-4-yl, pyrazole-5-yl, imidazole-1-yl, imidazole-2-yl, imidazole-4-yl, imidazole-5-yl, 1,2,3-triazole-1-yl, 1,2,3-triazole-4-yl, 1,2,3-triazole-5-yl, 1,2,4-triazole-1-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrimidin-6-yl, pyrazine-2-yl, pyrrolidine-1-yl, pyrrolidine-2-yl, pyrrolidine-3-yl, piperidine-1-yl, piperidine-2-yl, piperidine-3-yl, piperidine-4-yl, 2-azapiperidine-1-yl, 2-azapiperidine-3-yl, 2-azapiperidine-4-yl, 3-azapiperidine-1-yl, 3-azapiperidine-2-yl, 3-azapiperidine-4-yl, 3-azapiperidine-5-yl, piperazine-1-yl, piperazine-2-yl, furan-2-yl, furan-3-yl, pyran-2-yl, pyran-3-yl, pyran-4-yl, 2-azapyran-2-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-4-yl, 4-azapyran-5-yl, 4-azapyran-6-yl, tetrahydrofuran-2-yl, tetrahydrofuran-3-yl, 2-aza-tetrahydrofuran-2-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-3-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-2-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-3-yl, 3-aza-tetrahydropyran-4-yl, 3-aza-tetrahydropyran-5-yl, 3-aza-tetrahydropyran-6-yl, morpholine-2-yl, morpholine-3-yl, morpholine-4-yl, thiophen-2-yl, thiophen-3-yl, isothiazole-3-yl, isothiazole-4-yl, isothiazole-5-yl, thiazole-2-yl, thiazole-4-yl, thiazole-5-yl, thiopyran-2-yl, thiopyran-3-yl, thiopyran-4-yl, 2-azathiopyran-2-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-4-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-1-yl, tetrazole-2-yl, tetrazole-5-yl);

fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene); and where there are two R groups attached to the same atom, they may together form a group which is double bonded to that atom, (such as a carbonyl group (═O) or an alkene group (═C(R')$_2$) wherein each R' group is the same or different and is H or an organic group, preferably H or a straight or branched C$_1$-C$_6$ alkyl group);

and wherein, R$^7$ is independently selected from H and a group selected from the following groups:
a halogen (such as F, Cl, Br and I);
a —CN group;

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$, —$CBr_3$, —$CI_3$, —$CH_2CF_3$, —$CH_2CCl_3$, —$CH_2CBr_3$, and —$CH_2CI_3$);

an —$NH_2$ group or a substituted or unsubstituted linear or branched primary secondary or tertiary $C_1$-$C_6$ amine group (such as —NMeH, —$NMe_2$, —NEtH, —NEtMe, —$NEt_2$, —NPrH, —NPrMe, —NPrEt, —$NPr_2$, —NBuH, —NBuMe, —NBuEt, —$CH_2$—$NH_2$, —$CH_2$—NMeH, —$CH_2$—$NMe_2$, —$CH_2$—NEtH, —$CH_2$—NEtMe, —$CH_2$—$NEt_2$, —$CH_2$—NPrH, —$CH_2$—NPrMe, and —$CH_2$—NPrEt);

an —OH group or a substituted or unsubstituted linear or branched $C_1$-$C_6$ alcohol group (such as —$CH_2OH$, —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)2CH_2OH$, —$CH_2CH_2CH_2CH_2CH_2OH$, and —$CH_2CH_2CH_2CH_2CH_2CH_2OH$);

a substituted or unsubstituted linear or branched $C_1$-$C_6$ carboxylic acid group (such as —COOH, —$CH_2COOH$, —$CH_2CH_2COOH$, —$CH_2CH_2CH_2COOH$, —$CH_2CH_2CH_2CH_2COOH$, and —$CH_2CH_2CH_2CH_2CH_2COOH$);

a substituted or unsubstituted linear or branched carbonyl group (such as —(CO)Me, —(CO)Et, —(CO)Pr, —(CO)iPr, —(CO)nBu, —(CO)iBu, —(CO)tBu, —(CO)$CH_2OH$, —(CO)$CH_2OCH_3$, —(CO)$CH_2NH_2$, —(CO)$CH_2NHMe$, —(CO)$CH_2NMe_2$, —(CO)$NH_2$, —(CO)NHMe, —(CO)$NMe_2$, —(CO)NHEt, —(CO)$NEt_2$, —(CO)$NHCH_2CH_2OH$, —(CO)$NHCH_2CH_2OMe$, —(CO)$NHCH_2CH_2NH_2$, —(CO)$NHCH_2CH_2NHMe$, and —(CO)$NHCH_2CH_2NMe_2$;

a substituted or unsubstituted linear or branched $C_1$-$C_6$ carboxylic acid ester group (such as —COOMe, —COOEt, —COOPr, —COO-i-Pr, —COO-n-Bu, —COO-i-Bu, —COO-t-Bu, —$CH_2COOMe$, —$CH_2CH_2COOMe$, —$CH_2CH_2CH_2COOMe$, and —$CH_2CH_2CH_2CH_2COOMe$);

a substituted or unsubstituted linear or branched $C_1$-$C_6$ amide group (such as —CO—$NH_2$, —CO—NMeH, —CO—$NMe_2$, —CO—NEtH, —CO—NEtMe, —CO—$NEt_2$, —CO—NPrH, —CO—NPrMe, and —CO—NPrEt);

a substituted or unsubstituted linear or branched $C_1$-$C_7$ amino carbonyl group (such as —NH—CO-Me, —NH—CO-Et, —NH—CO-Pr, —NH—CO-Bu, —NH—CO-pentyl, —NH—CO-hexyl, —NMe-CO-Me, —NMe-CO-Et, —NMe-CO-Pr, —NMe-CO—Bu, —NMe-CO-pentyl, —NMe-CO-hexyl;

a substituted or unsubstituted linear or branched aminosulphonyl group (such as —$NHSO_2Me$, —$NHSO_2Et$, —$NHSO_2Pr$, —$NHSO_2iPr$, —$NHSO_2CH_2CH_2OCH_3$);

preferably wherein $R^1$, $R^2$, $R^3$, $R^4$, are selected from H and:

a halogen such as —F, —Cl, —Br and —I, preferably —F and —Cl, (more preferably wherein $R^2$ is selected from —Cl and Br, and $R^1$, $R^3$, and $R^4$ are selected from —H and —F);

—CN;

a substituted or unsubstituted linear or branched $C_1$-$C_6$ alkyl group such as such as methyl (Me), ethyl (Et), propyl (Pr), iso-propyl (i-Pr), cyclopropyl (cy-Pr), n-butyl (n-Bu), iso-butyl (i-Bu), tert-butyl (t-Bu), pentyl and hexyl, preferably -Me;

a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$, —$CBr_3$, —$CI_3$, —$CH_2CF_3$, —$CH_2CCl_3$, —$CH_2CBr_3$, and —$CH_2CI_3$), preferably —$CF_3$; and a substituted or unsubstituted linear or branched $C_1$-$C_7$ alkoxy group (such as —OMe, —OEt, —OPr, —O-i-Pr, —O-n-Bu, —O-i-Bu, —O-t-Bu, —O-pentyl, —O-hexyl, —$OCH_2F$, —$OCHF_2$, —$OCF_3$, —$OCH_2Cl$, —$OCHCl_2$, —$OCCl_3$, —O-Ph, —$CH_2OMe$, —$CH_2OEt$, —$CH_2OPr$, —$CH_2OBu$, —$CH_2CH_2OMe$, —$CH_2CH_2CH_2OMe$, —$CH_2CH_2CH_2CH_2OMe$, and —$CH_2CH_2CH_2CH_2CH_2OMe$), preferably —OMe, or —OEt;

preferably wherein $R^7$, is selected from H and:

a halogen such as —F and —Cl;

—CN;

a substituted or unsubstituted linear or branched $C_1$-$C_6$ alkyl group such as such as methyl (Me), ethyl (Et), propyl (Pr), iso-propyl (i-Pr), cyclopropyl (cy-Pr), n-butyl (n-Bu), iso-butyl (i-Bu), tert-butyl (t-Bu), pentyl and hexyl, preferably -Me; and a substituted or unsubstituted linear or branched $C_1$-$C_6$ halogenated alkyl group (such as —$CH_2F$, —$CHF_2$, —$CH_2Cl$, —$CH_2Br$, —$CH_2I$, —$CF_3$, —$CCl_3$, —$CBr_3$, —$CI_3$, —$CH_2CF_3$, —$CH_2CCl_3$, —$CH_2CBr_3$, and —$CH_2CI_3$), preferably —$CF_3$;

and wherein, $R^5$ and $R^{61}$ are independently selected from H and:

a substituted or unsubstituted linear or branched $C_1$-$C_6$ alkyl group (such as methyl (Me), ethyl (Et), propyl (Pr), iso-propyl (i-Pr), n-butyl (n-Bu), iso-butyl (i-Bu), tert-butyl (t-Bu), pentyl and hexyl);

a substituted or unsubstituted linear or branched $C_1$-$C_6$ halogenated alkyl group (such as —$CH_2F$, —$CHF_2$, —$CF_3$, —$CCl_3$, —$CBr_3$, —$CI_3$, —$CH_2CF_3$, —$CH_2CCl_3$, —$CH_2CBr_3$, and —$CH_2CI_3$), preferably a linear or branched $C_1$-$C_6$ fluorinated alkyl group (such as —$CH_2F$, —$CHF_2$, —$CF_3$, —$CH_2CH_2F$, —$CH_2CHF_2$, and —$CH_2CF_3$); and a unsubstituted linear or branched $C_2$-$C_6$ alcohol group (such as —$CH_2CH_2OH$, —$CH_2CH_2CH_2OH$, —$CH(CH_3)CH_2OH$, —$C(CH_3)_2OH$, —$CH_2CH_2CH_2CH_2OH$, —$CH(CH_3)CH_2CH_2OH$, —$CH(CH_3)CH(CH_3)OH$, —$CH(CH_2CH_3)CH_2OH$, —$C(CH_3)2CH_2OH$, —$CH_2CH_2CH_2CH_2OH$, and —$CH_2CH_2CH_2CH_2CH_2OH$);

and $R^{61}$ may further be selected from a substituted or unsubstituted cyclic $C_3$-$C_8$ alkyl group (such as cyclopropyl, cyclobutyl, cyclopentyl, cyclohexyl, cycloheptyl and cyclooctyl);

wherein $R^5$ is preferably H and $R^{61}$ is preferably H;

and wherein $R^{65}$ is a cyclic group, which cyclic group is bonded directly through one of its ring atoms to the carbon attached to $R^{63}$ and $R^{64}$, the cyclic group being selected from:

a cyclic amine or amido group (such as pyrrolidin-2-yl, pyrrolidin-3-yl, piperidin-2-yl, piperidin-4-yl, piperazin-2-yl, piperazin-3-yl, morpholin-2-yl, morpholin-3-yl, 2-keto-pyrrolidinyl, 3-keto-pyrrolidinyl, 2-keto-piperidinyl, 3-keto-piperidinyl, 4-keto-piperidinyl), 2-keto-piperazinyl, and 3-keto-piperazinyl;

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)$_2$-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-); and a saturated or unsaturated, substituted or unsubstituted, heterocyclic group such as an aromatic heterocyclic group and/or a non-aromatic heterocyclic group (such as pyrrole-2-yl, pyrrole-3-yl, pyrazole-3-yl, pyrazole-4-yl, imidazole-2-yl, imidazole-4-yl, 1,2,3-triazole-4-yl, 1,2,3-triazole-5-yl, 1,2,4-triazole-3-yl, 1,2,4-triazole-5-yl, pyridin-2-yl, pyridin-3-yl, pyridin-4-yl, pyridazine-3-yl, pyridazine-4-yl, pyrimidin-2-yl, pyrimidin-4-yl, pyrimidin-5-yl, pyrazine-2-yl, pyrrolidine-2-yl, pyrrolidine-3-yl, piperidine-2-yl, piperidine-3-yl, piperidine-4-yl, 2-azapiperidine-3-yl, 2-azapiperidine-4-yl, 3-azapiperidine-2-yl, 3-azapiperidine-4-yl, 3-azapiperidine-5-yl, piperazine-2-yl, furan-2-yl, furan-3-yl, pyran-2-yl, pyran-3-yl, pyran-4-yl, 2-azapyran-3-yl, 2-azapyran-4-yl, 2-azapyran-5-yl, 2-azapyran-6-yl, 3-azapyran-2-yl, 3-azapyran-4-yl, 3-azapyran-5-yl, 3-azapyran-6-yl, 4-azapyran-2-yl, 4-azapyran-3-yl, 4-azapyran-5-yl, 4-azapyran-6-yl, tetrahydrofuran-2-yl, tetrahydrofuran-3-yl, 2-aza-tetrahydrofuran-3-yl, 2-aza-tetrahydrofuran-4-yl, 2-aza-tetrahydrofuran-5-yl, 3-aza-tetrahydrofuran-2-yl, 3-aza-tetrahydrofuran-4-yl, 3-aza-tetrahydrofuran-5-yl, tetrahydropyran-2-yl, tetrahydropyran-3-yl, tetrahydropyran-4-yl, 2-aza-tetrahydropyran-3-yl, 2-aza-tetrahydropyran-4-yl, 2-aza-tetrahydropyran-5-yl, 2-aza-tetrahydropyran-6-yl, 3-aza-tetrahydropyran-2-yl, 3-aza-tetrahydropyran-4-yl, 3-aza-tetrahydropyran-5-yl, 3-aza-tetrahydropyran-6-yl, morpholine-2-yl, morpholine-3-yl, thiophen-2-yl, thiophen-3-yl, isothiazol-3-yl, isothiazol-4-yl, isothiazol-5-yl, thiazol-2-yl, thiazol-4-yl, thiazol-5-yl, thiopyran-2-yl, thiopyran-3-yl, thiopyran-4-yl, 2-azathiopyran-3-yl, 2-azathiopyran-4-yl, 2-azathiopyran-5-yl, 2-azathiopyran-6-yl, 3-azathiopyran-2-yl, 3-azathiopyran-4-yl, 3-azathiopyran-5-yl, 3-azathiopyran-6-yl, 4-azathiopyran-2-yl, 4-azathiopyran-3-yl, 4-azathiopyran-5-yl, 4-azathiopyran-6-yl, thiolane-2-yl, thiolane-3-yl, thiane-2-yl, thiane-3-yl, thiane-4-yl, oxazol-2-yl, oxazol-4-yl, oxazol-5-yl, isoxazol-3-yl, isoxazol-4-yl, isoxazol-5-yl, furazan-3-yl, (1,3,4-oxadiazol)-2-yl, (1,3,4-oxadiazol)-5-yl, (1,2,4-oxadiazol)-3-yl, (1,2,4-oxadiazol)-5-yl; and tetrazole-5-yl); and fused ring systems comprising two or three or more fused rings, which rings may be substituted or unsubstituted, preferably wherein the rings are selected from one, two, or more of the above aromatic groups and aromatic or non-aromatic heterocyclic groups, (e.g. fused ring systems such as naphthalene, anthracene, phenanthrene, phenalene, biphenylene, pentalene, indene, as-indacene, s-indacene, acenaphthylene, fluorene, fluoranthene, acephenanthrylene, azulene, heptalene, indole, indazole, benzimidazole, 4-azaindole, 5-azaindole, 6-azaindole, 7-azaindole, isoindole, 4-azaisoindole, 5-azaisoindole, 6-azaisoindole, 7-azaisoindole, indolizine, 1-azaindolizine, 2-azaindolizine, 3-azaindolizine, 5-azaindolizine, 6-azaindolizine, 7-azaindolizine, 8-azaindolizine, 9-azaindolizine, purine, carbazole, carboline, benzofuran, isobenzofuran, benzothiophene, isobenzothiophene, quinoline, cinnoline, quinazoline, quinoxaline, 5-azaquinoline, 6-azaquinoline, 7-azaquinoline, naphthyridine, isoquinoline, phthalazine, 6-azaisoquinoline, 7-azaisoquinoline, pteridine, chromene, isochromene, acridine, phenanthridine, perimidine, phenanthroline, phenoxazine, xanthene, phenoxanthiin, and/or thianthrene);

and wherein $R^{63}$ and $R^{64}$ are independently selected from H and the following groups provided that one of $R^{63}$ and $R^{64}$ is not H:

a substituted or unsubstituted linear or branched $C_1$-$C_6$ alkyl group (such as Me, Et, Pr, i-Pr, n-Bu, i-Bu, t-Bu, pentyl and hexyl);

a substituted or unsubstituted linear or branched $C_1$-$C_6$ halogenated alkyl group (such as —CH$_2$F, —CHF$_2$, —CH$_2$Cl, —CH$_2$Br, —CH$_2$I, —CF$_3$, —CCl$_3$, —CBr$_3$, —CI$_3$, —CH$_2$CF$_3$, —CH$_2$CCl$_3$, —CH$_2$CBr$_3$, and —CH$_2$CI$_3$);

a substituted or unsubstituted linear or branched primary secondary or tertiary $C_1$-$C_6$ amine group (such as —CH$_2$—NH$_2$, —CH$_2$—NMeH, —CH$_2$—NMe$_2$, —CH$_2$—NEtH, —CH$_2$—NEtMe, —CH$_2$—NEt$_2$, —CH$_2$—NPrH, —CH$_2$—NPrMe, and —CH$_2$—NPrEt);

a substituted or unsubstituted cyclic $C_3$-$C_8$ alkyl group (such as cyclopropyl, cyclobutyl, cyclopentyl, cyclohexyl, cycloheptyl and cyclooctyl);

a substituted or unsubstituted linear or branched $C_1$-$C_6$ alcohol group (such as —CH$_2$OH, —CH$_2$CH$_2$OH, —CH$_2$CH$_2$CH$_2$OH, —CH(CH$_3$)CH$_2$OH, —C(CH$_3$)$_2$OH, —CH$_2$CH$_2$CH$_2$CH$_2$OH, —CH(CH$_3$)CH$_2$CH$_2$OH, —CH(CH$_3$)CH(CH$_3$)OH, —CH(CH$_2$CH$_3$)CH$_2$OH, —C(CH$_3$)$_2$CH$_2$OH, —CH$_2$CH$_2$CH$_2$CH$_2$CH$_2$OH, and —CH$_2$CH$_2$CH$_2$CH$_2$CH$_2$CH$_2$OH);

a substituted or unsubstituted cyclic amine or amido group (such as pyrrolidin-2-yl, pyrrolidin-3-yl, piperidin-2-yl, piperidin-3-yl, piperidin-4-yl, piperazin-2-yl, piperazin-3-yl, morpholin-2-yl, morpholin-3-yl, 2-keto-pyrrolidinyl, 3-keto-pyrrolidinyl, 2-keto-piperidinyl, 3-keto-piperidinyl, 4-keto-piperidinyl), 2-keto-piperazinyl, and 3-keto-piperazinyl;

a substituted or unsubstituted aromatic group (such as Ph-, 2-F-Ph-, 3-F-Ph-, 4-F-Ph-, 2-Cl-Ph-, 3-Cl-Ph-, 4-Cl-Ph-, 2-Br-Ph-, 3-Br-Ph-, 4-Br-Ph-, 2-I-Ph-, 3-I-Ph-, 4-I-Ph-, 2,(3,4,5 or 6)-F$_2$-Ph-, 2,(3,4,5 or 6)-Cl$_2$-Ph-, 2,(3,4,5 or 6)-Br$_2$-Ph-, 2,(3,4,5 or 6)-I$_2$-Ph-, 2,(3,4,5 or 6)-Me$_2$-Ph-, 2,(3,4,5 or 6)-Et$_2$-Ph-, 2,(3,4,5 or 6)-Pr$_2$-Ph-, 2,(3,4,5 or 6)-Bu$_2$-Ph-, 2,(3,4,5 or 6)-(CN)$_2$-Ph-, 2,(3,4,5 or 6)-(NO$_2$)$_2$-Ph-, 2,(3,4,5 or 6)-(NH$_2$)$_2$-Ph-, 2,(3,4,5 or 6)-(MeO)$_2$-Ph-, 2,(3,4,5 or 6)-(CF$_3$)$_2$-Ph-, 3,(4 or 5)-F$_2$-Ph-, 3,(4 or 5)-Cl$_2$-Ph-, 3,(4 or 5)-Br$_2$-Ph-, 3,(4 or 5)-I$_2$-Ph-, 3,(4 or 5)-Me$_2$-Ph-, 3,(4 or 5)-Et$_2$-Ph-, 3,(4 or 5)-Pr$_2$-Ph-, 3,(4 or 5)-Bu$_2$-Ph-, 3,(4 or 5)-(CN)$_2$-Ph-, 3,(4 or 5)-(NO$_2$)$_2$-Ph-, 3,(4 or 5)-(NH$_2$)$_2$-Ph-, 3,(4 or 5)-(MeO)2-Ph-, 3,(4 or 5)-(CF$_3$)$_2$-Ph-, 2-Me-Ph-, 3-Me-Ph-, 4-Me-Ph-, 2-Et-Ph-, 3-Et-Ph-, 4-Et-Ph-, 2-Pr-Ph-, 3-Pr-Ph-, 4-Pr-Ph-, 2-Bu-Ph-, 3-Bu-Ph-, 4-Bu-Ph-, 2-(CN)-Ph-, 3-(CN)-Ph-, 4-(CN)-Ph-, 2-(NO$_2$)-Ph-, 3-(NO$_2$)-Ph-, 4-(NO$_2$)-Ph-, 2-(NH$_2$)-Ph-, 3-(NH$_2$)-Ph-, 4-(NH$_2$)-Ph-, 2-MeO-Ph-, 3-MeO-Ph-, 4-MeO-Ph-, 2-(NH$_2$—CO)-Ph-, 3-(NH$_2$—CO)-Ph-, 4-(NH$_2$—CO)-Ph-, 2-CF$_3$-Ph-, 3-CF$_3$-Ph-, 4-CF$_3$-Ph-, 2-CF$_3$O-Ph-, 3-CF$_3$O-Ph-, and 4-CF$_3$O-Ph-);

a substituted or unsubstituted saturated or unsaturated heterocyclic group such as an aromatic heterocyclic group (such as pyridin-2-yl, pyridin-3-yl, pyridin-4-yl, thiophen- 2-yl, thiophen-3-yl, pyrimidin-2-yl, pyrimidin-4-yl, pyrimidin-5-yl, pyrimidin-6-yl, tetrazole-5-yl, oxazol-2-yl, oxazol-4-yl, oxazol-5-yl, isoxazol-3-yl, isoxazol-4-yl, isoxazol-5-yl, (1,3,4-oxadiazol)-2-yl, (1,3,4-oxadiazol)-5-yl, (1,3-thiazol)-2-yl, (1,3-thiazol)-4-yl, (1,3-thiazol)-5-yl, furan-2-yl, and furan-3-yl); or such as a substituted or unsubstituted saturated heterocyclic group (such as piperidin-2-yl, piperidin-3-yl, piperidin-4-yl, piperazin-2-yl, piperazin-3-yl, tetrahydrofuran-2-yl, and tetrahydrofuran-3-yl, tetrahydropyran-2-yl, tetrahydropyran-3-yl, tetrahydropyran-4-yl); and a group where $R^{63}$ and $R^{64}$ together form a 3-6 membered substituted or unsubstituted saturated or unsaturated carbocyclic or heterocyclic ring (such as a cyclopropyl, cyclobutyl, cyclopentyl, cyclopentenyl, cyclohexyl, cyclohexenyl, aziridine, azetidine, pyrrolidine, piperidine, piperazine, oxetane, tetrahydrofuran or tetrahydropyran ring);

provided that when one of $R^{63}$ and $R^{64}$ is H and the other is Me, $R^{65}$ is not 3-MeO-Ph-, and that when $R^{65}$ is -Ph, and one of $R^{63}$ and $R^{64}$ is H, the other of $R^{63}$ and $R^{64}$ is not —CH(OH)-Ph.

Thus, the present invention provides a TDO or IDO compound for use in medicine, which compound comprises a formula selected from one of the following:

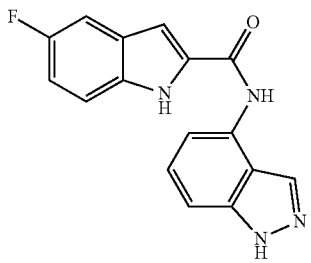

1

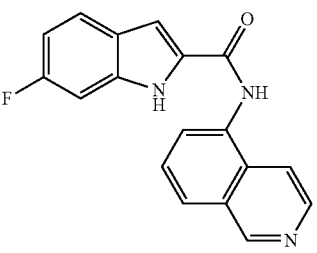

2

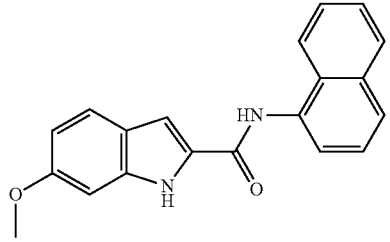

3

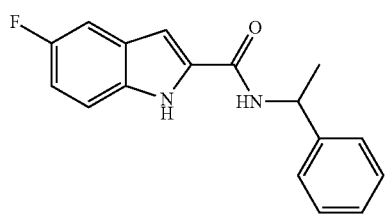

4

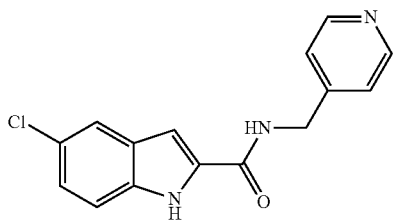

5

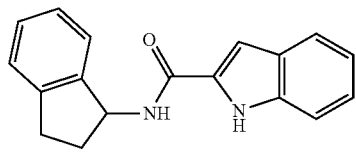

6

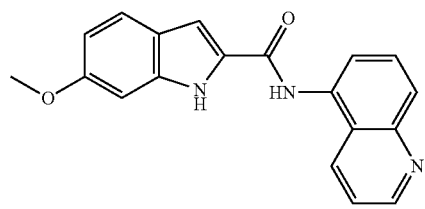

7

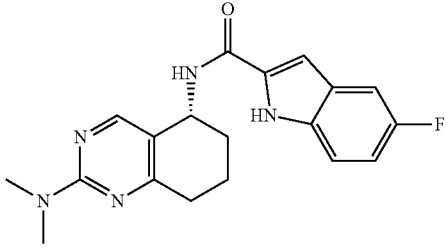

8

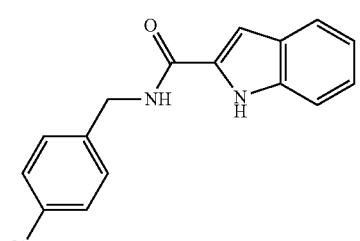

9

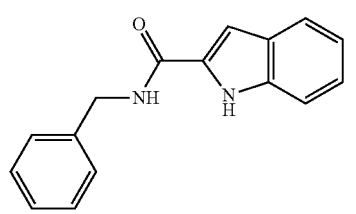

10

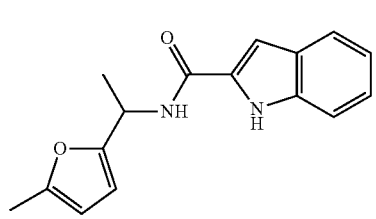

11

12
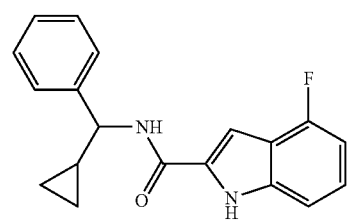
13
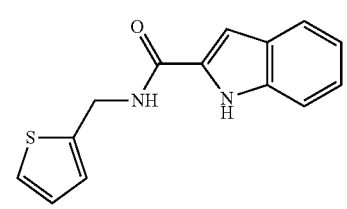
14
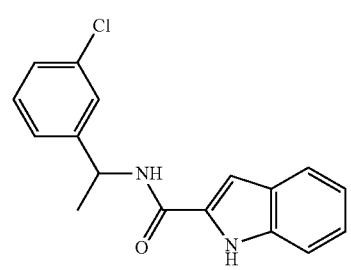
15
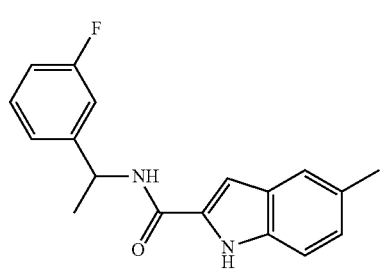
16
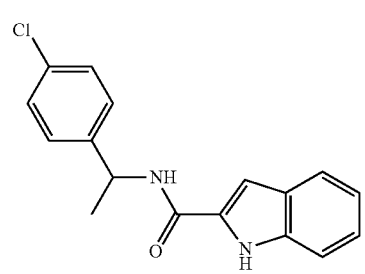
17
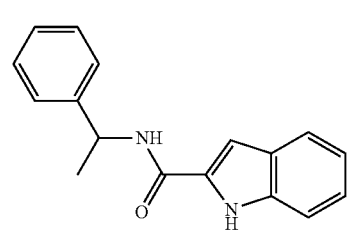
18
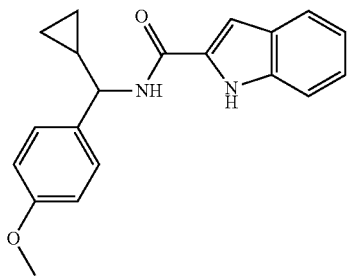
19
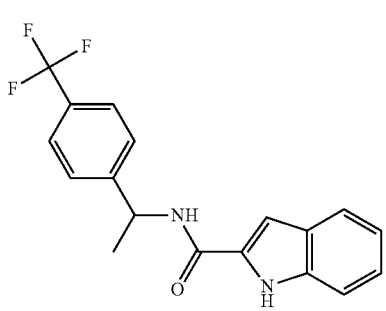
20
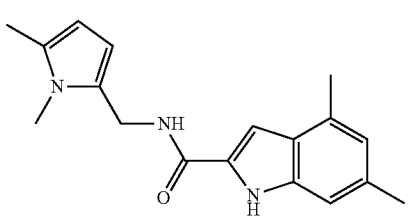
21
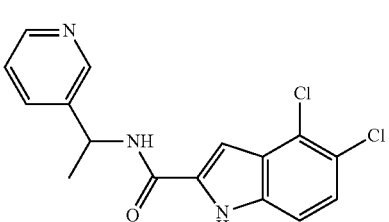
22
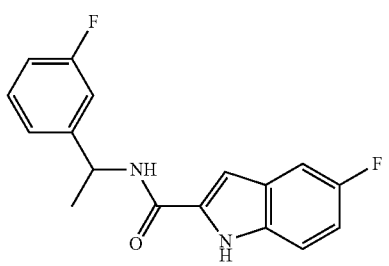
23
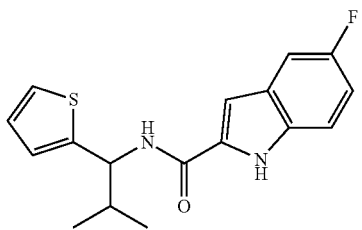

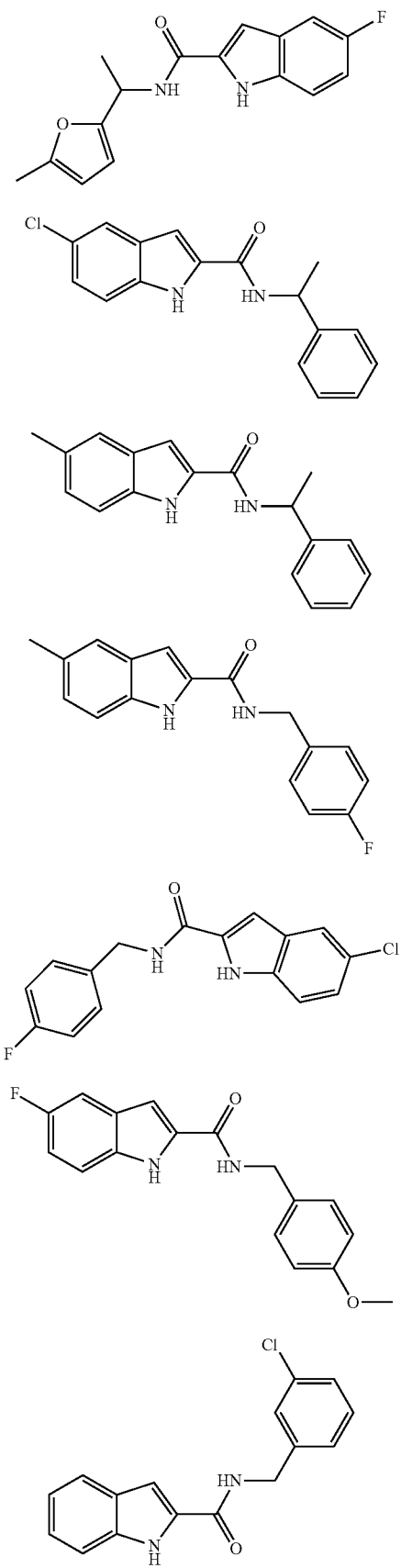
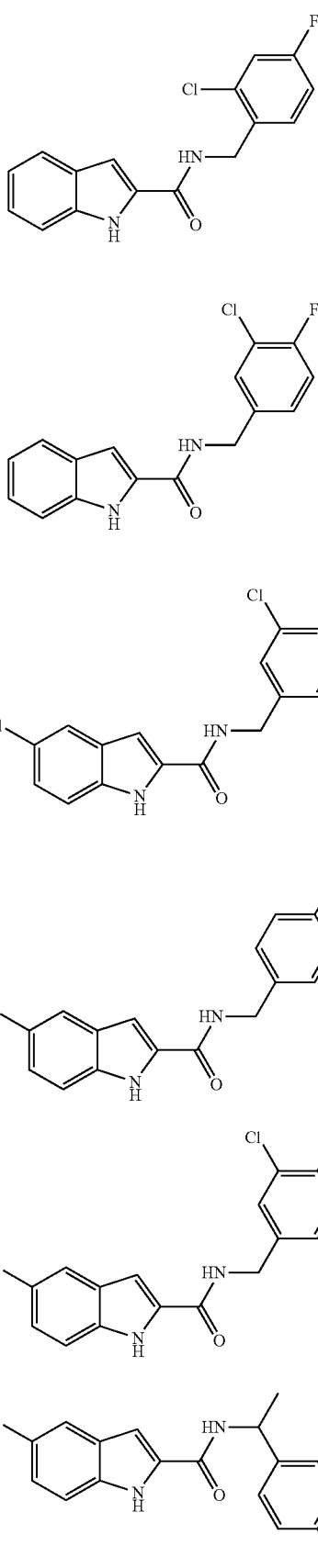

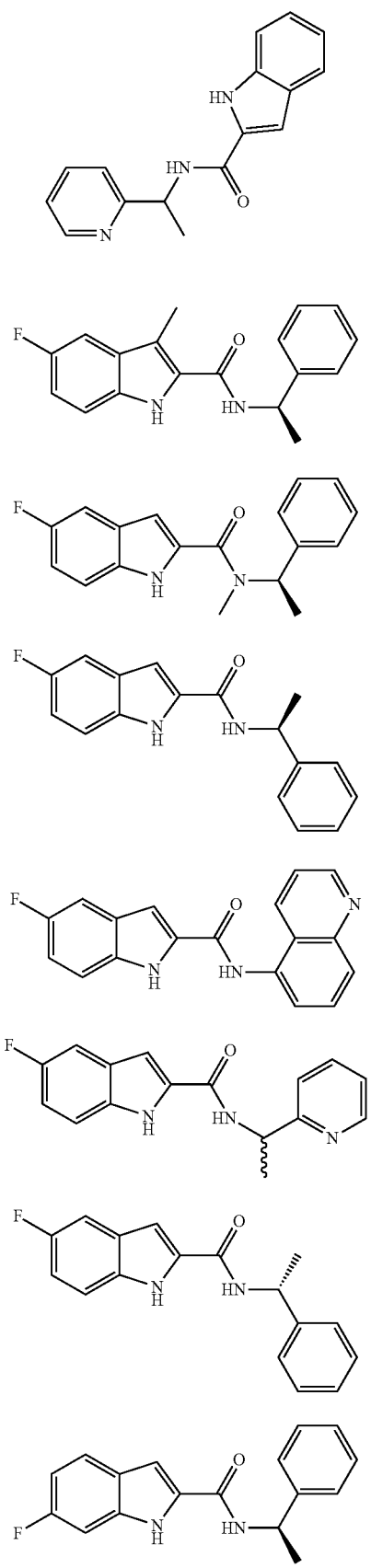
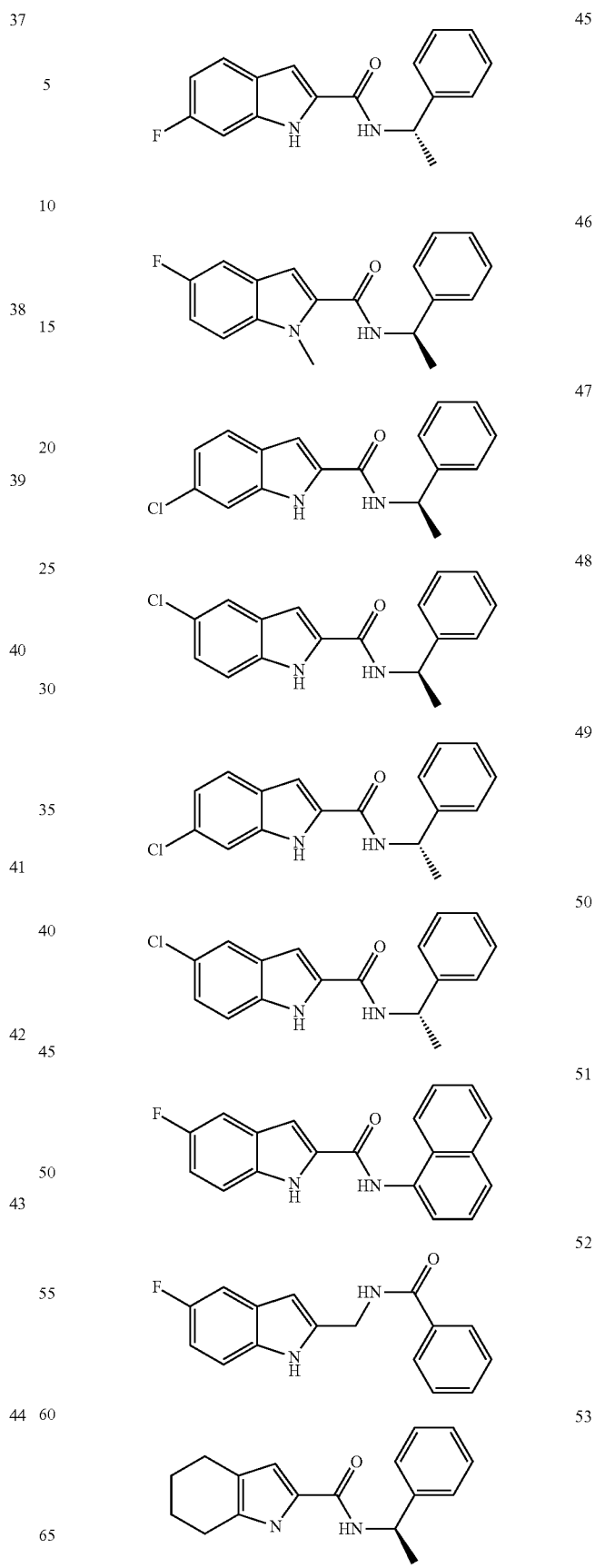

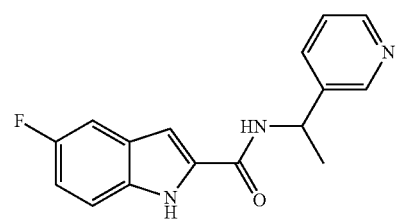
54
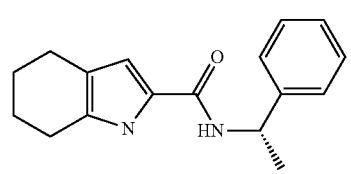
55
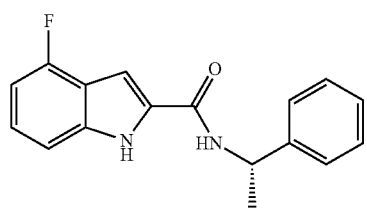
56
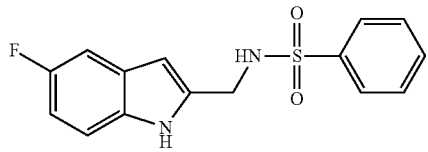
57
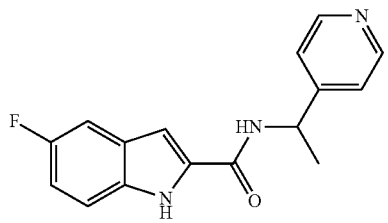
58
59
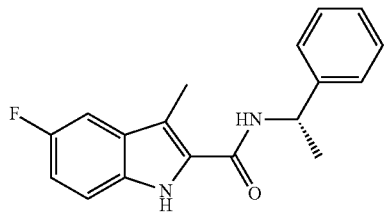
60
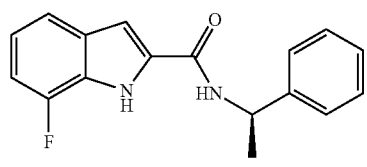
61
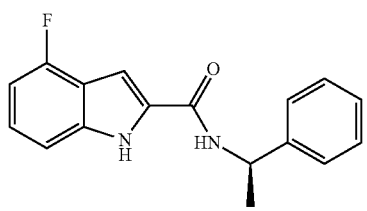
62
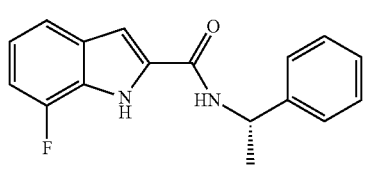
63
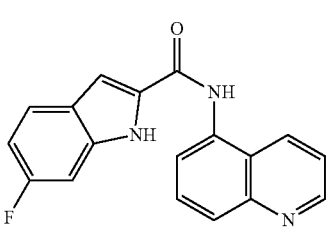
64
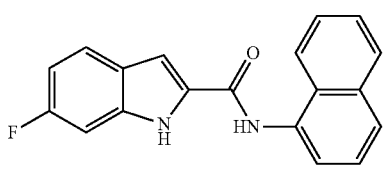
65
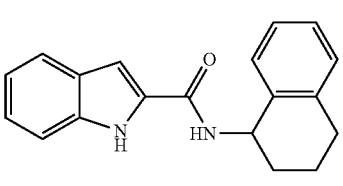
66
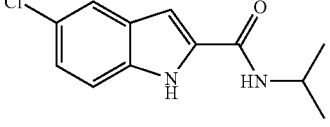
67
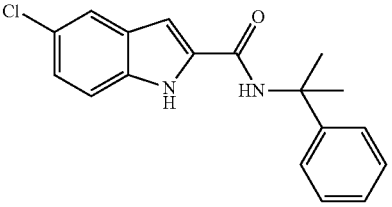
68
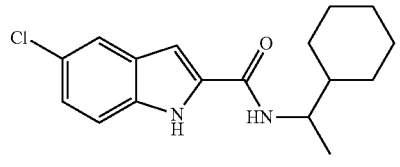
69

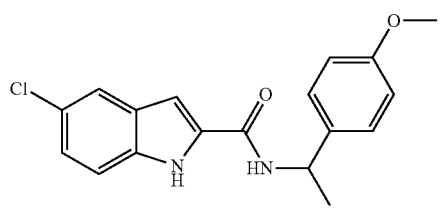
70
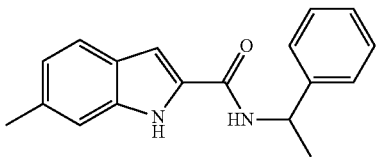
78
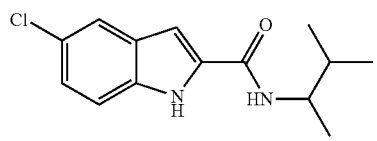
71
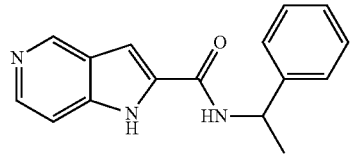
79
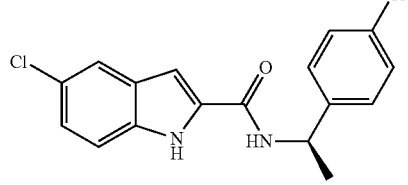
72
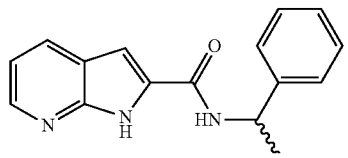
80
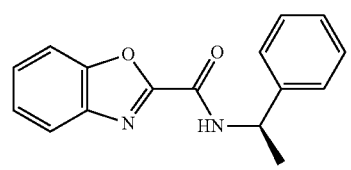
73
81
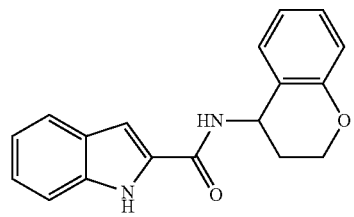
74
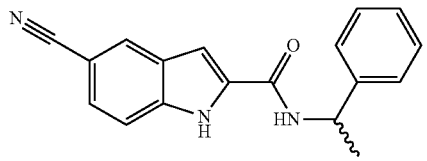
82
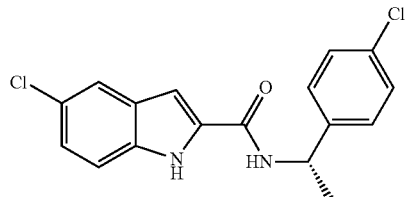
75
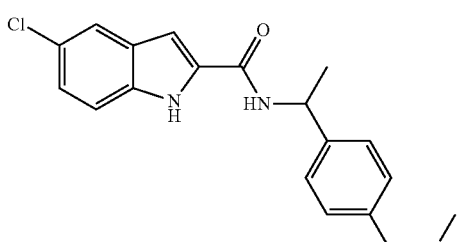
83
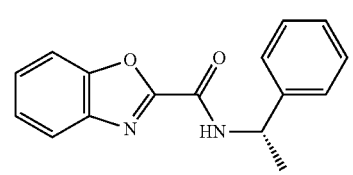
76
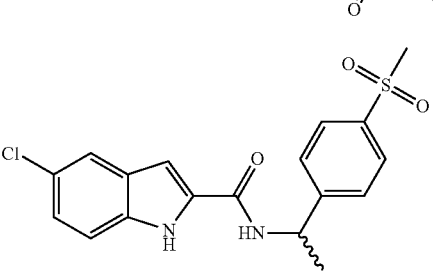
84
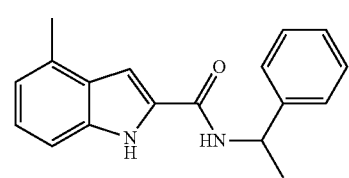
77
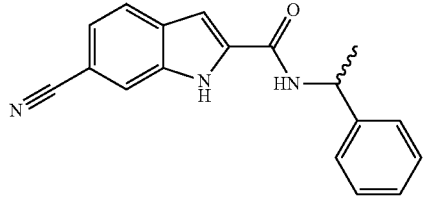
85

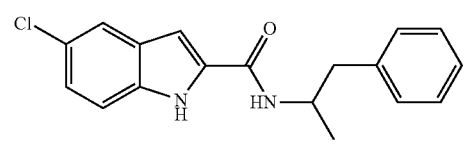
86
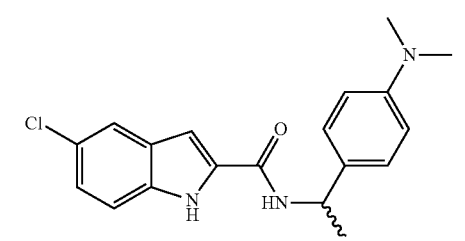
87
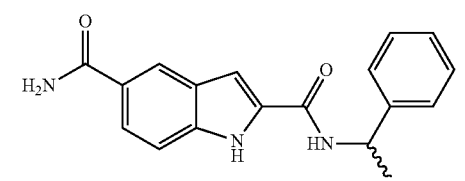
88
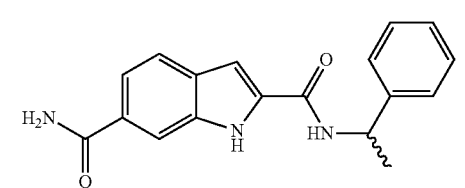
89
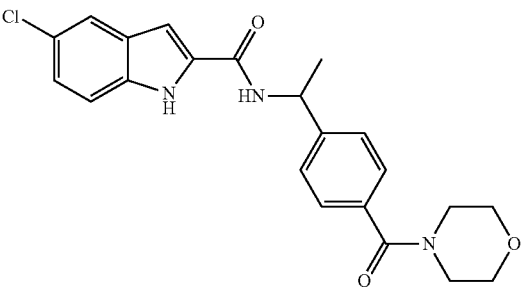
90
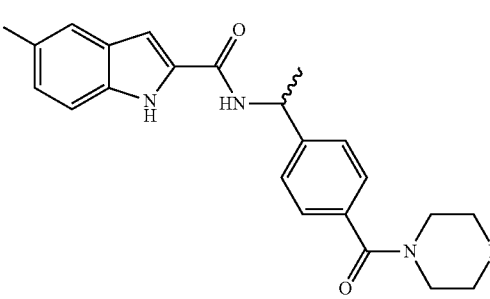
91
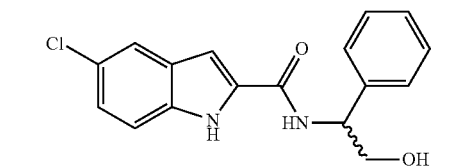
92
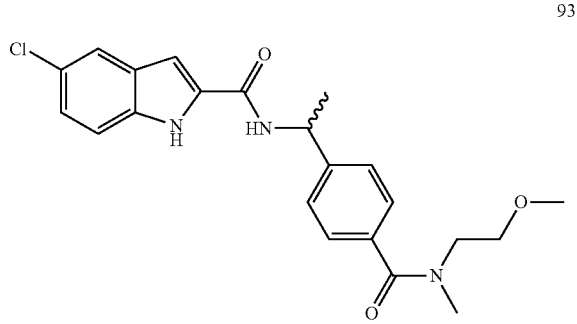
93
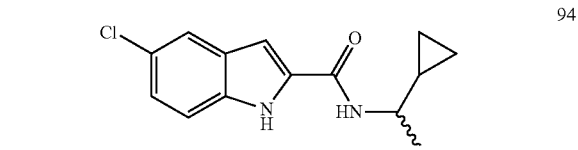
94
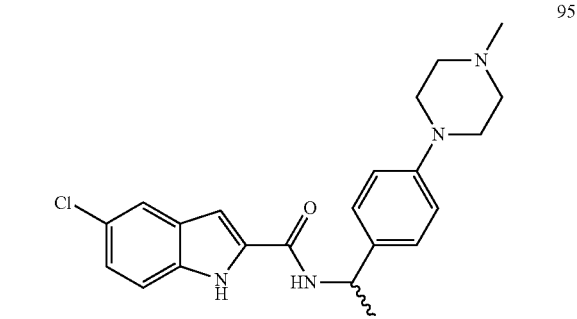
95
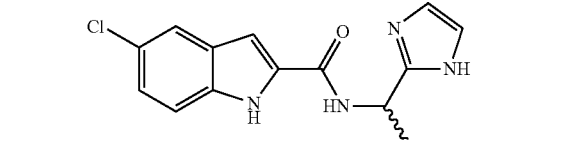
96
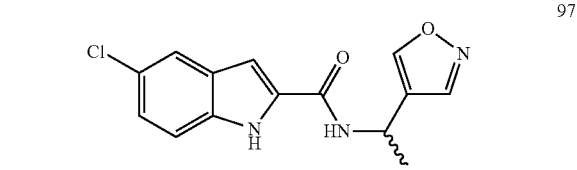
97
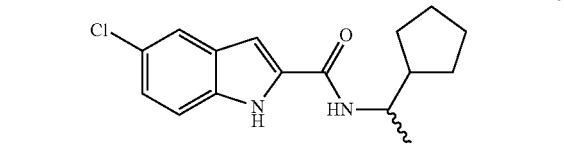
98
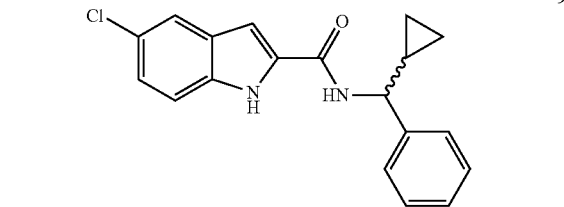
99

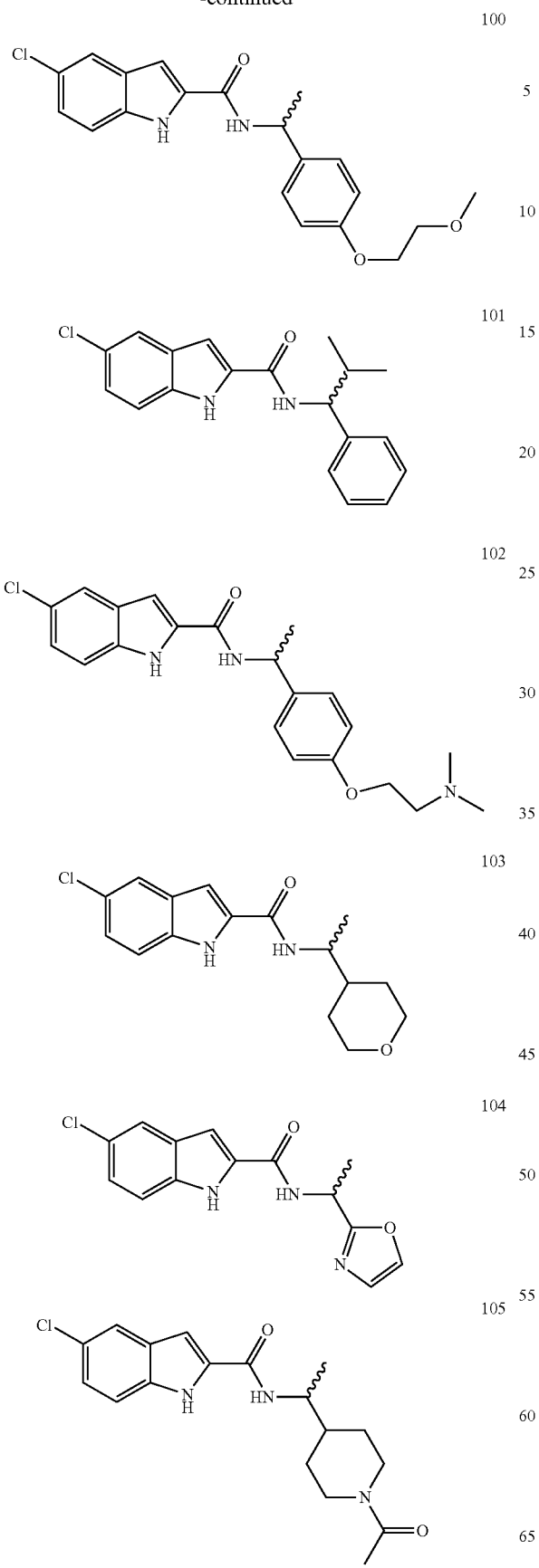
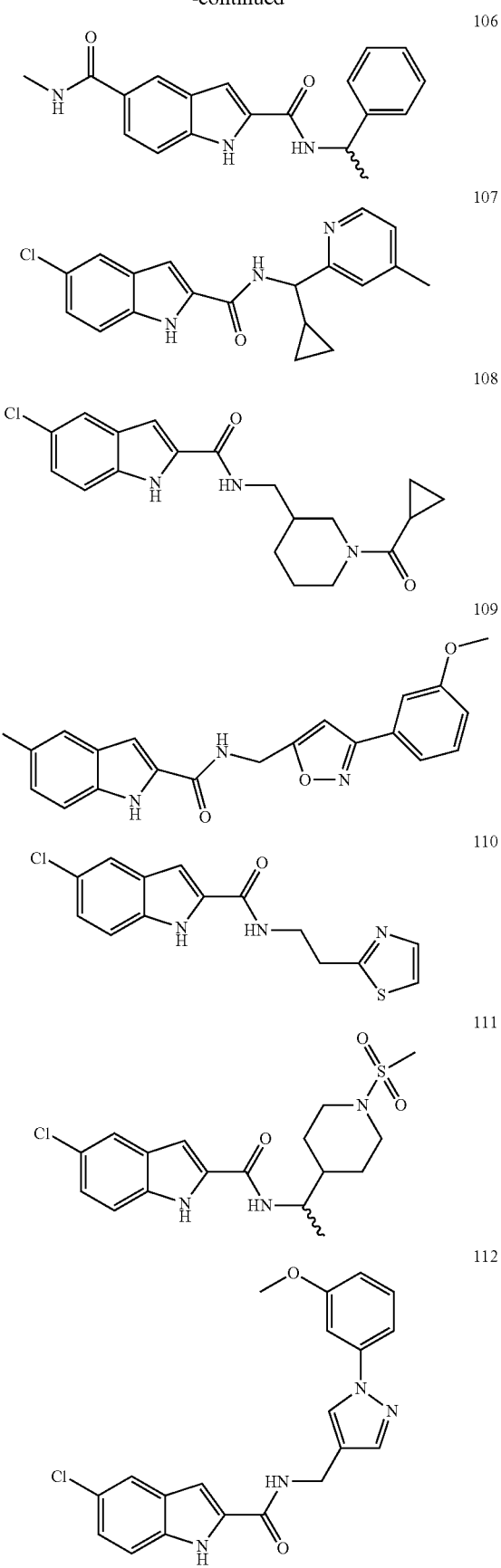

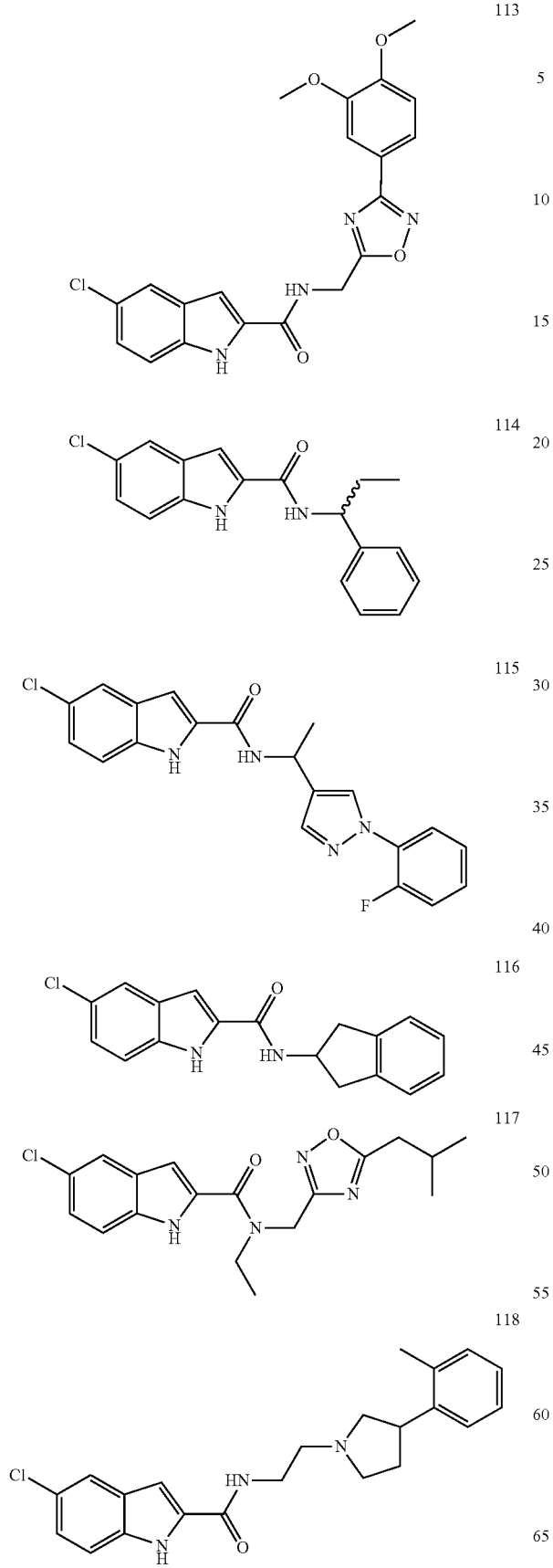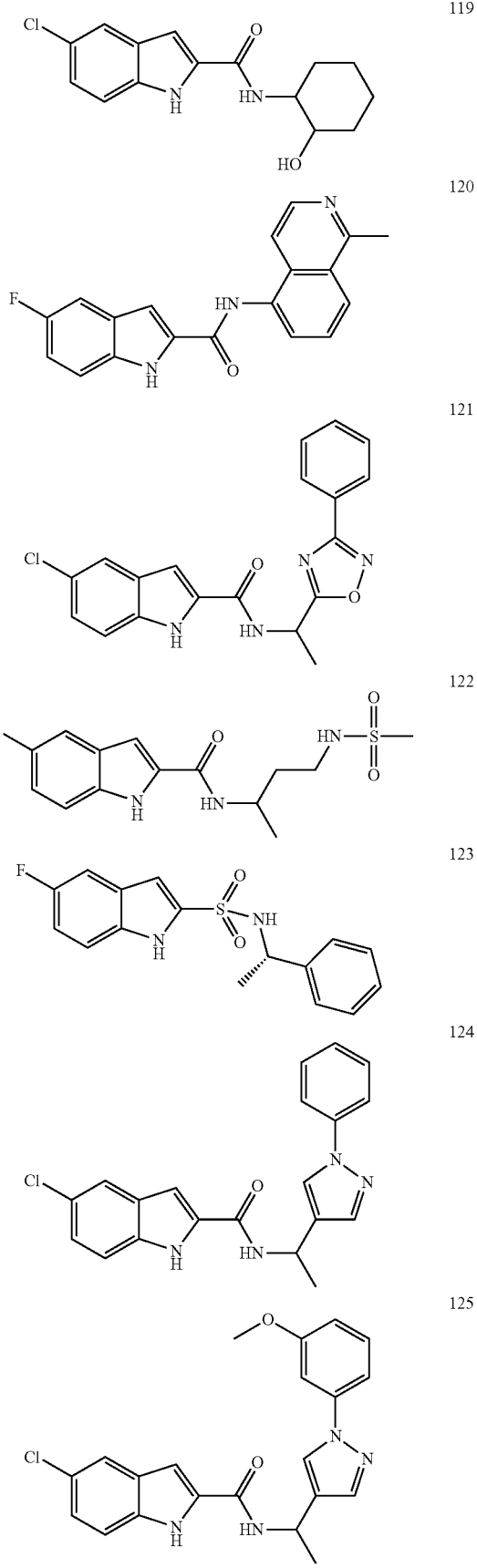

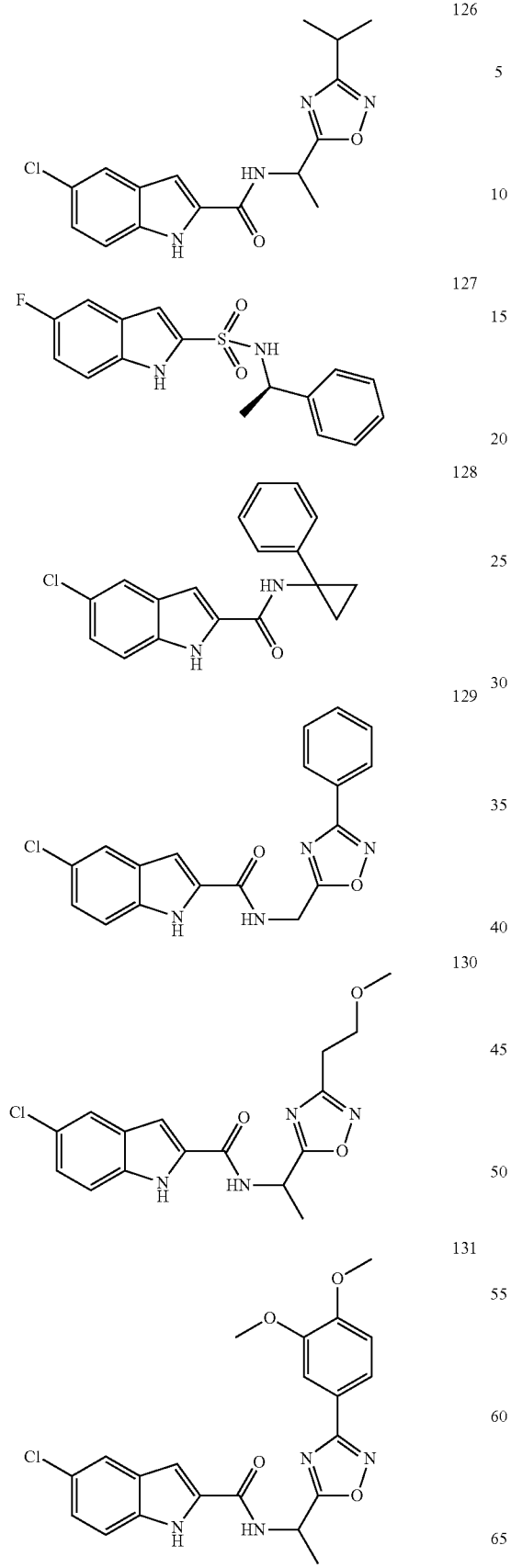
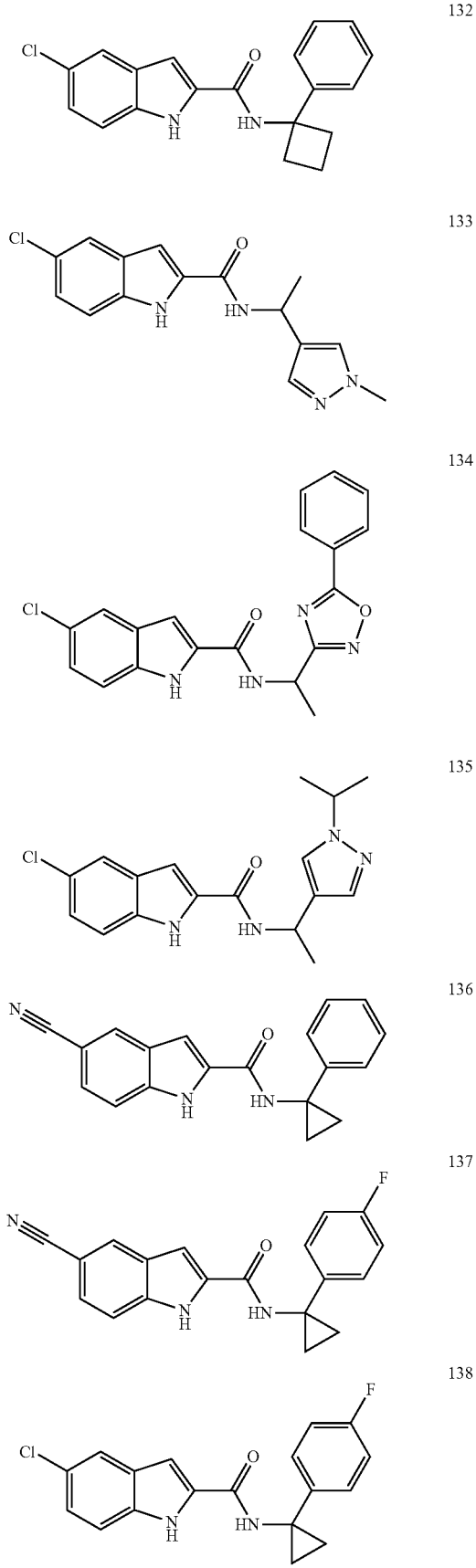

139 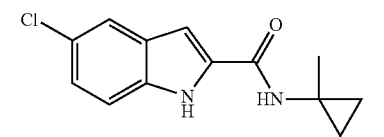
140 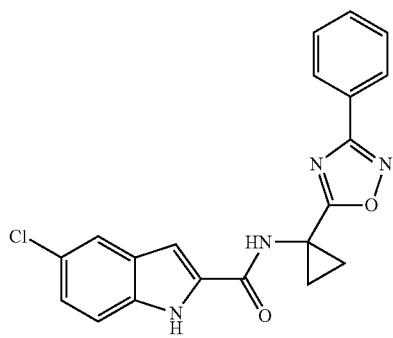
141 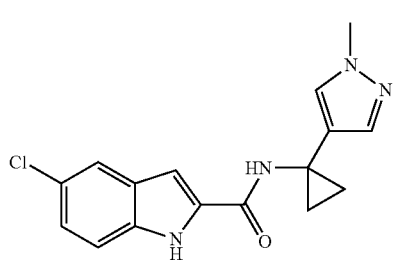
142 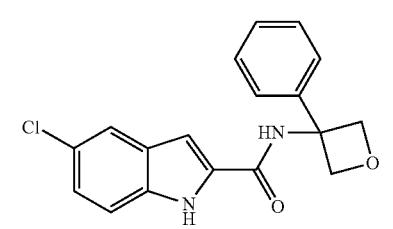
143 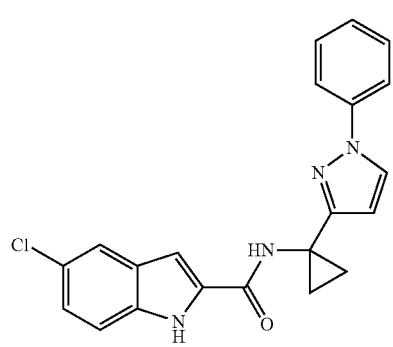
144 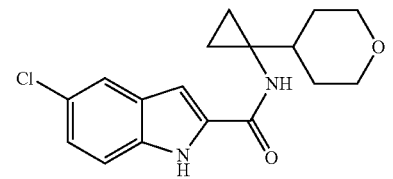
145 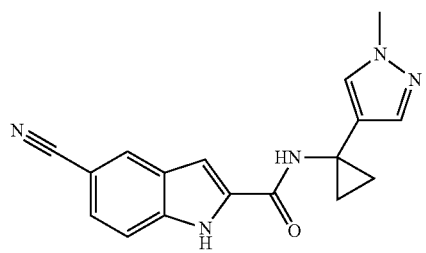
146 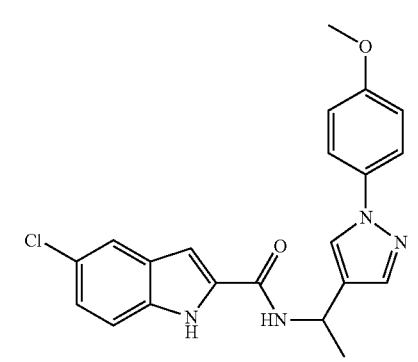
147 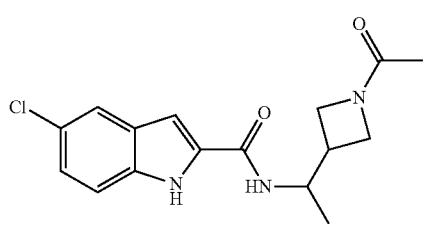
148 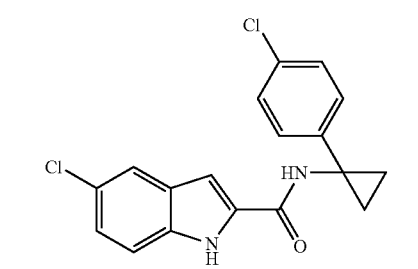
149 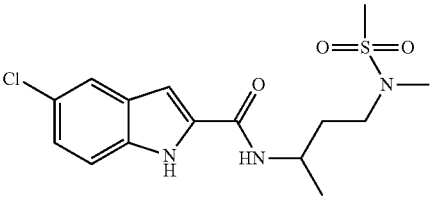
150 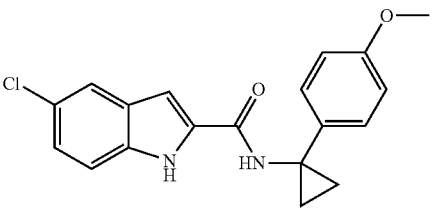

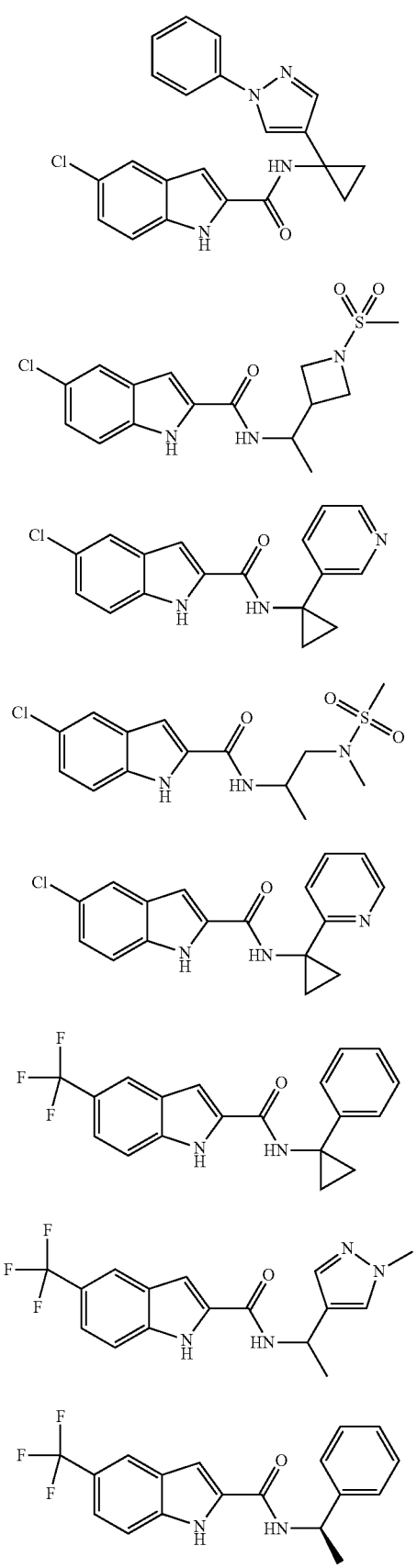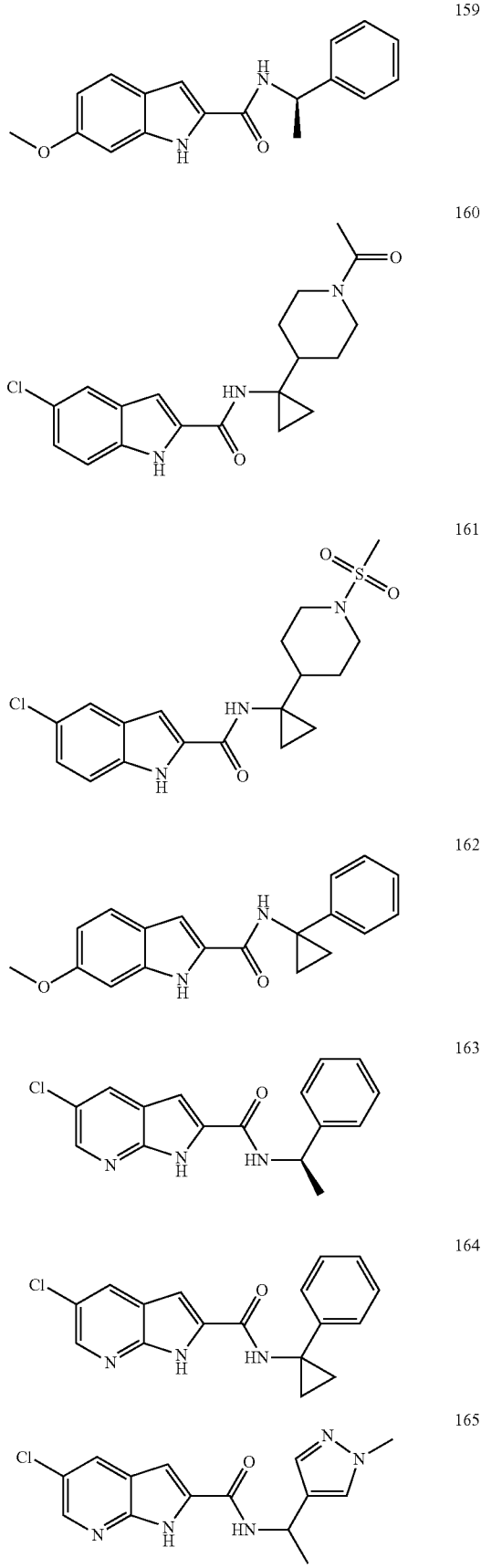

-continued
166 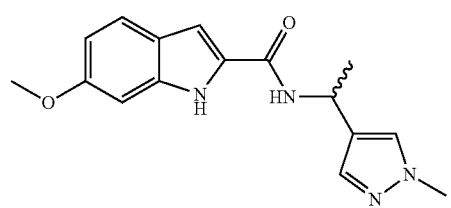
167 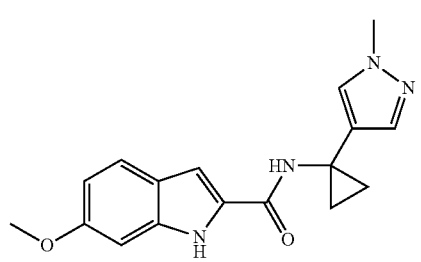
168 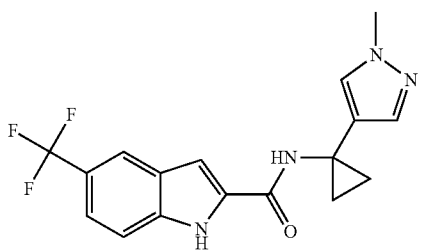
169 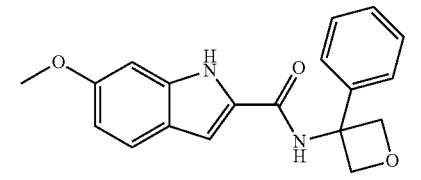
170 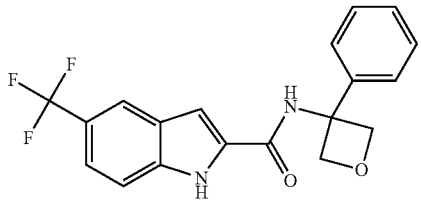
171 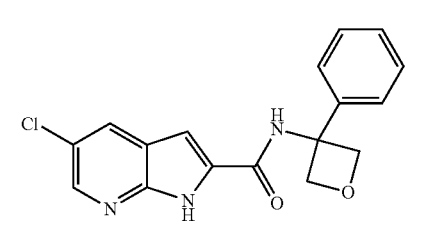
172 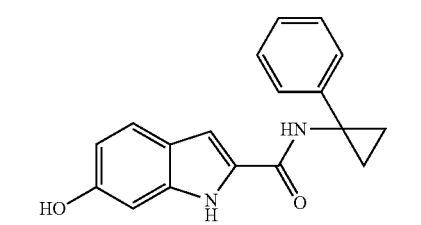
-continued
173 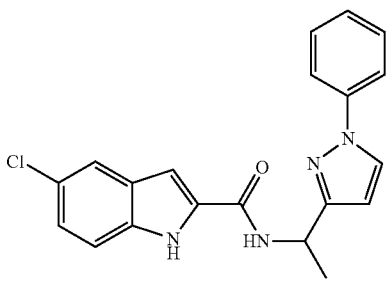
174 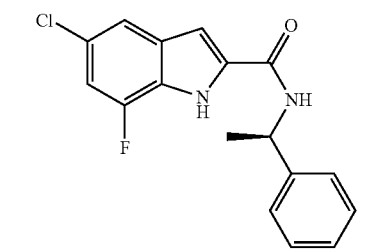
175 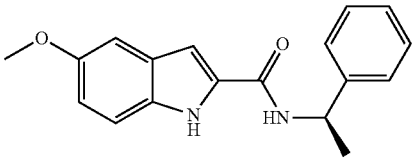
176 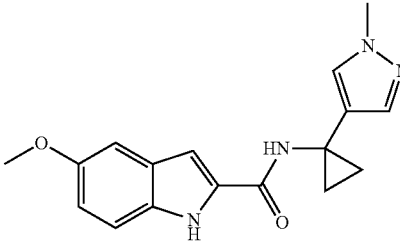
177 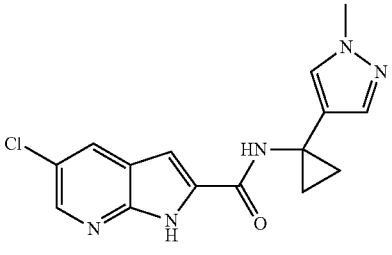
178 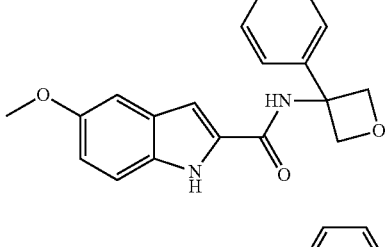
179 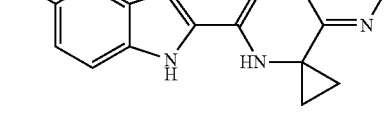

180 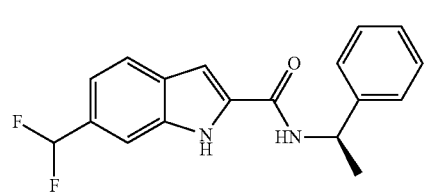
181 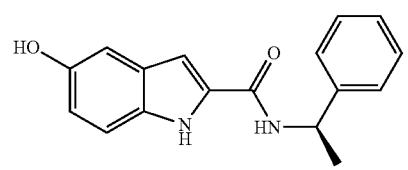
182 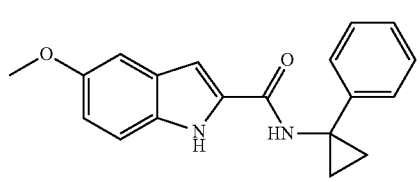
183 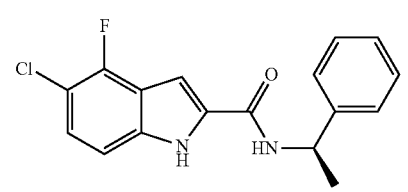
184 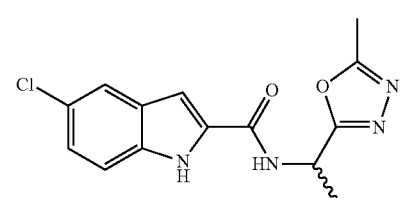
185 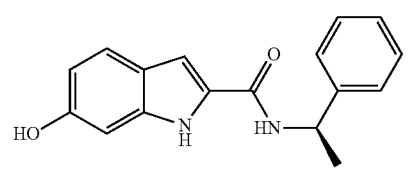
186 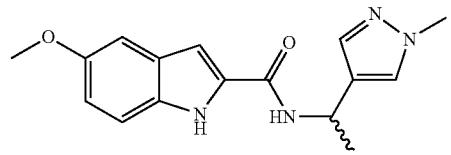
187 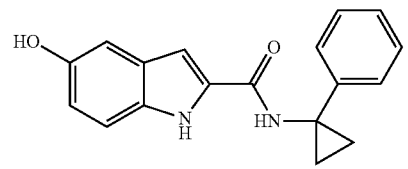
188 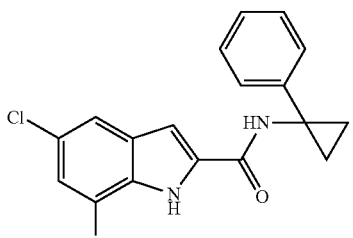
189 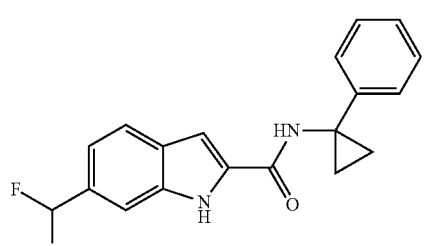
190 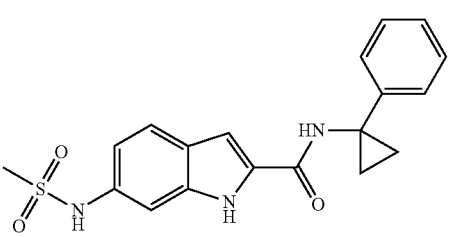
191 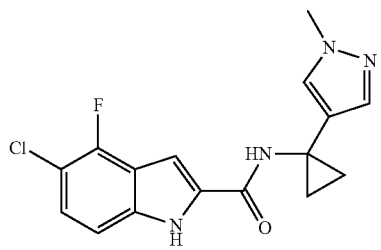
192 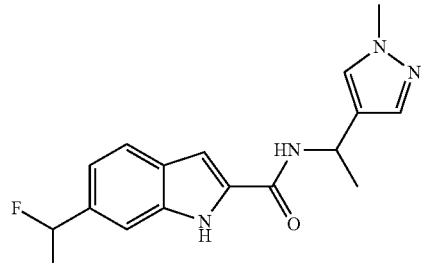
193 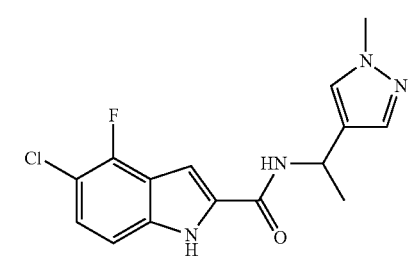

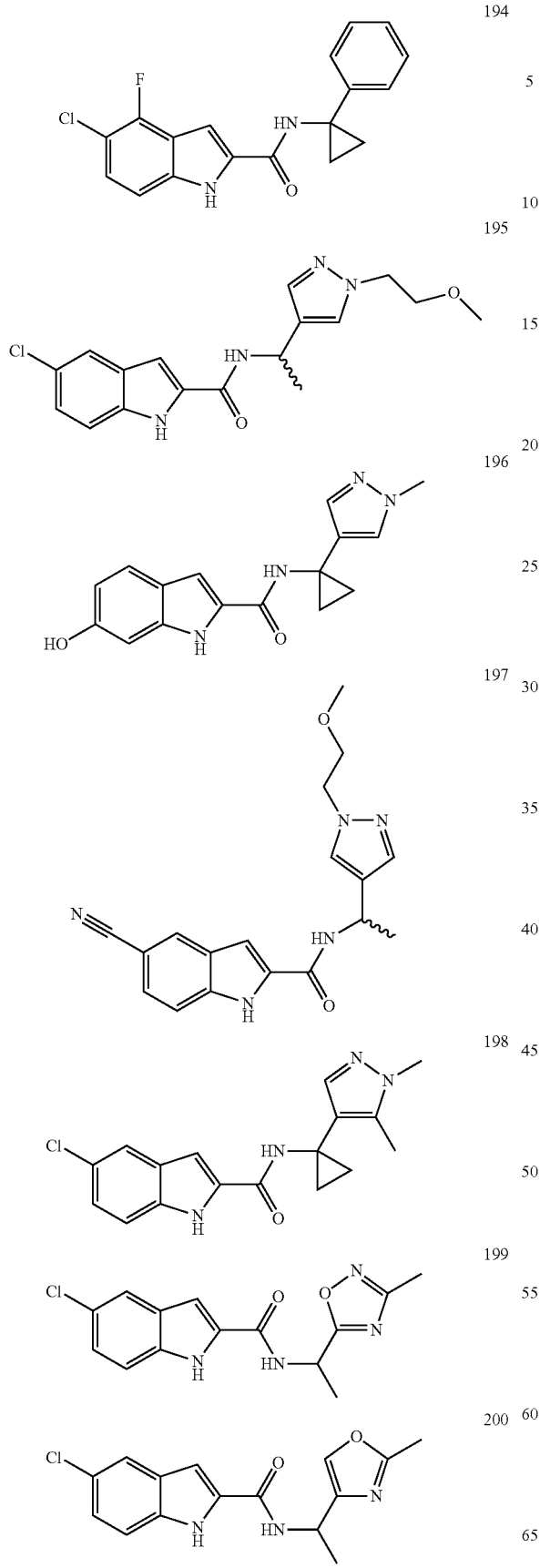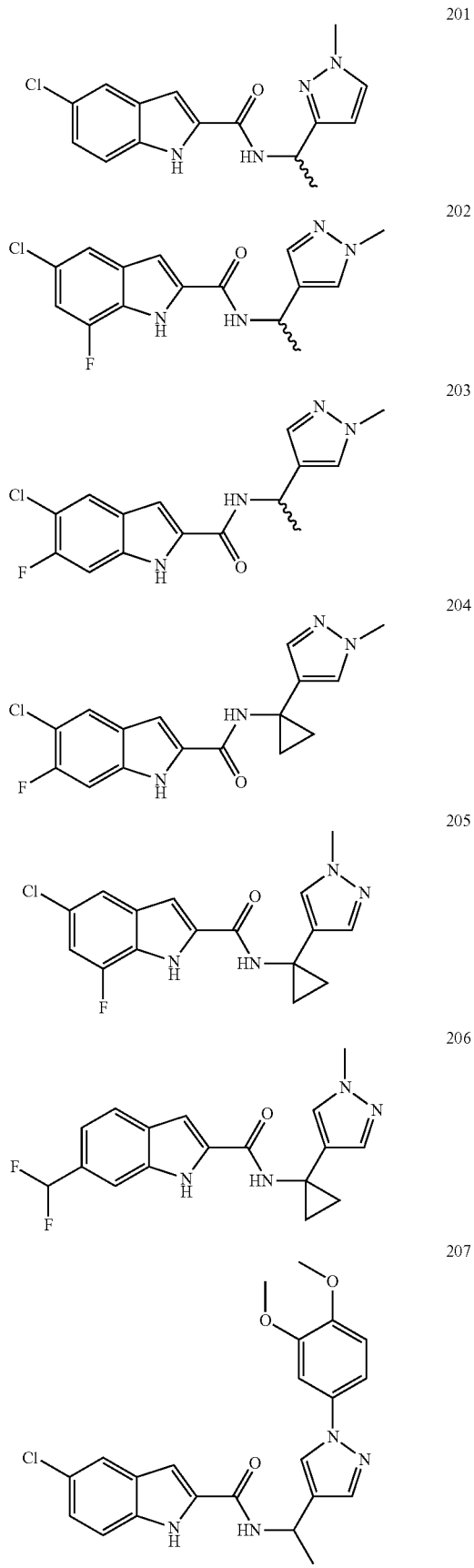

208 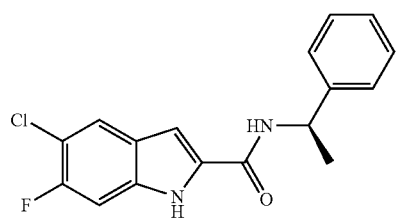
209 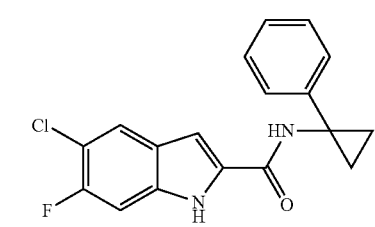
210 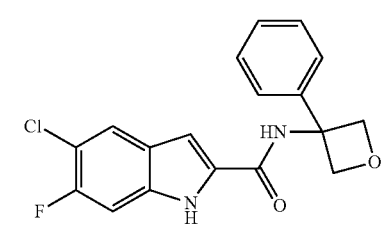
211 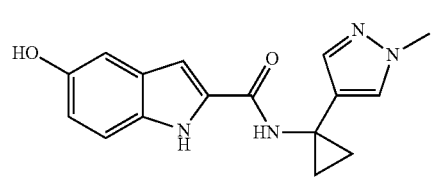
212 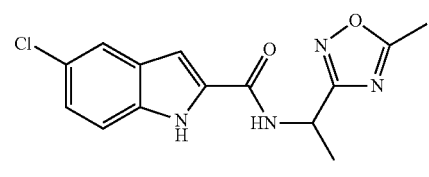
213 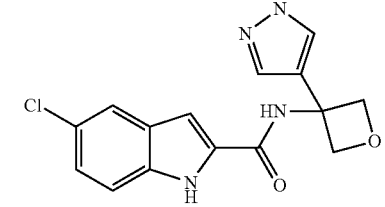
214 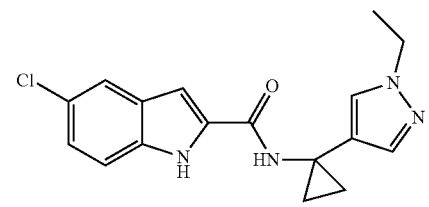
215 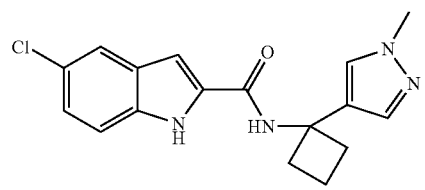
216 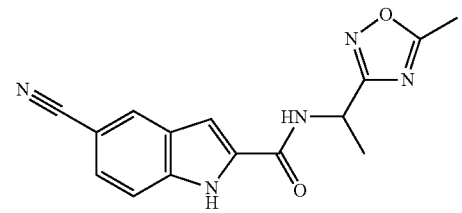
217 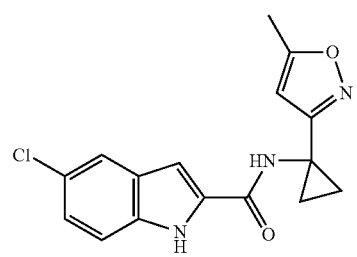
218 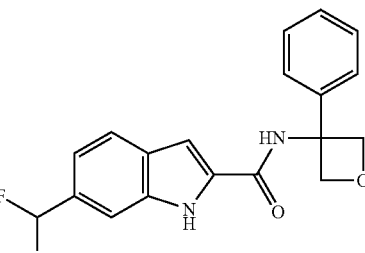
219 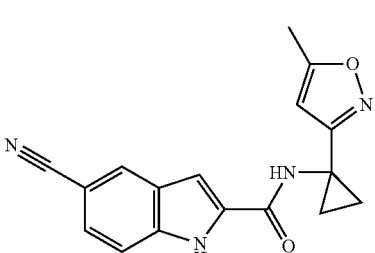
220 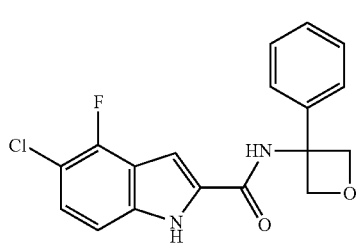
221 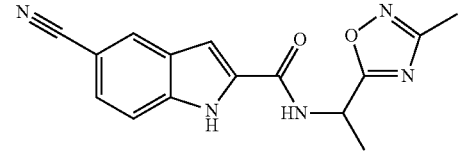

222 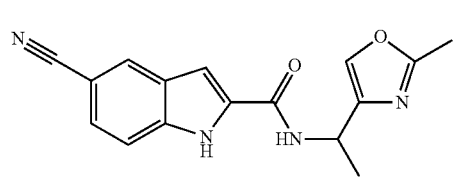
223 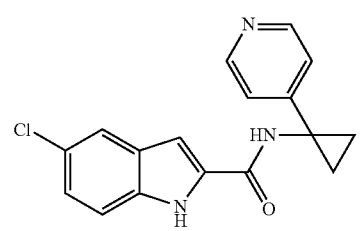
224 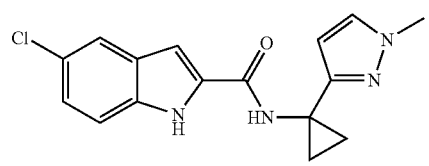
225 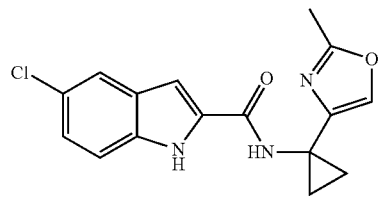
226 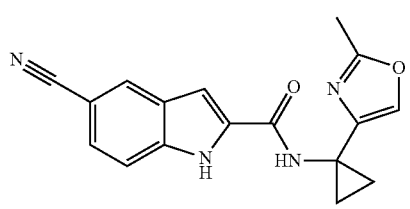
227 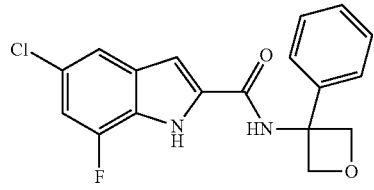
228 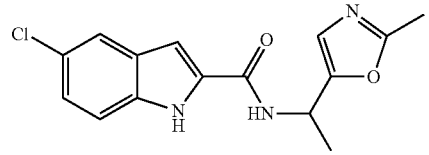
229 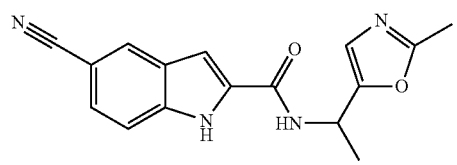
230 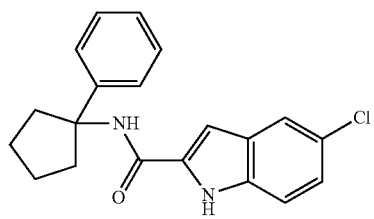
231 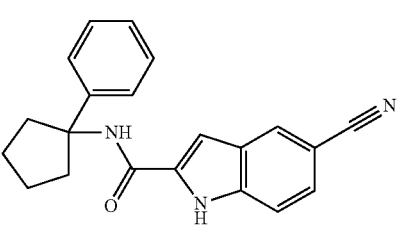
232 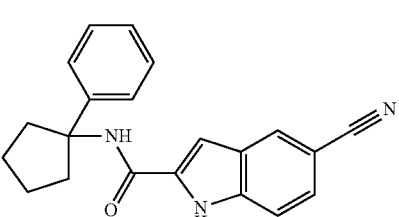
233 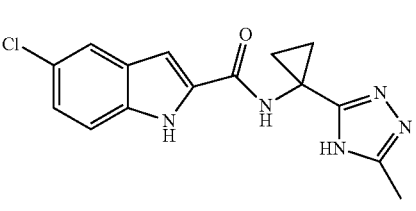
234 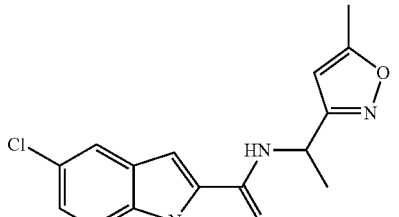
235 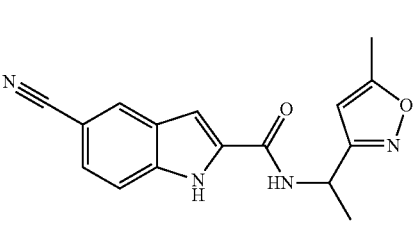
236 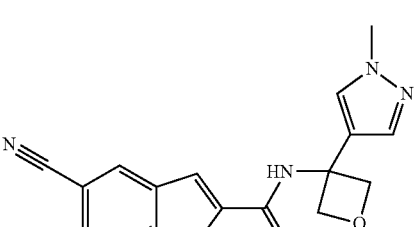

237 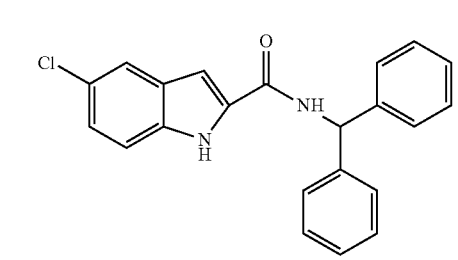
238 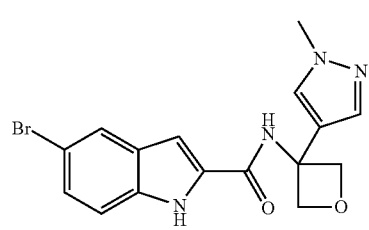
239 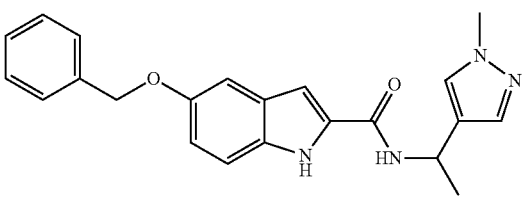
240 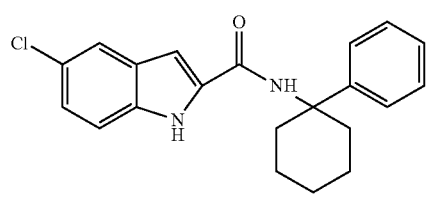
241 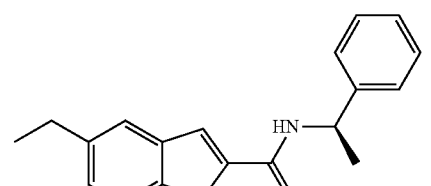
242 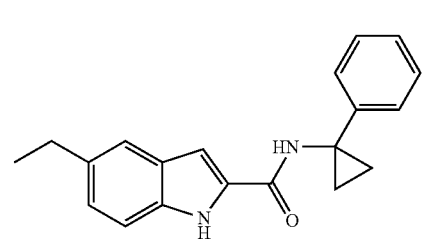
243 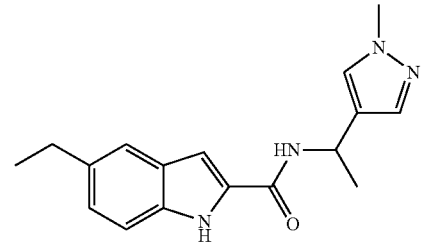
244 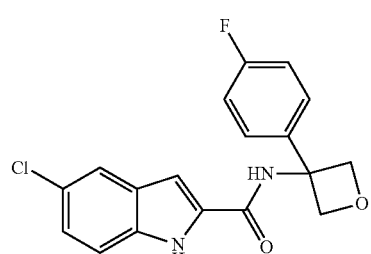
245 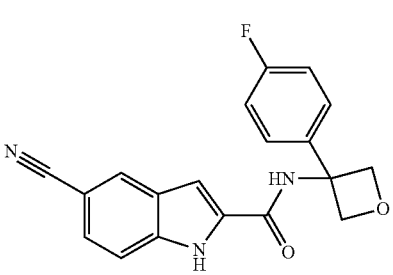
246 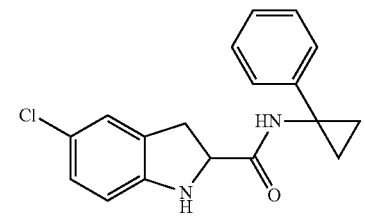
247 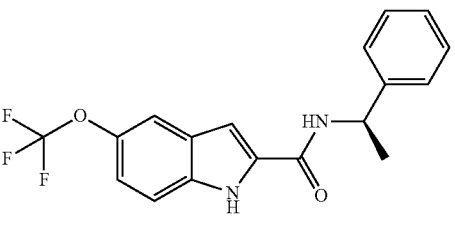
248 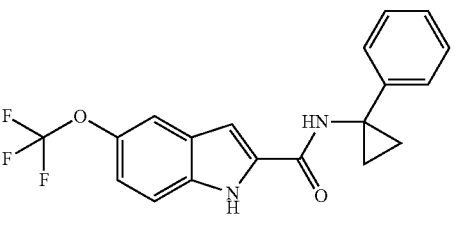
249 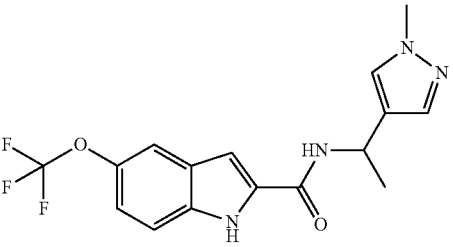
250 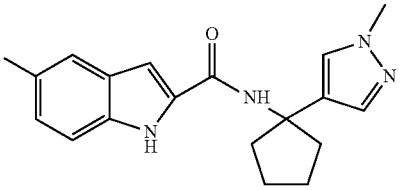

-continued
| | |
|---|---|
| 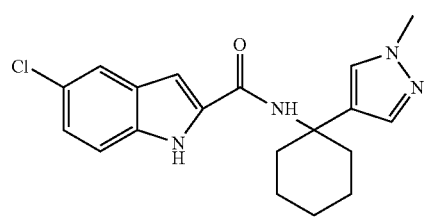 | 251 |
| 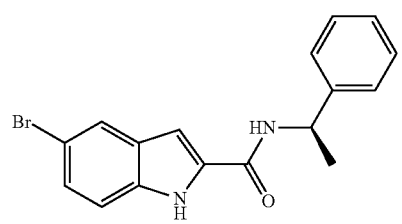 | 252 |
| 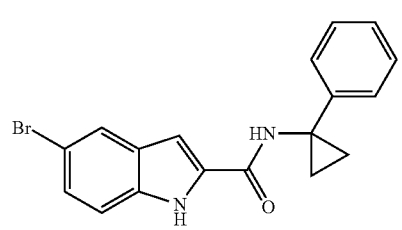 | 253 |
| 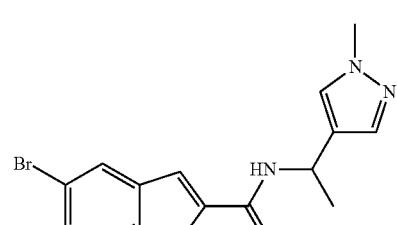 | 254 |
| 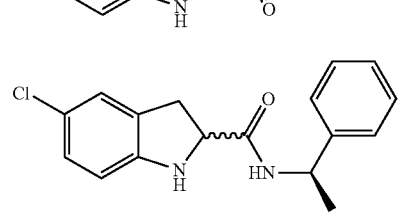 | 255 |
| 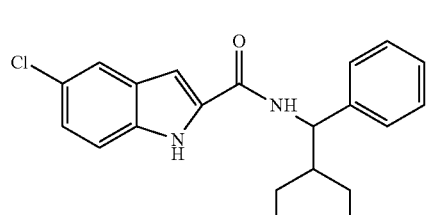 | 256 |
| 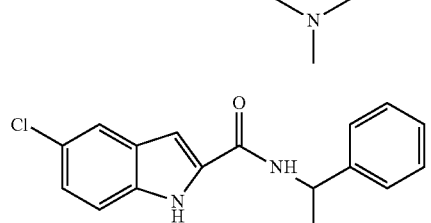 | 257 |
-continued
| | |
|---|---|
| 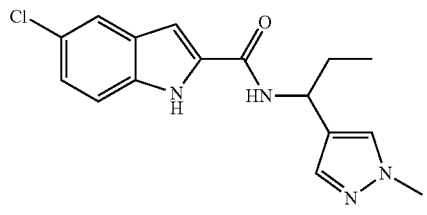 | 258 |
| 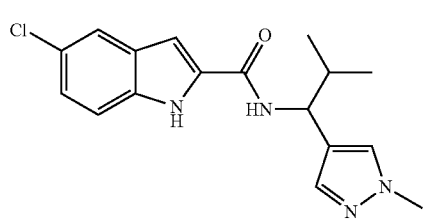 | 259 |
| 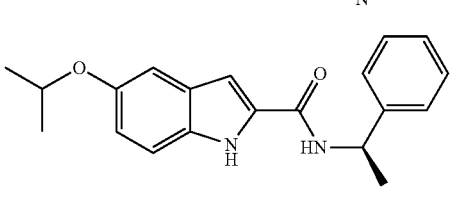 | 260 |
| 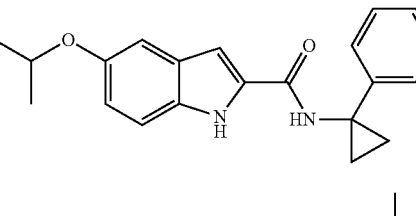 | 261 |
| 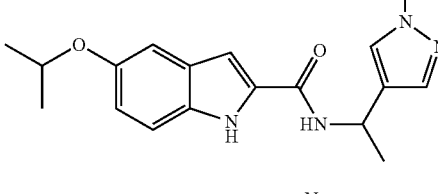 | 262 |
| 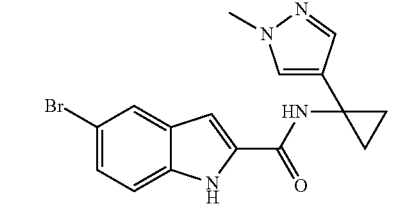 | 263 |
| 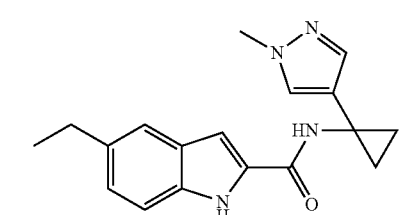 | 264 |
| 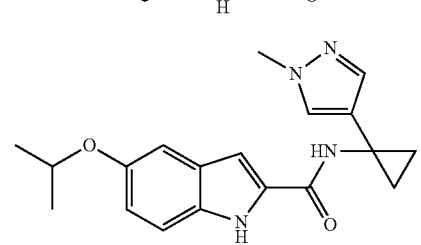 | 265 |

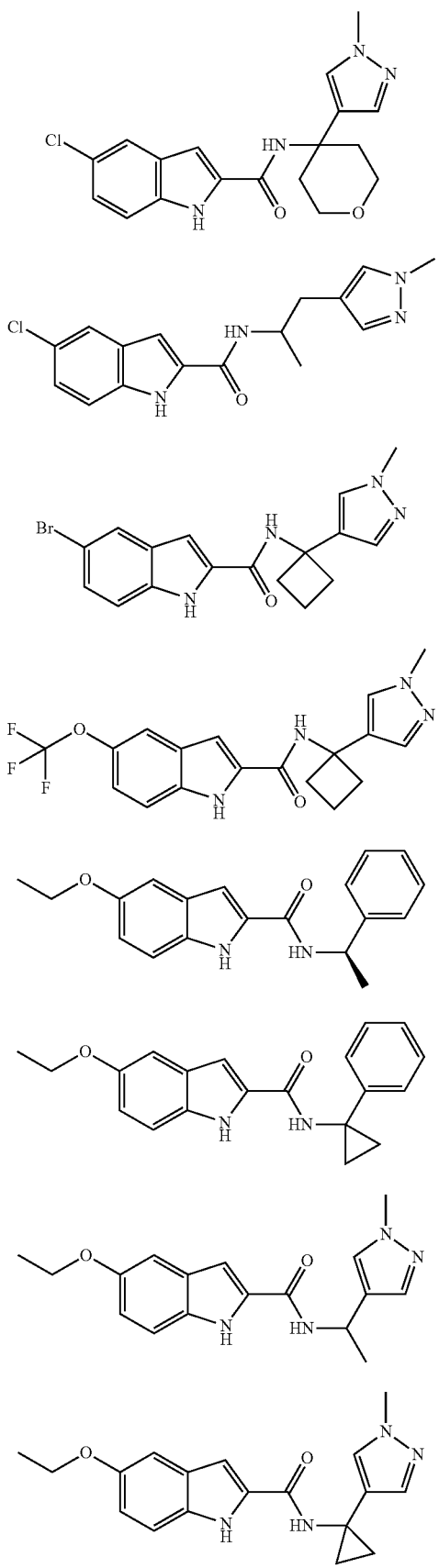

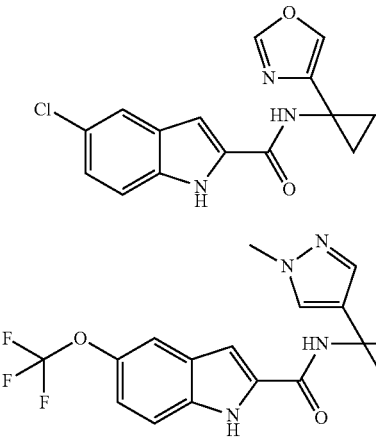

In the above compounds, where stereochemistry is indicated at a chiral centre, the invention also includes both of the possible isolated enantiomers and also the racemic mixture. In addition, where a racemic mixture is indicated at a chiral centre (such as by a wavy line) the invention also includes both isolated enantiomers and the racemic mixture. Further, where no stereochemistry is given at a chiral centre the invention also includes both isolated enantiomers and the racemic mixture. Thus, the compounds of the present invention extend to isolated enantiomers, and/or a mixture of two or more enantiomers, and/or a mixture of two or more diastereomers (e.g. where there is more than one chiral centre), and/or a mixture of two or more epimers, and/or racemic mixtures. In addition to this, the above formulae (and all formulae herein) are intended to represent all tautomeric forms equivalent to the corresponding formula.

In the context of the present invention, the medicinal use is not especially limited, provided that it is a use which is facilitated by the TDO and/or the IDO inhibitory effect of the compound. Thus, the compounds of the invention may be for use in any disease, condition or disorder that may be prevented, ameliorated or treated using a TDO and/or IDO inhibitor. Typically this comprises a disease condition and/or a disorder selected from: a cancer, an inflammatory condition, an infectious disease, a central nervous system disease or disorder, coronary heart disease, chronic renal failure, post anaesthesia cognitive dysfunction, a disease condition and/or a disorder relating to female reproductive health including contraception or abortion, and cataracts.

When the disease, condition or disorder is an inflammatory disease, condition or disorder, it is not especially limited, provided that the disease, condition or disorder is one which may be treated, prevented or ameliorated by using a TDO and/or IDO inhibitor. However, typically the inflammatory condition is a condition relating to immune B cell, T cell, dendritic cell, natural killer cell, macrophage, and/or neutrophil dysregulation.

When the disease, condition or disorder is a cancer, it is not especially limited, provided that the cancer is one which may be treated, prevented or ameliorated by using a TDO and/or IDO inhibitor. Thus the cancer may be a cancer selected from: a solid or liquid tumour including cancer of the eye, brain (such as gliomas, glioblastomas, medullablastomas, craniopharyngioma, ependymoma, and astrocytoma), spinal cord, kidney, mouth, lip, throat, oral cavity, nasal cavity, small intestine, colon, parathyroid gland, gall bladder, head and neck, breast, bone, bile duct, cervix, heart, hypopharyngeal gland, lung, bronchus, liver, skin, ureter, urethra, testicles, vagina, anus, laryngeal gland, ovary, thyroid, oesophagus, nasopharyngeal gland, pituitary gland, salivary gland, prostate, pancreas, adrenal glands; an endometrial cancer, oral cancer, melanoma, neuroblastoma, gastric cancer, an angiomatosis, a hemangioblastoma, a pheochromocytoma, a pancreatic cyst, a renal cell carcinoma, Wilms' tumour, squamous cell carcinoma, sarcoma, osteosarcoma, Kaposi sarcoma, rhabdomyosarcoma, hepatocellular carcinoma, PTEN Hamartoma-Tumor Syndromes (PHTS) (such as Lhermitte-Duclos disease, Cowden syndrome, Proteus syndrome, and Proteus-like syndrome), leukaemias and lymphomas (such as acute lymphoblastic leukaemia, chronic lymphocytic leukaemia, acute myelogenous leukaemia, chronic myelogenous leukaemia, hairy cell leukaemia, T-cell prolymphocytic leukemia (T-PLL), large granular lymphocytic leukemia, adult T-cell leukemia, juvenile myelomonocytic leukaemia, Hodgkin lymphoma, non-Hodgkin lymphoma, mantle lymphoma, follicular lymphoma, primary effusion lymphoma, AIDS-related lymphoma, Hodgkin lymphoma, diffuse B cell lymphoma, Burkitt lymphoma, and cutaneous T-cell lymphoma). However, when the compound is an IDO inhibitor, typically (but not exclusively) the cancer is a cancer selected from acute myeloid leukemia (AML), a small-cell lung cancer, a melanoma, an ovarian cancer, a colorectal cancer, a pancreatic cancer, an endometrial cancer, and a skin papilloma. When the compound is a TDO inhibitor, typically (but not exclusively) the cancer is a cancer selected from a glioma, and a hepatocellular carcinoma.

When the disease is an infectious disease, it is not especially limited, provided that the disease is one which may be treated, prevented or ameliorated by using a TDO and/or IDO inhibitor. However, typically the infectious disease is selected from a bacterial infection and a viral infection, preferably a gut infection, sepsis, sepsis induced hypotension, HIV infection and HCV infection.

When the disease, condition or disorder is a central nervous system disease, condition or disorder, it is not especially limited, provided that the disease, condition or disorder is one which may be treated, prevented or ameliorated by using a TDO and/or IDO inhibitor. However, the central nervous system disease, condition or disorder is typically selected from amyotrophic lateral sclerosis (ALS), Huntington's disease, Alzheimer's disease, pain, a psychiatric disorder, multiple sclerosis, Parkinson's disease, and HIV related neurocognitive decline.

When the disease, condition or disorder is one relating to female reproductive health, it is not especially limited provided that the disease, condition or disorder is one which may be treated, prevented or ameliorated by using a TDO and/or IDO inhibitor. In typical embodiments the disease, condition or disorder is selected from gynaecological disorders such as endometriosis. Conditions relating to female reproductive health that are included in the invention include contraception and abortion such that the compounds of the invention may be used as a contraceptive and/or abortive agent.

The present invention also provides a pharmaceutical composition comprising a compound as defined above. Whilst the pharmaceutical composition is not especially limited, typically the composition further comprises a pharmaceutically acceptable additive and/or excipient. In the pharmaceutical composition, the compound as defined above may be present in the form described above, but may alternatively be in a form suitable for improving bioavailability, solubility, and/or activity, and/or may be in a form suitable for improving formulation. Thus, the compound may be in the form of a pharmaceutically acceptable salt, hydrate, acid, ester, or other alternative suitable form. Typically, the composition is for treating a disease, condition or disorder as defined above. In some instances, the compound may be present in the composition as a pharmaceutically acceptable salt, or other alternative form of the compound, in order to ameliorate pharmaceutical formulation.

In some embodiments the pharmaceutical composition is a composition for treating a cancer, further comprising a further agent for treating cancer. The further agent for treating cancer is not especially limited, provided that it affords some utility for cancer treatment. However, typically the further agent for treating cancer is selected from anti-microtubule agents, platinum coordination complexes, alkylating agents, antibiotic agents, topoisomerase II inhibitors, antimetabolites, topoisomerase I inhibitors, hormones and hormone analogues, signal transduction pathway inhibitors, non-receptor tyrosine kinase angiogenesis inhibitors, immunotherapeutic agents, proapoptotic agents and cell cycle signalling inhibitors. An immunotherapeutic agent may consist of but is not limited to an anti-tumour vaccine, an oncolytic virus, an immune stimulatory antibody such as anti-CTLA4, anti-PD1, anti-PDL-1, anti-OX40, anti-41BB, anti-CD27, anti-anti-CD40, anti-LAG3, anti-TIM3, and anti-GITR, a novel adjuvant, a peptide, a cytokine, a chimeric antigen receptor T cell therapy (CAR-T), a small molecule immune modulator, tumour microenvironment modulators, and anti-angiogenic agents.

Further provided by the invention is a method of treating a disease and/or a condition and/or a disorder, which method comprises administering to a patient a compound or a composition as defined above. The method is typically a method for treating any disease condition or disorder mentioned herein. In typical embodiments, the method is a method for treating a cancer. Preferably such a method comprises administering to a patient a compound or a composition as defined above and a further agent for treating cancer as defined above. The compound or composition and the further agent may administered simultaneously, sequentially or separately, depending upon the agents and patients involved, and the type of cancer indicated.

Typically, in all embodiments of the invention, both above and below, the patient is an animal, typically a mammal, and more typically a human.

Further provided by the invention is a method of synthesis of a compound as defined above, which method comprises a step of substituting the substituent (typically an H group) at the 2-position of a substituted or unsubstituted indole or azaindole compound, or a part thereof (typically when an amide or other coupling reaction is performed) with a different substituent, and/or performing a coupling reaction (such as an amide coupling reaction) on a substituent in the 2-position.

In addition to compounds for use in medicine, the present invention, and in particular the synthetic method, provides compounds that were not previously known, such compounds comprising a formula selected from one of the following:

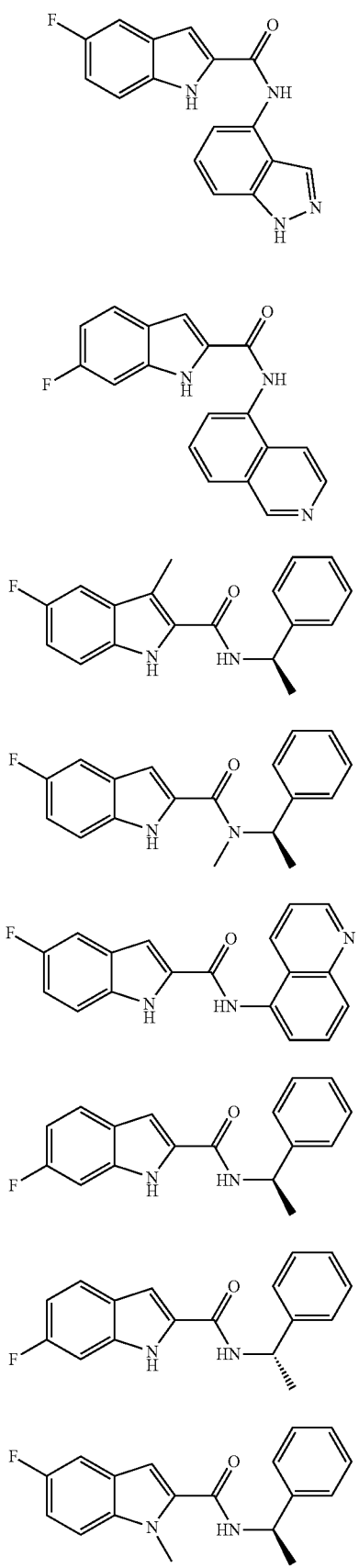
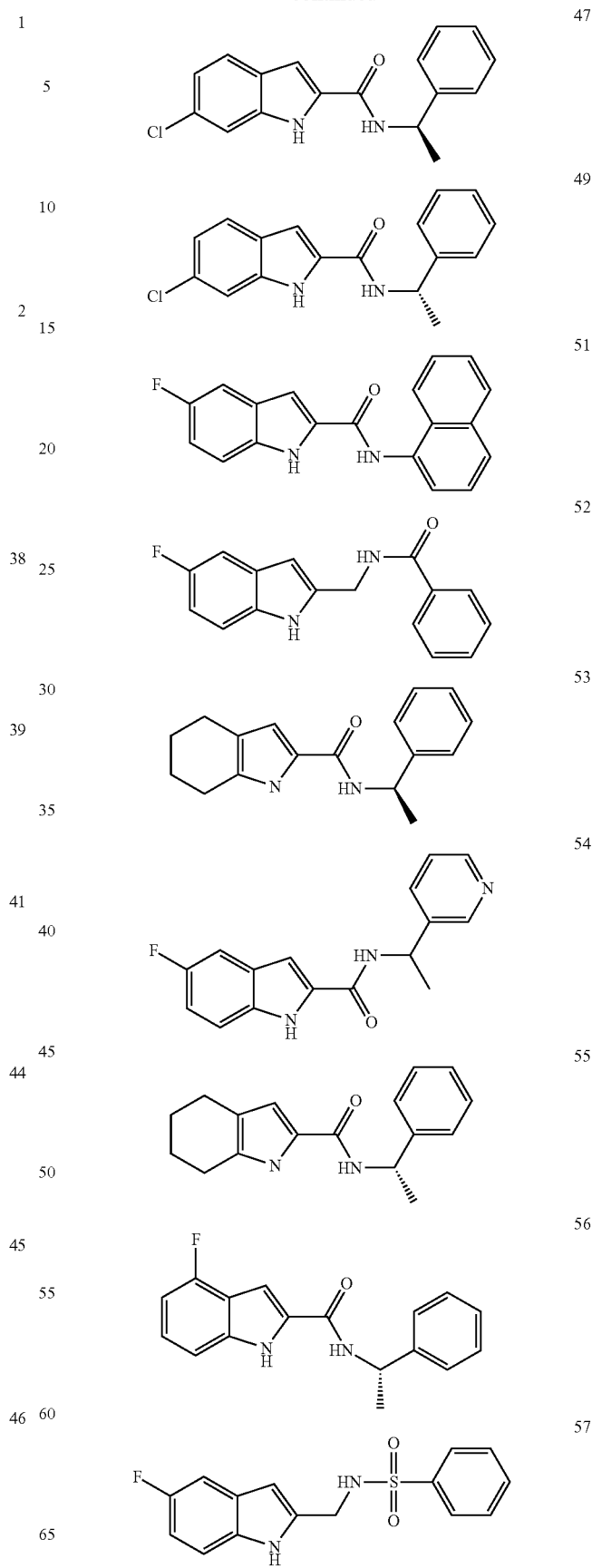

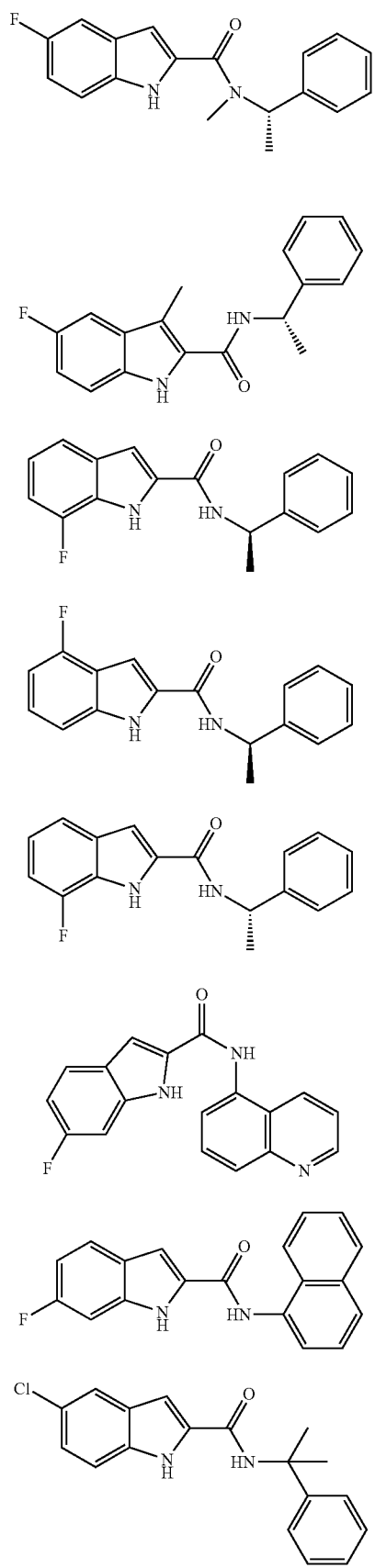
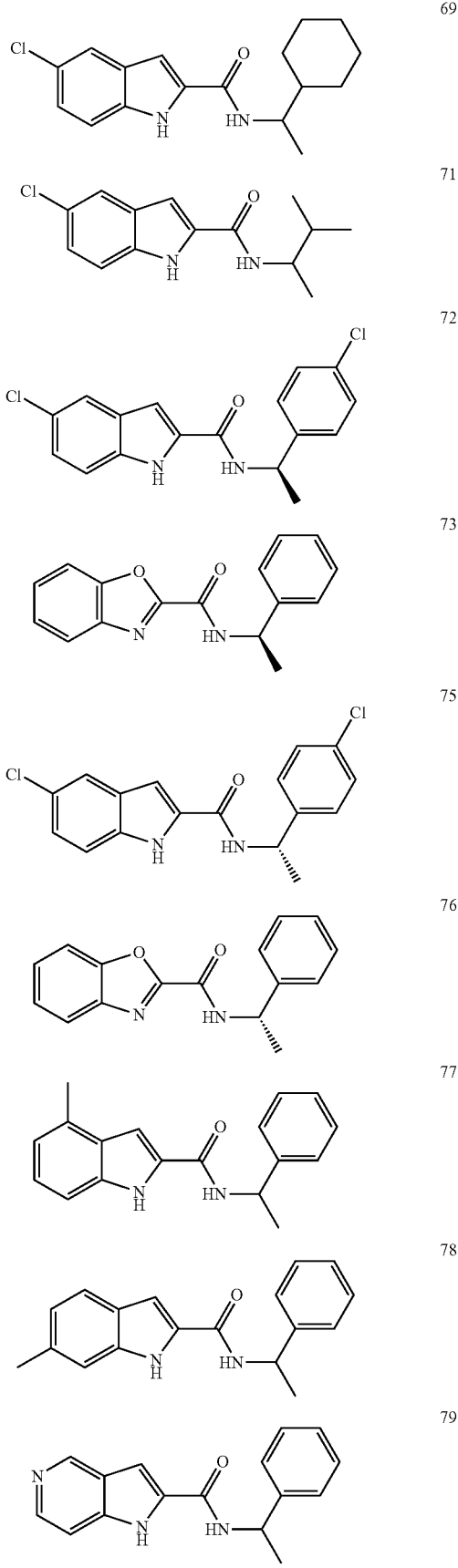

-continued
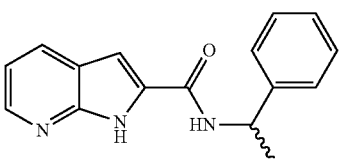
80
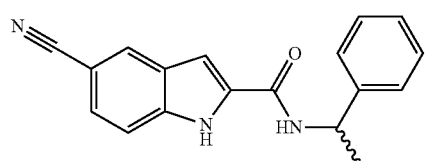
82
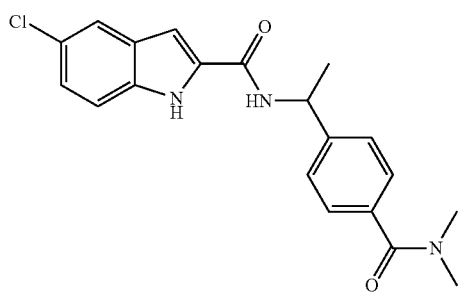
83
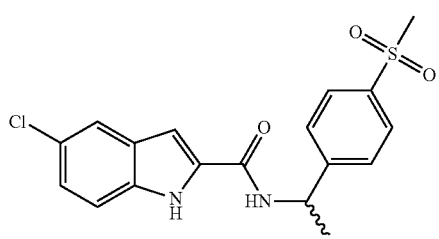
84
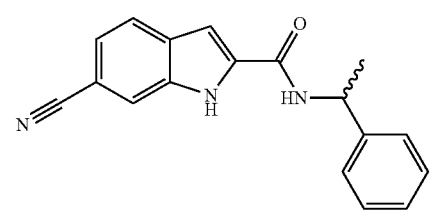
85
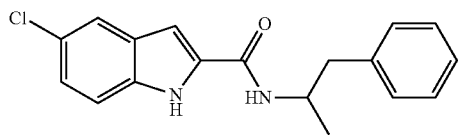
86
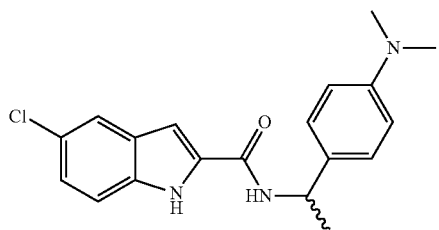
87
-continued
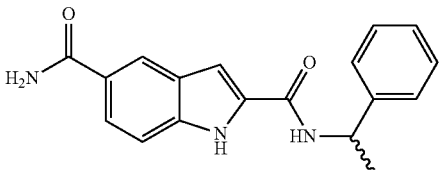
88
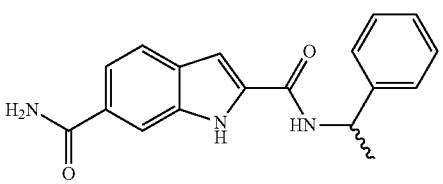
89
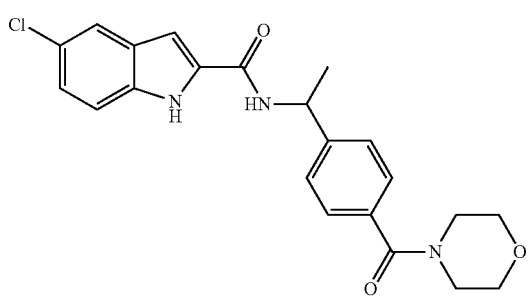
90
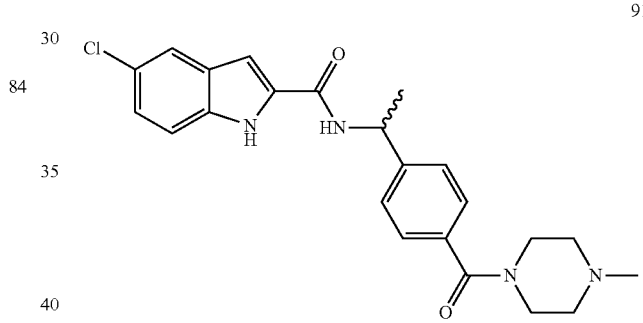
91
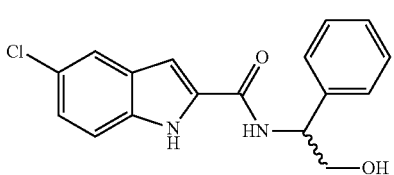
92
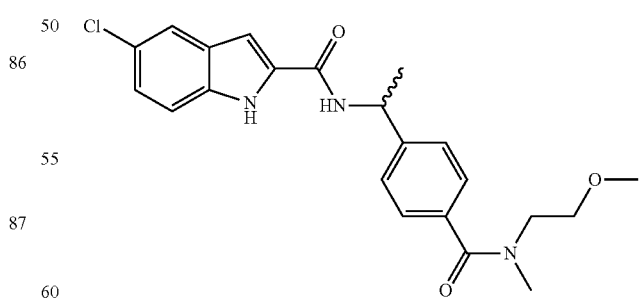
93
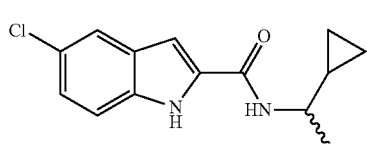
94

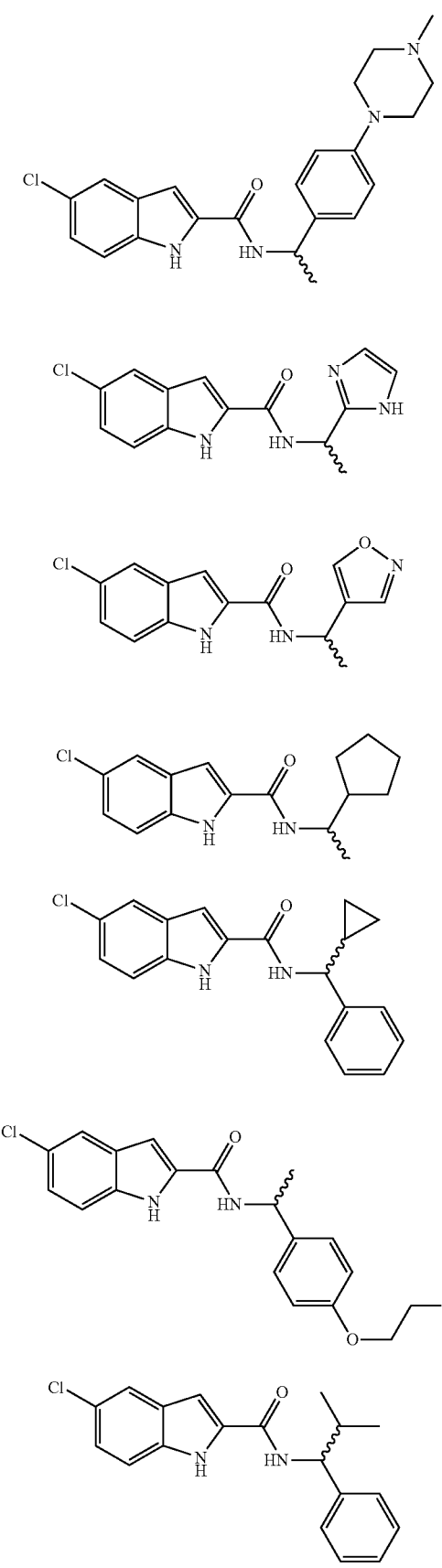
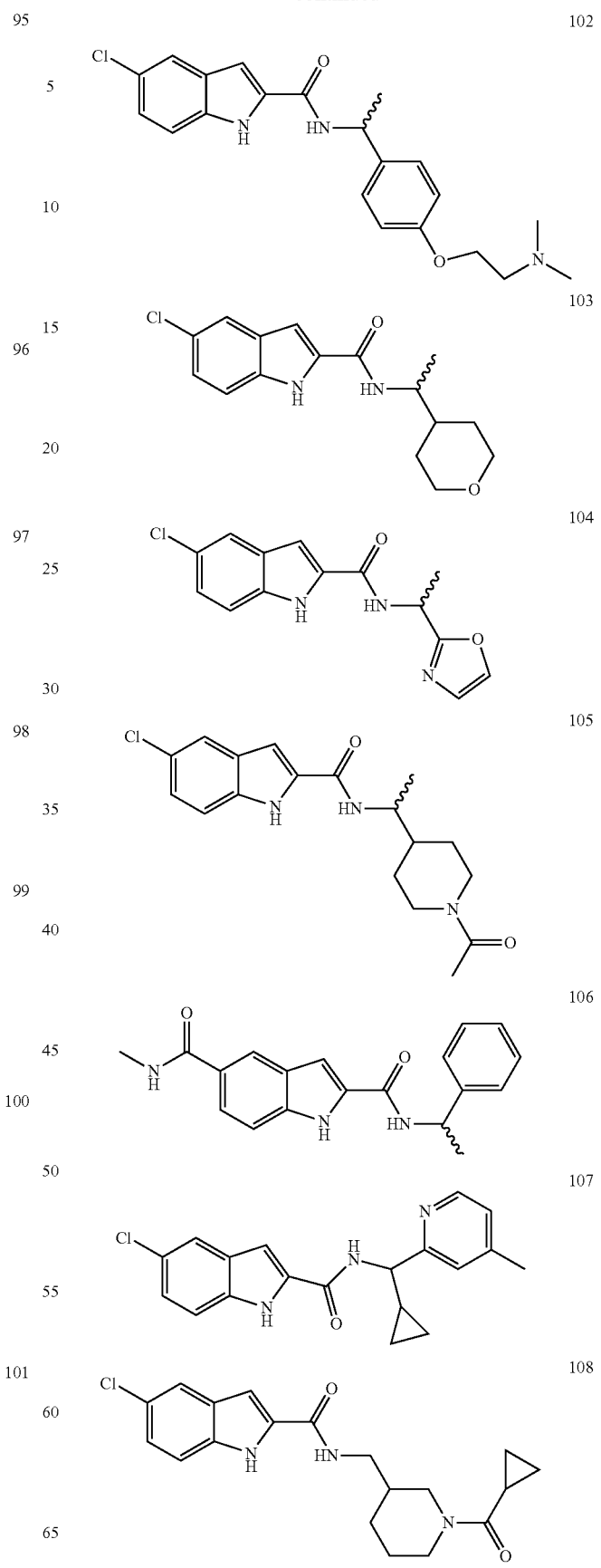

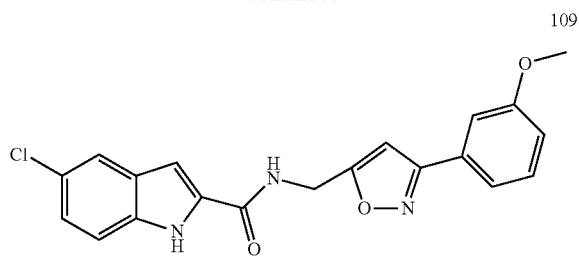
109
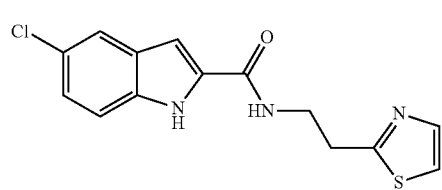
110
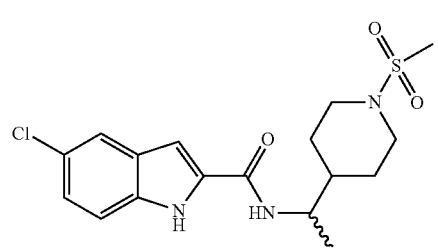
111
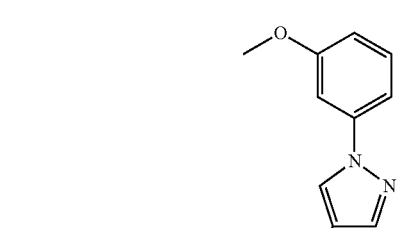
112
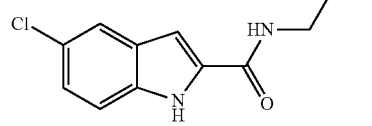
113
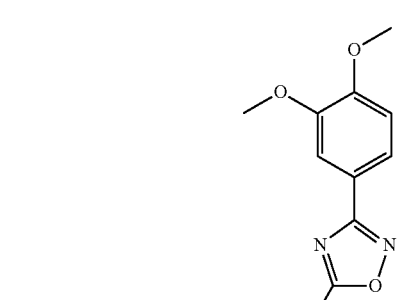
114
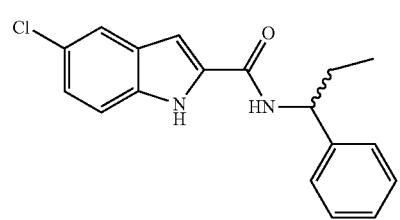
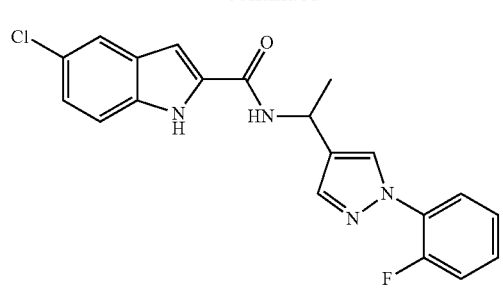
115
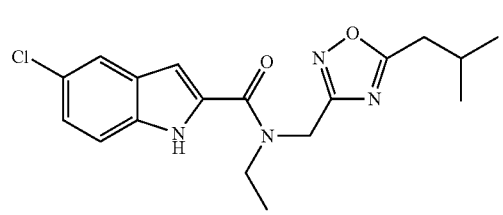
117
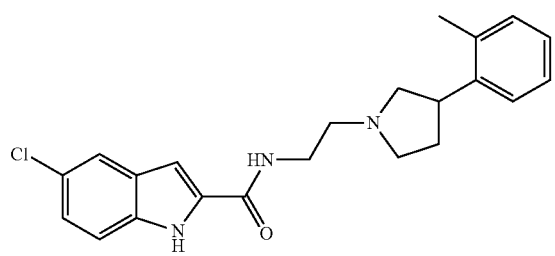
118
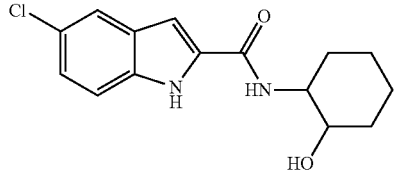
119
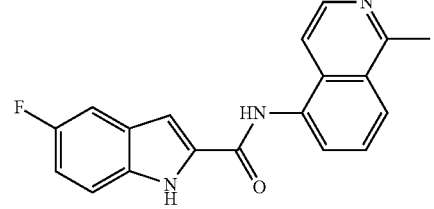
120
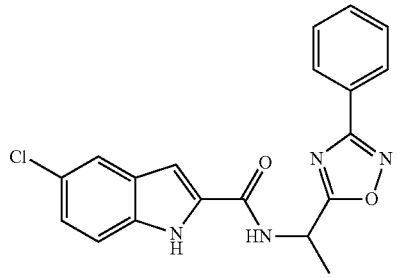
121
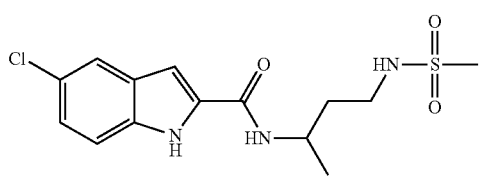
122

123
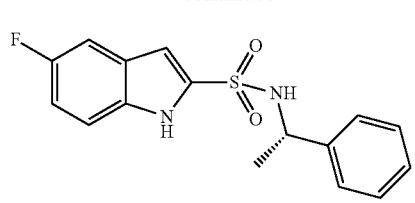
124
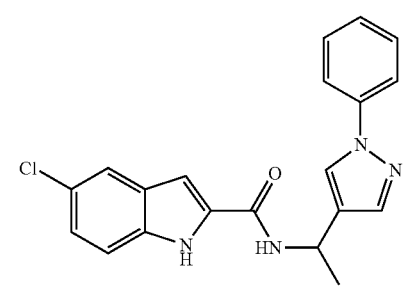
125
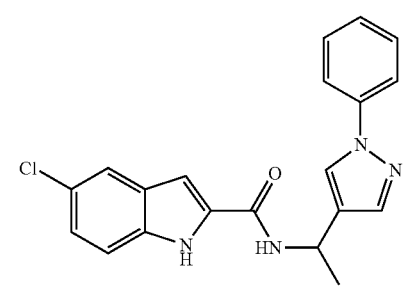
126
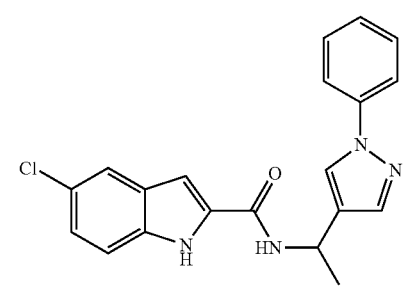
127
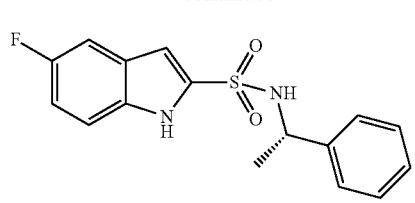
128
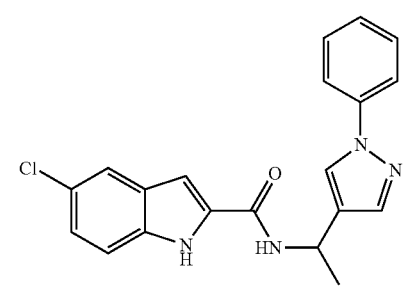
129
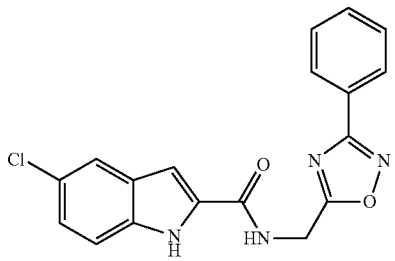
130
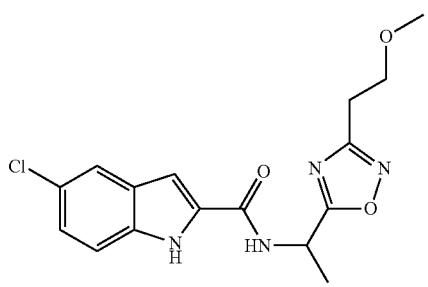
131
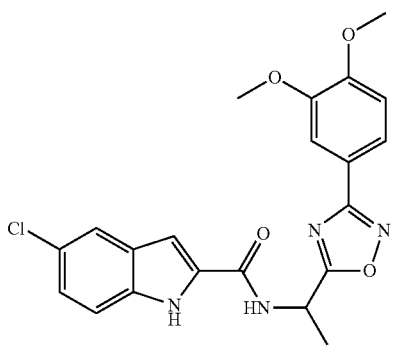
132
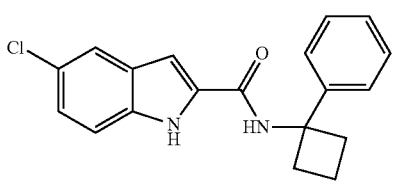
133
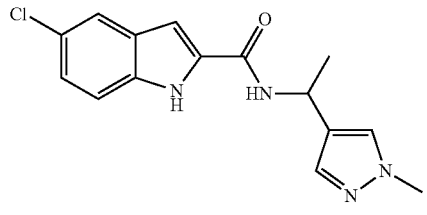
134
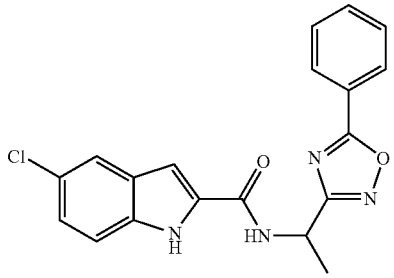

135 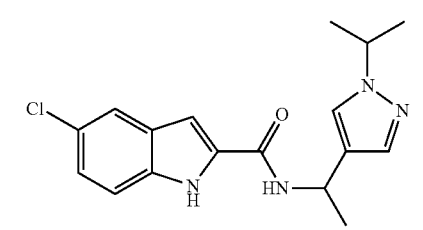
136 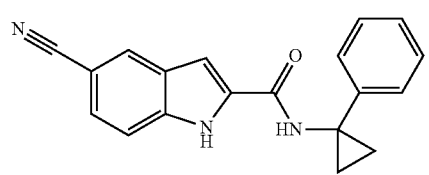
137 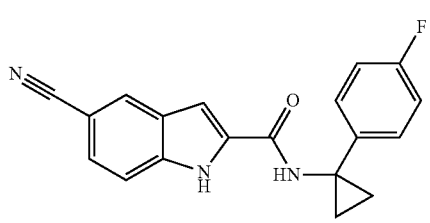
138 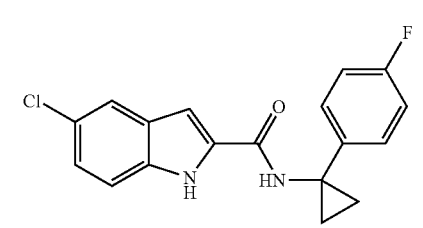
139 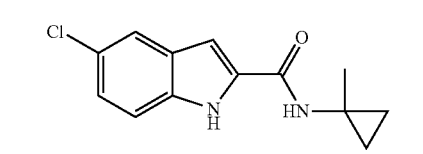
140 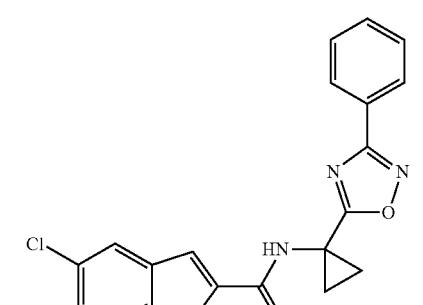
141 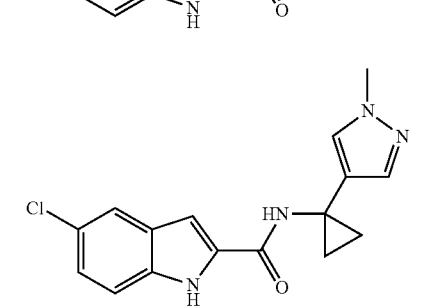
142 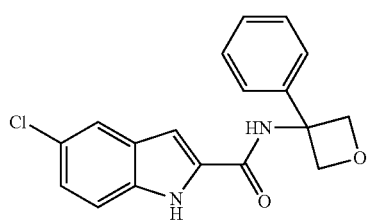
143 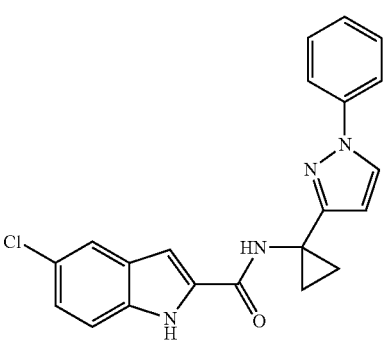
144 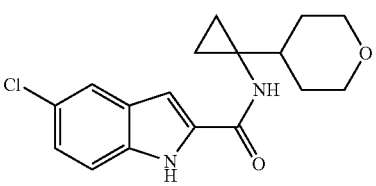
145 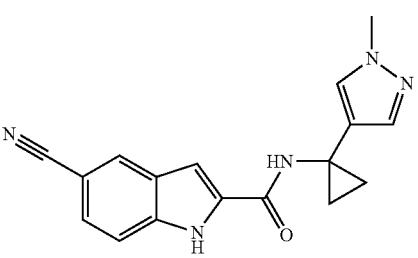
146 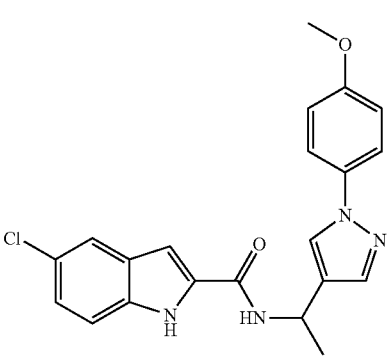
147 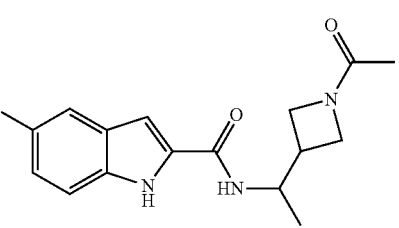

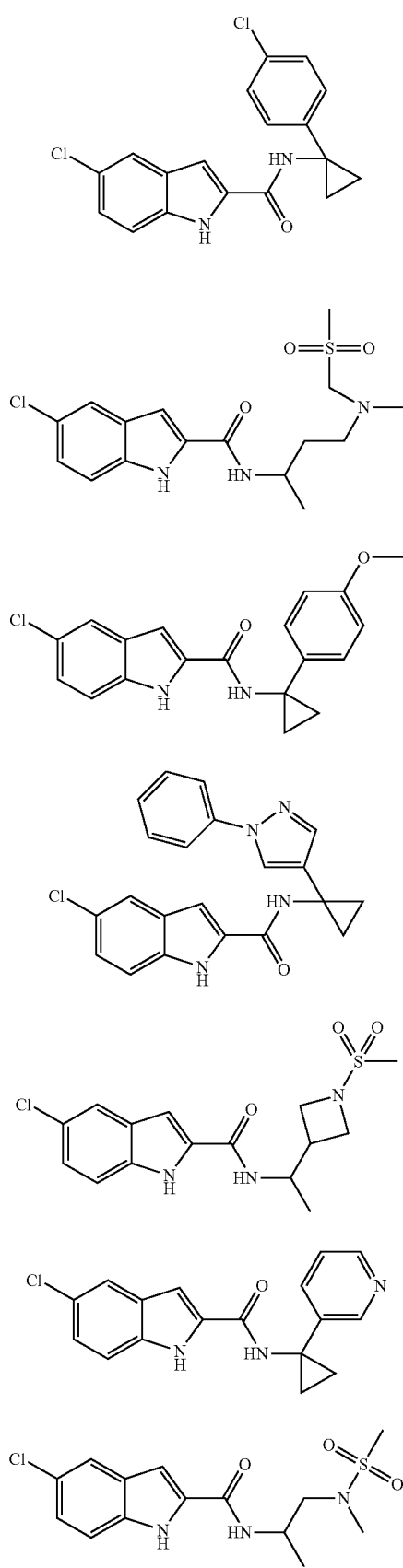
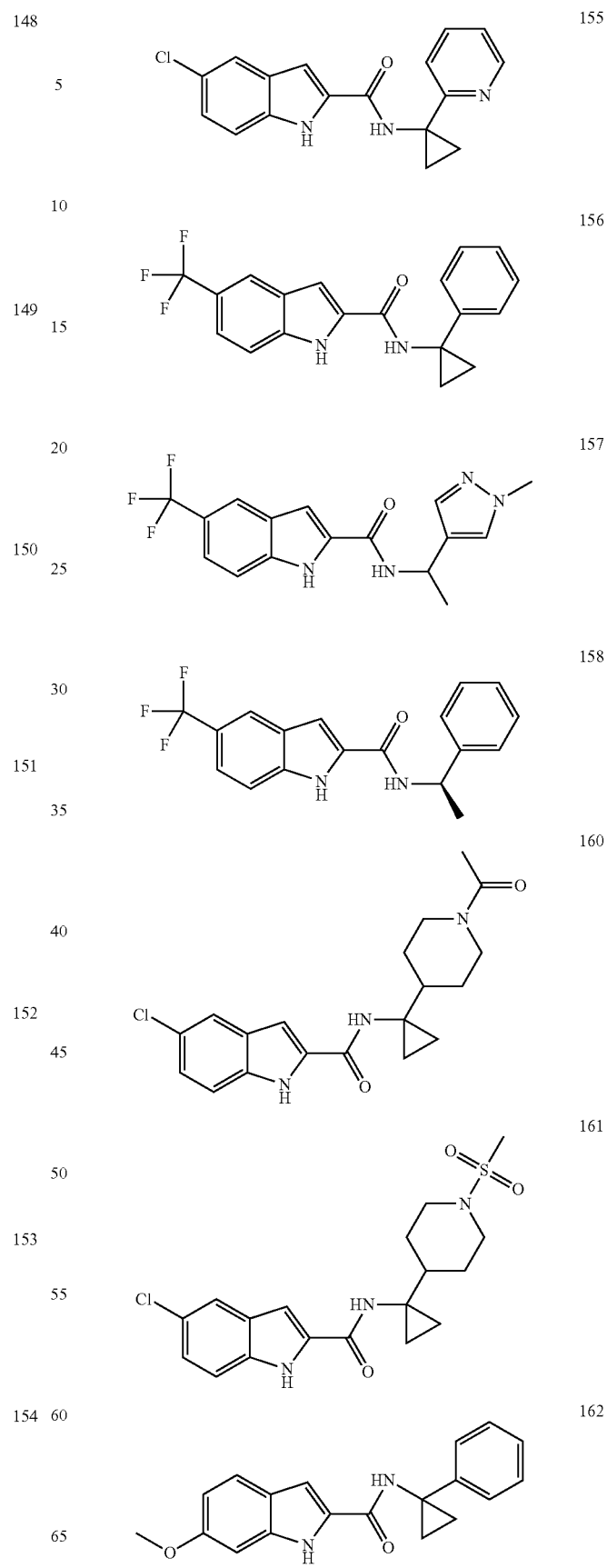

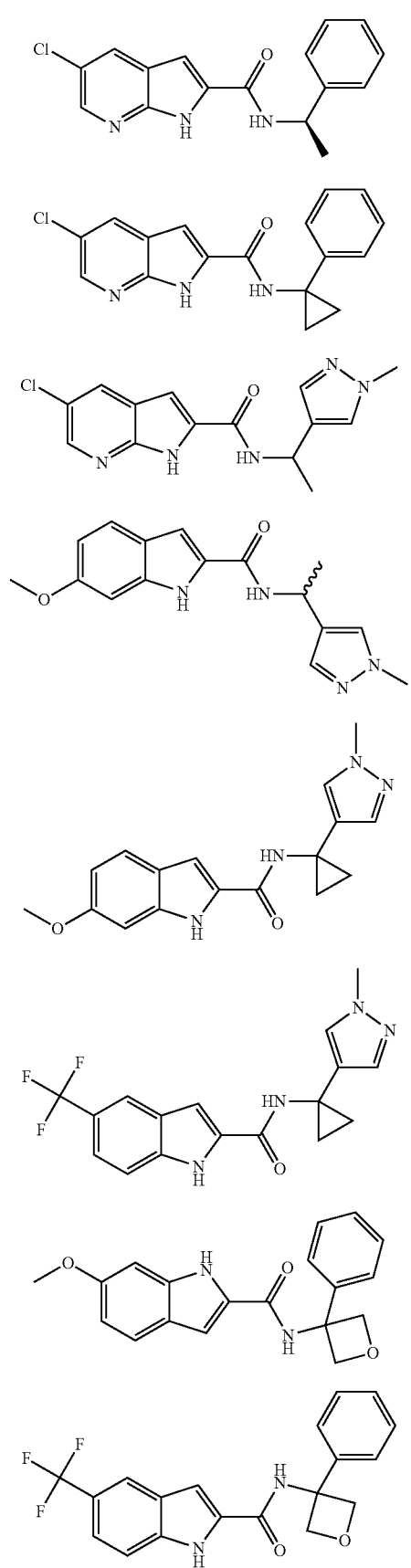
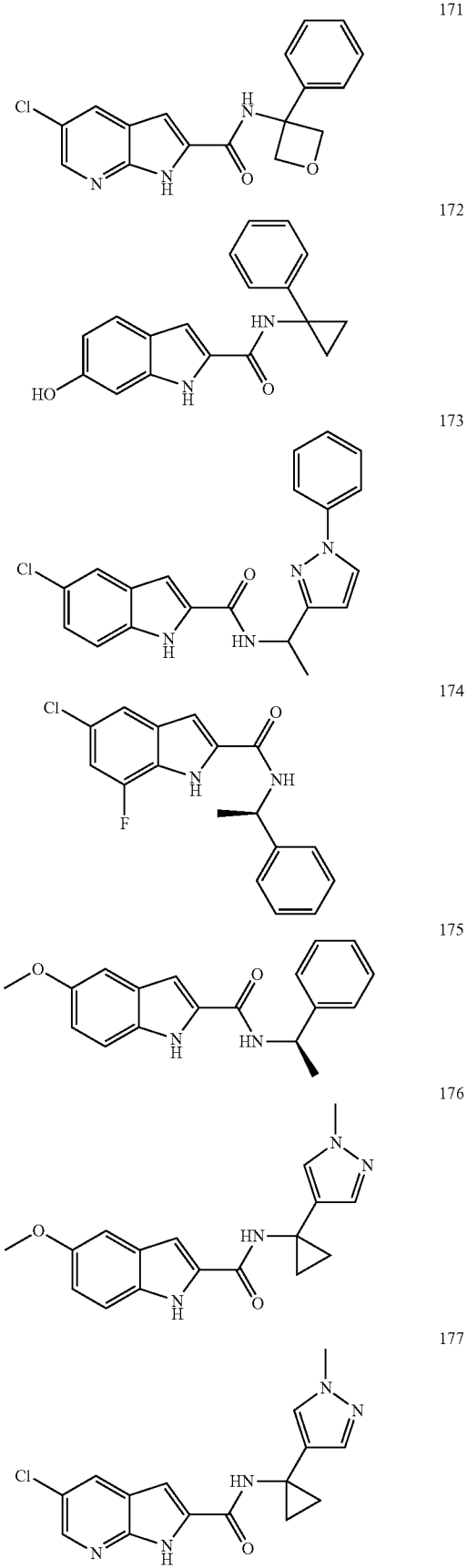

178 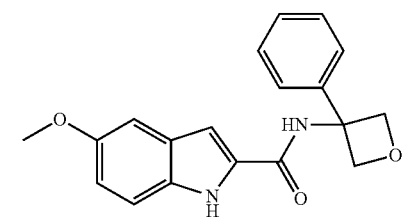
179 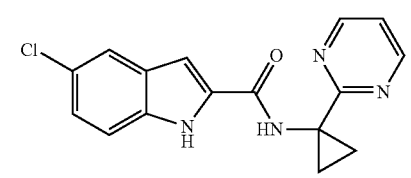
180 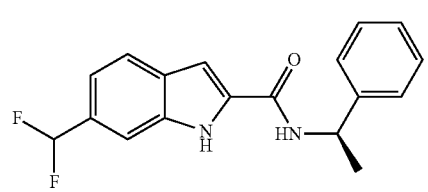
181 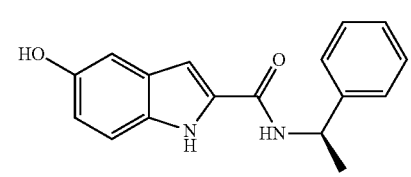
182 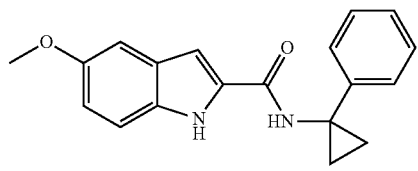
183 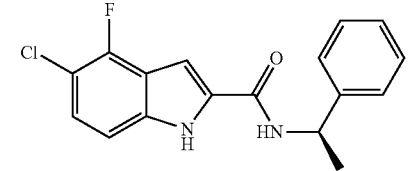
184 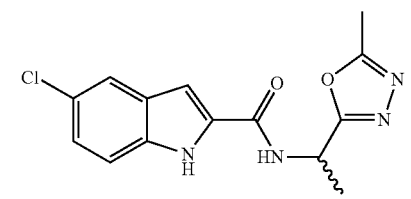
185 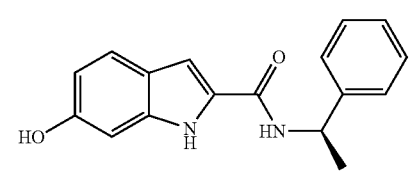
186 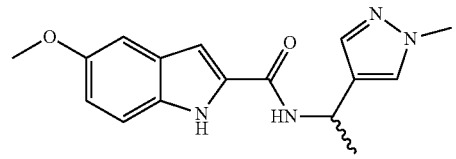
187 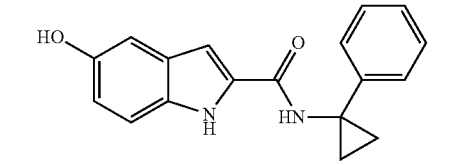
188 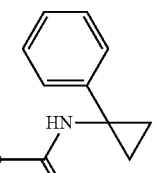
189 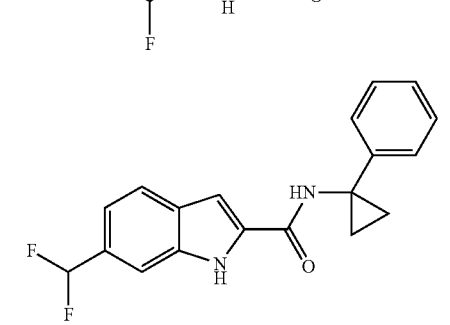
190 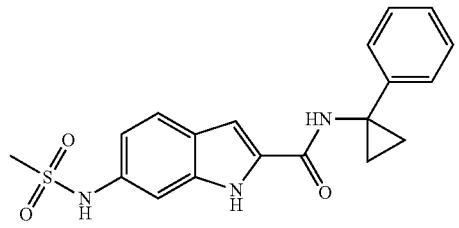
191 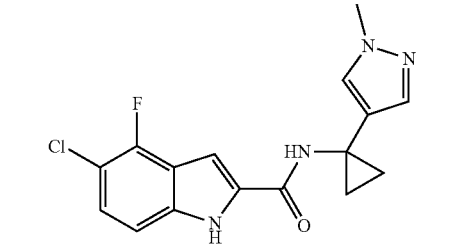
192 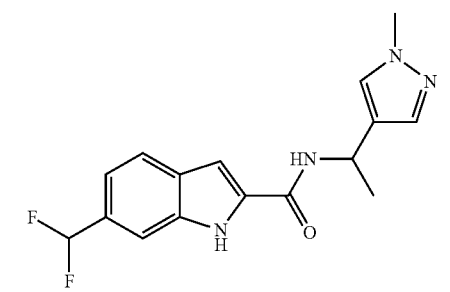

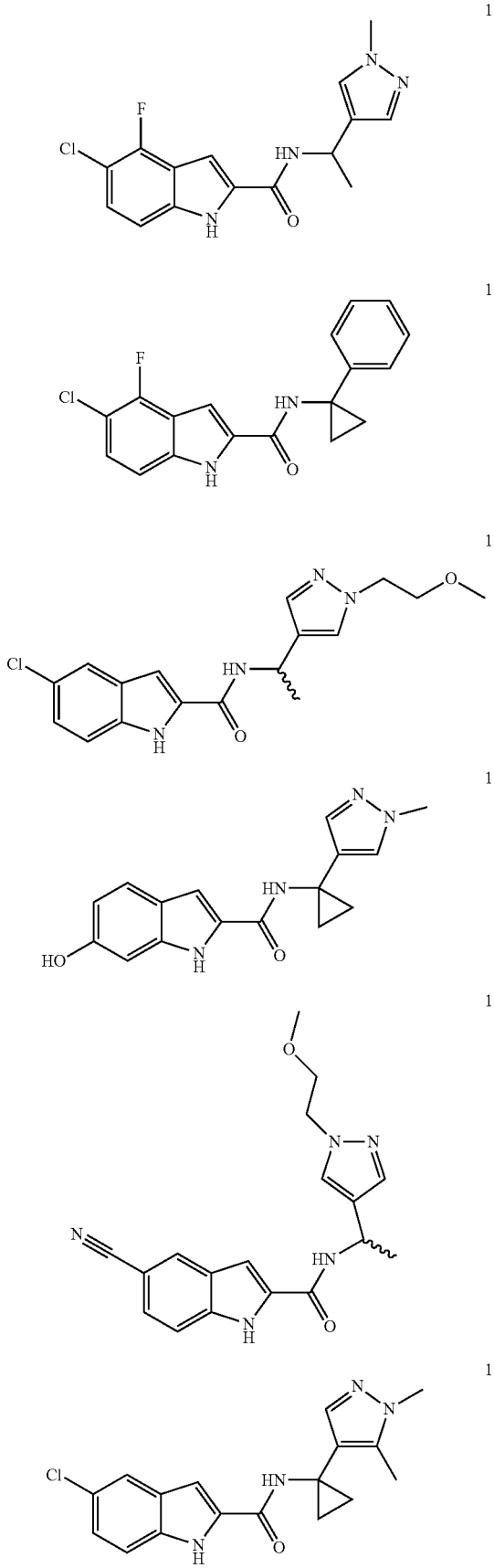
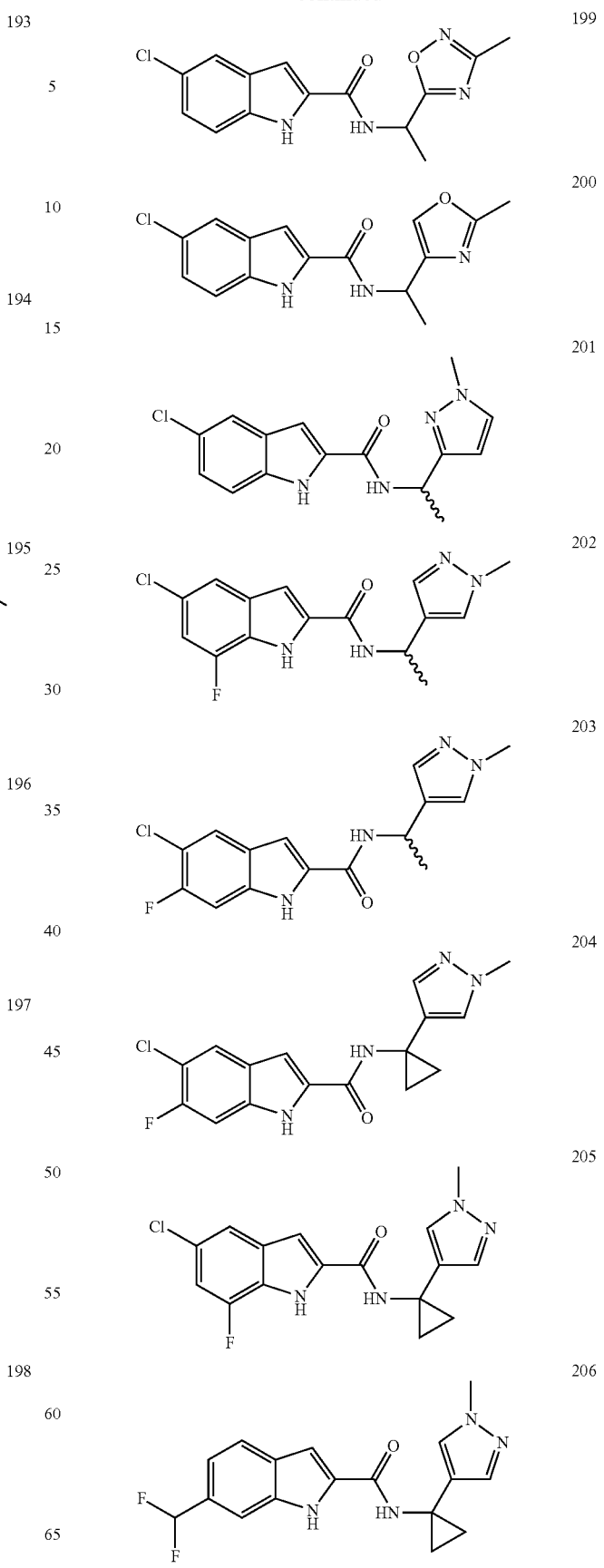

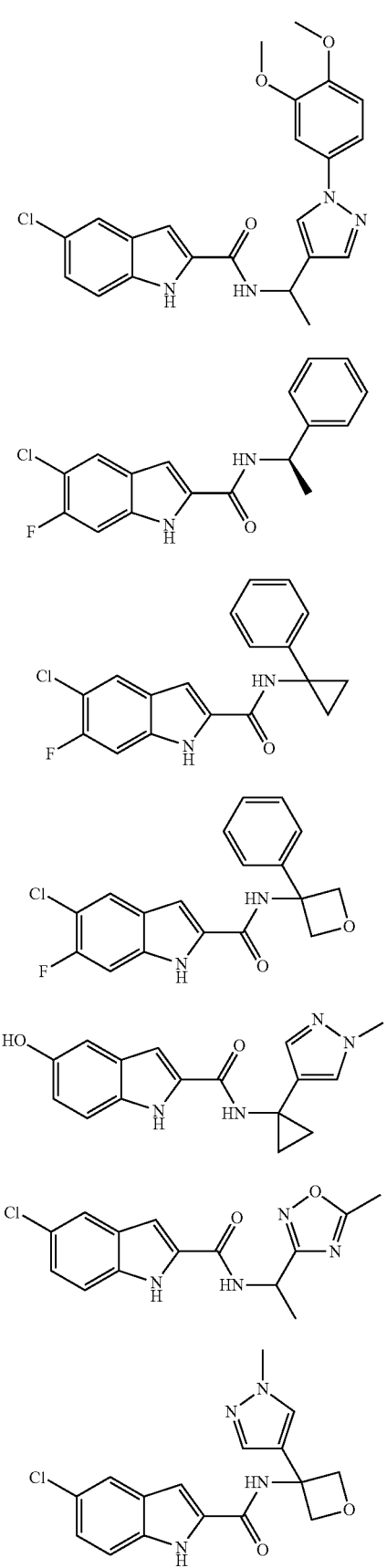
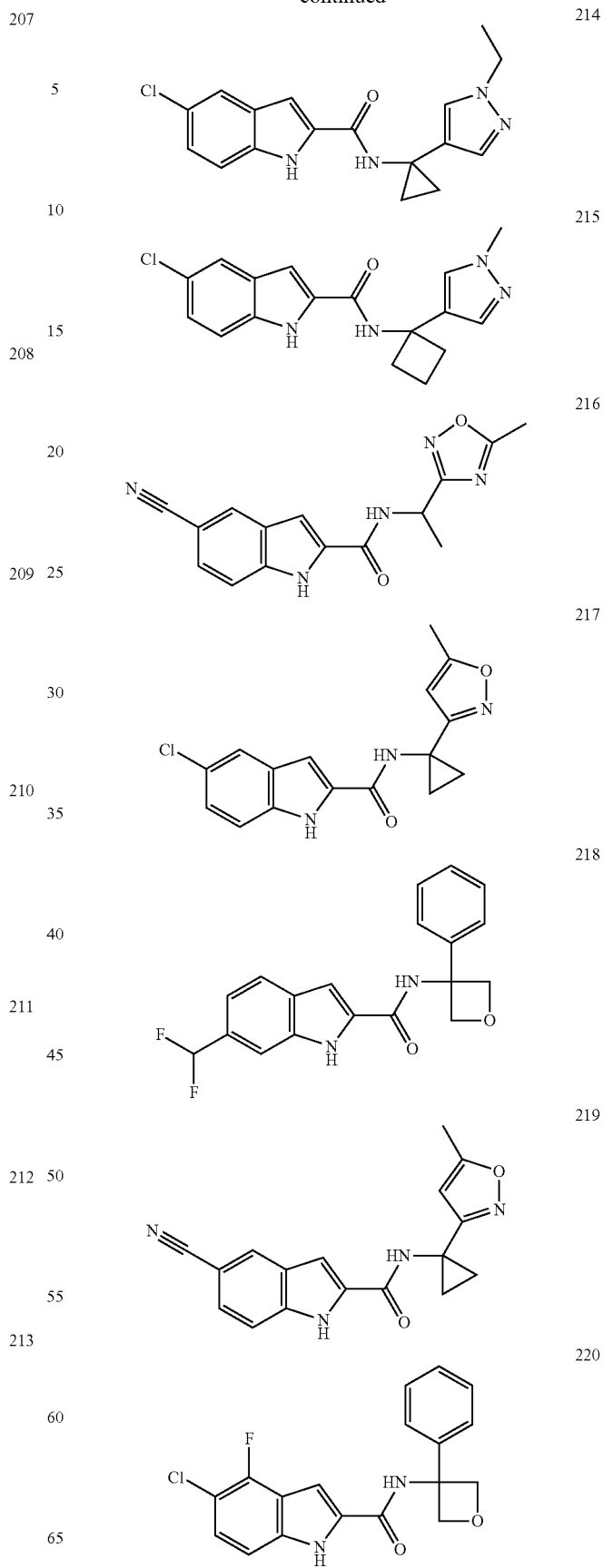

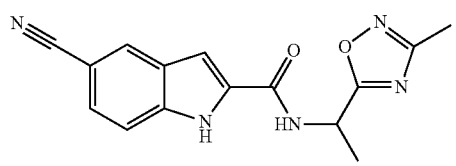 221
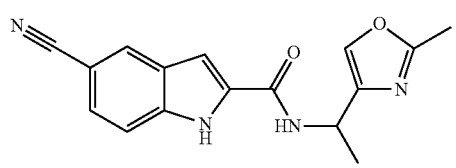 222
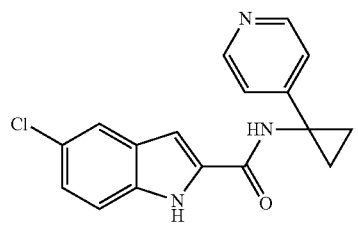 223
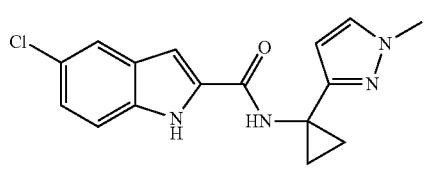 224
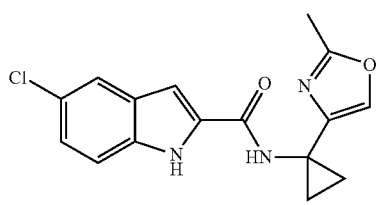 225
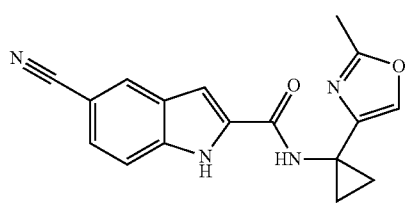 226
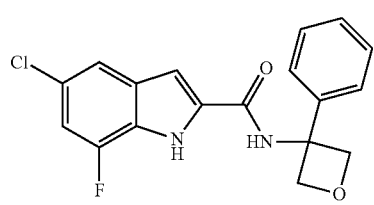 227
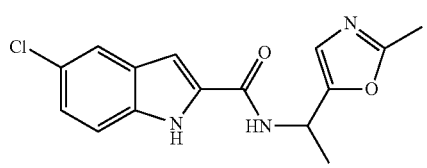 228
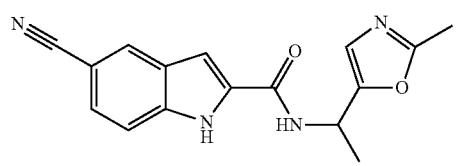 229
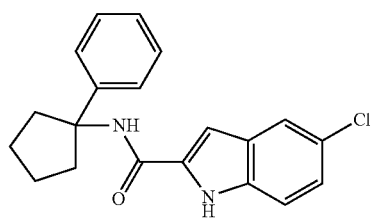 230
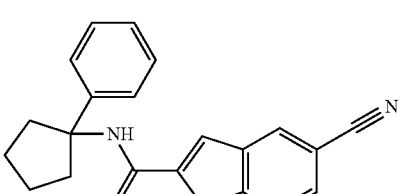 231
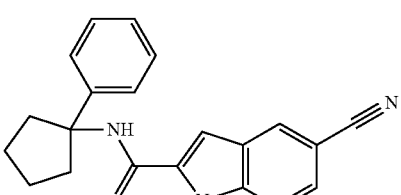 232
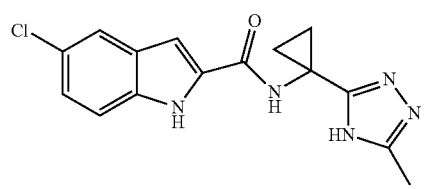 233
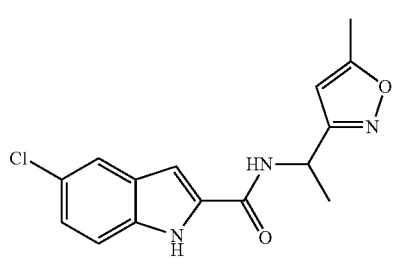 234
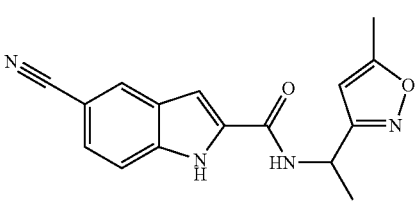 235

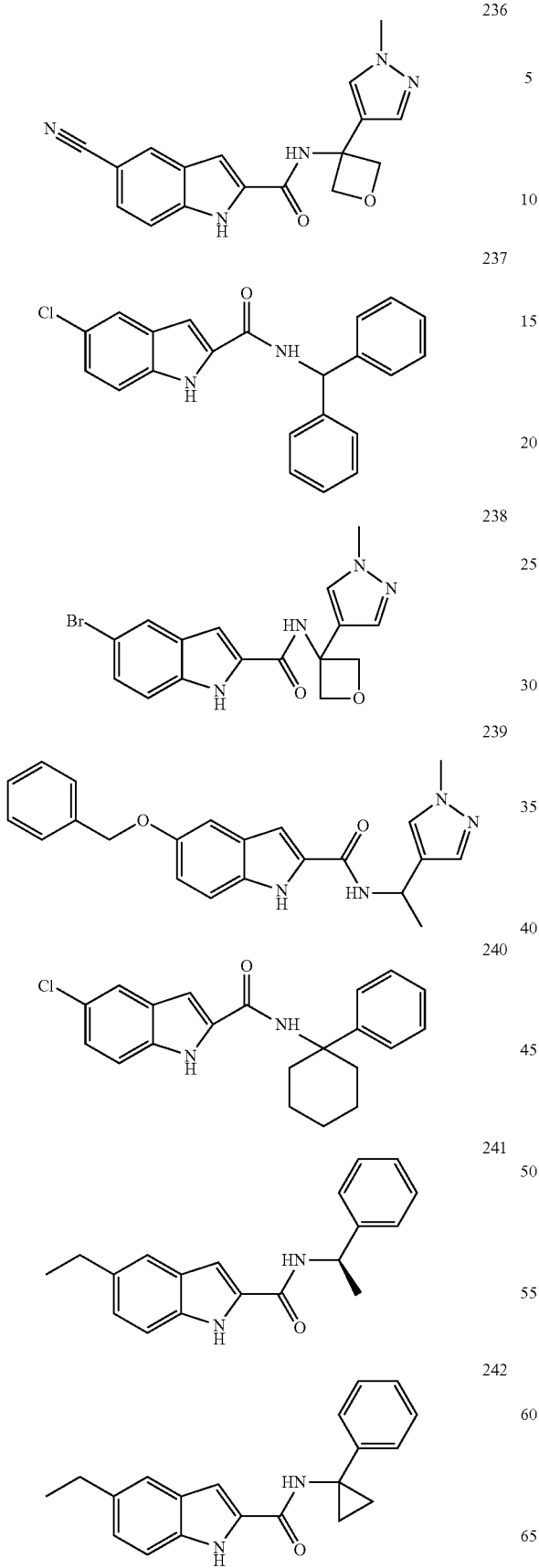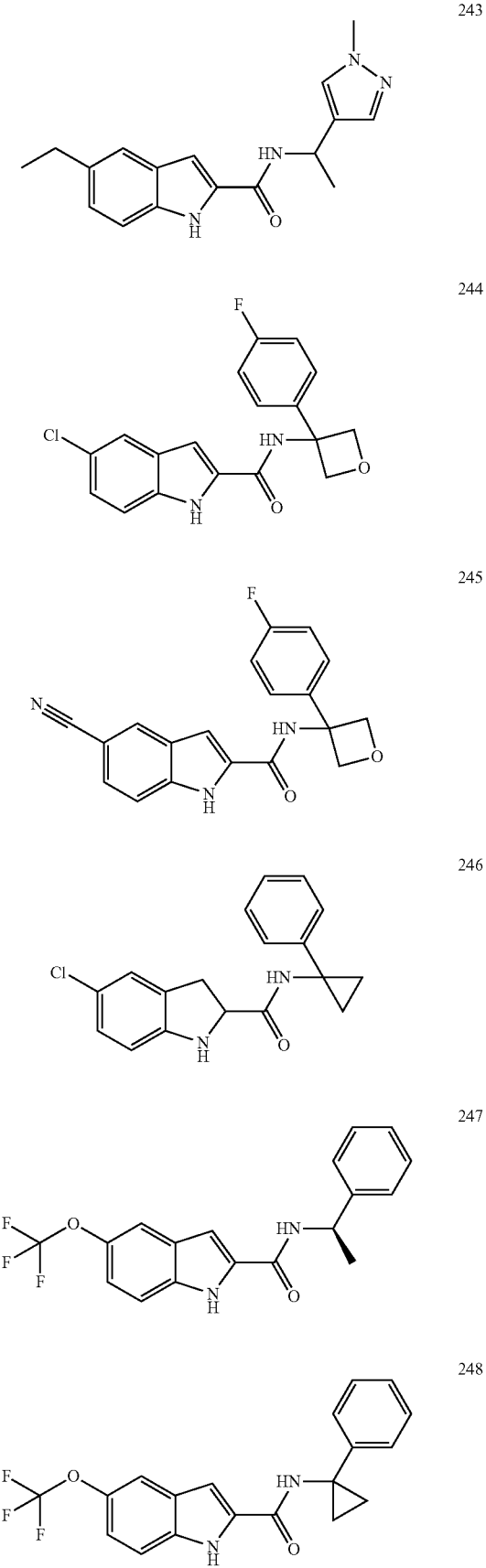

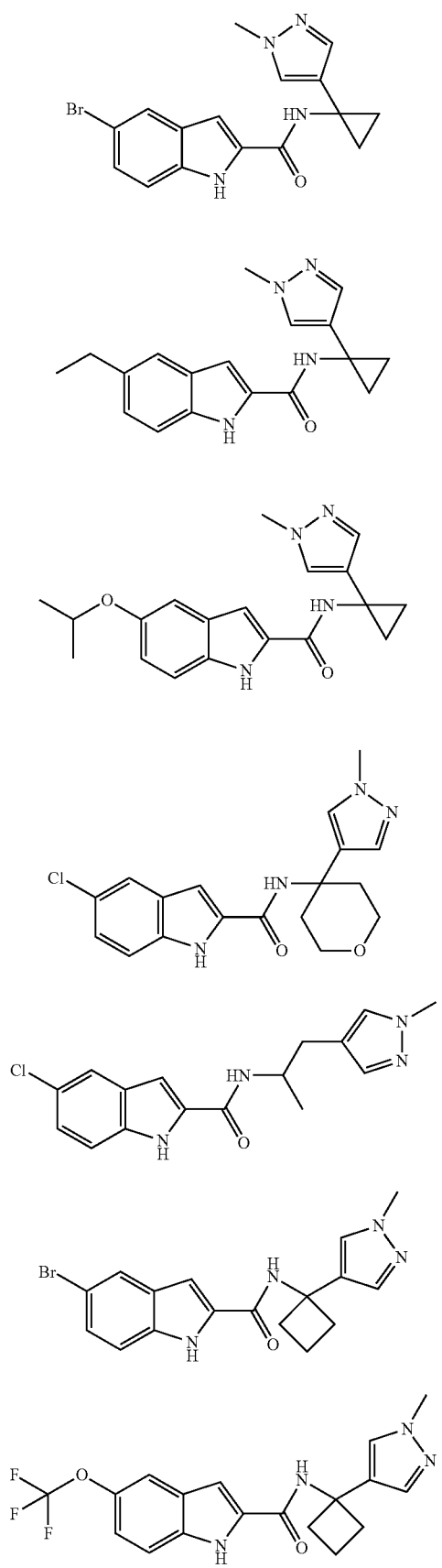
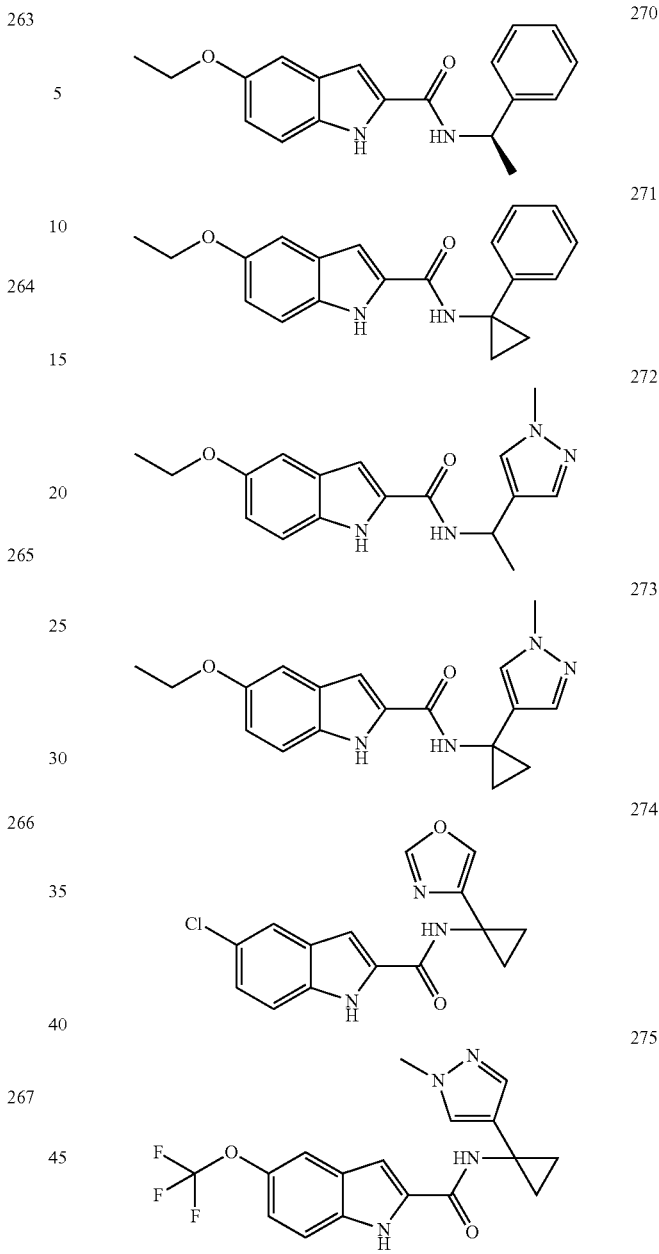

In some instances, the above formulae (and all formulae herein) are shown in non-stereoisomeric form, in other cases in stereoisomeric form, and in yet further cases shown in a manner to indicate both enantiomers (using a wavy line). For the avoidance of doubt, in the present context a single formula is intended to represent all possible stereoisomers of a particular structure, including all possible isolated enantiomers corresponding to the formula, all possible mixtures of enantiomers corresponding to the formula, all possible mixtures of diastereomers corresponding to the formula, all possible mixtures of epimers corresponding to the formula and all possible racemic mixtures corresponding to the formula. In addition to this, the above formulae (and all formulae herein) are intended to represent all tautomeric forms equivalent to the corresponding formula.

In addition to the above compounds that were not previously known, the present invention, and in particular the synthetic method, provides further compounds comprising a formula selected from one of the following:

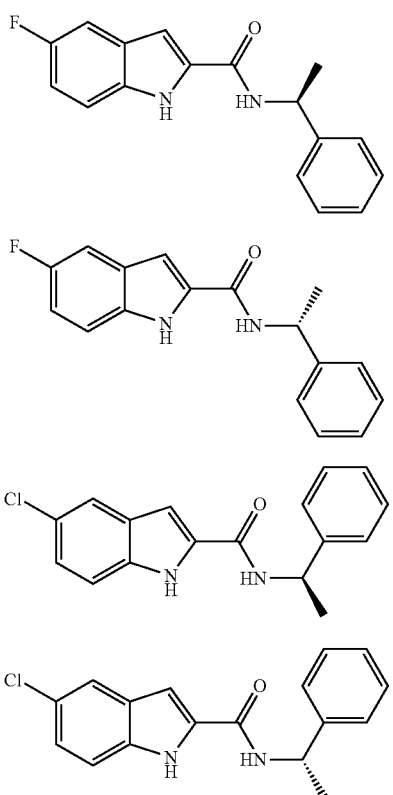

40

43

48

50

These compounds have previously been synthesised as racemic mixtures, but not as isolated enantiomers or other mixtures of stereoisomers that are not racemic. Accordingly, the invention extends to such compounds wherein the compound may comprise an isolated enantiomer corresponding to the formula, or may comprise a non-racemic mixture of enantiomers corresponding to the formula, a mixture of diastereomers corresponding to the formula, and/or a mixture of epimers corresponding to the formula.

The invention will now be described in more detail, by way of example only, with reference to the following specific embodiments.

EXAMPLES

Exemplary compounds of the invention were prepared, and tested to determine their effect as TDO and/or IDO inhibitors. These were compared with reference compound REF:

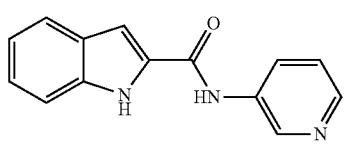

REF

Exemplary Syntheses of Compounds of the Invention

As has been mentioned, the compounds of the invention may be synthesised using known coupling reactions, and starting materials that are readily available. Exemplary syntheses of two compounds of the invention are shown below.

Compound 48 was synthesised according to the following route:

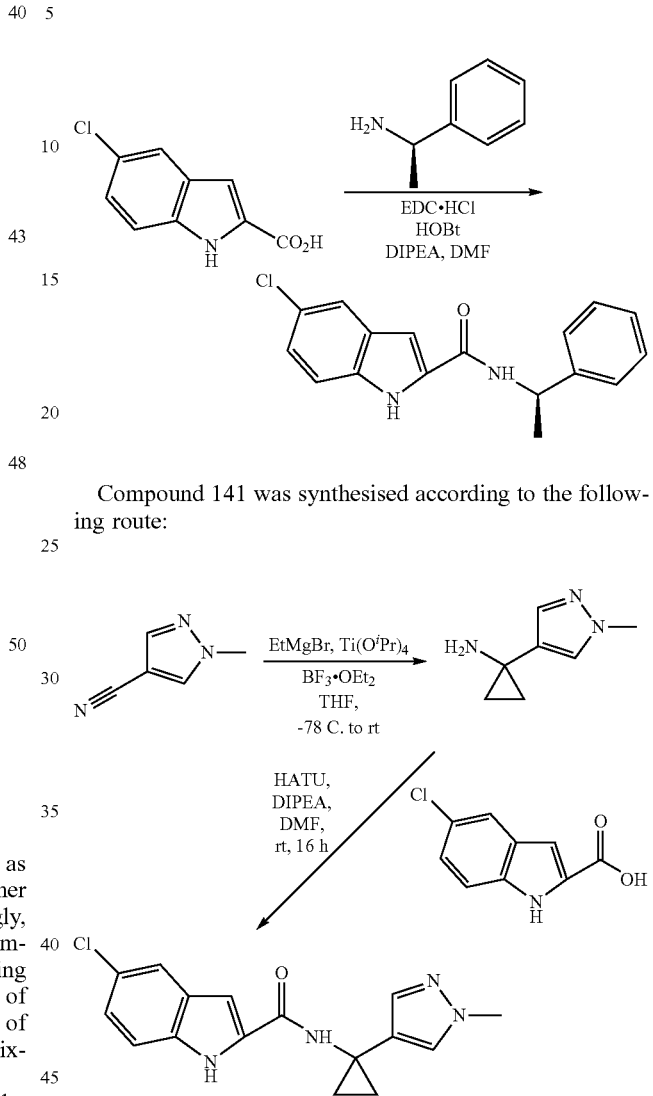

48

Compound 141 was synthesised according to the following route:

Assays

Two different types of assay were employed: 1. A TDO and IDO biochemical coupled assay which utilised recombinantly produced and purified TDO and IDO enzymes in combination with the enzyme formamidase. This coupled enzyme system allowed conversion of N-formylkynurenine produced by TDO or IDO activity to kynurenine which was then quantified by fluorescence following addition of Erhlich's Reagent. 2. A cell-based assay for detecting the effect of test compounds on kynurenine production in two different cancer cell types. This assay utilised cancer cells which expressed either TDO or IDO and as such was used as a means of testing compound activity at these two enzymes in a cell-based context. The protocols for these are set out below.

TDO Biochemical Assays

2 µM of human TDO protein was pre-incubated for 10 minutes at RT with test compounds in the presence of 50 mM $KH_2PO_4$, pH 7.0, 0.5 mM EDTA, 0.5 mM EGTA, 0.05% Triton X-100, 20 mM ascorbate, 500 U/ml catalase, 10 µM methylene blue at RT in a 384 well plate. 0.05 µg/µl kynurenine formamidase and 330 µM or 178 µM L-tryptophan were added and the assays were incubated at room temperature (RT) for 17 min. Assays were stopped and the level of kynurenine was determined by incubation with Ehrlich's reagent to a final concentration of 1.33% at RT for 5 min. Fluorescence intensity was read at 475 nm/530 nm.

IDO Biochemical Assays 0.17 µM of human IDO protein was pre-incubated for 10 min or 120 min at RT with test compounds in the presence of 50 mM $KPO_4$, pH 7.0, 0.5 mM EDTA, 0.5 mM EGTA, 0.05% Triton X-100, 20 mM ascorbate, 500 U/ml catalase, 10 µM methylene blue at RT in a 384 well plate. 0.05 µg/µl kynurenine formamidase and 45 µM or 121 µM L-tryptophan (L-Trp) were added and the assays were incubated at RT for 17 min. Assays were stopped and the level of kynurenine was determined by incubation with Ehrlich's reagent to a final concentration of 1.33% at RT for 5 min. Fluorescence intensity was read at 475 nm/530 nm.

TDO and IDO Cell-Based Assays

A172 human glioblastoma (ATCC) were grown in DMEM+2 mM L-glutamine medium supplemented with 10% foetal bovine serum and SKOV-3 ovary adenocarcinoma (ATCC) cells were grown in McCoys 5A+L-glutamax medium supplemented with 15% foetal bovine serum. On the day of assay, cells were detached using trypsin-EDTA (0.25% v/v), re-suspended in assay media (RPMI 1640 phenol red free+L-glutamine supplemented with 10% dialysed foetal bovine serum). A172 cells were seeded at 30K cells per well and SKOV-3 cells at 40K cells per well into 96-well plates containing test samples/vehicle control together with 500 µM L-Trp. Cells were then incubated for 48 h at 37° C., 5% $CO_2$. In SK-OV-3 cells, IFNγ was also added at 500 ng/ml for the 48 h incubation in order to induce expression of IDO. Plates were centrifuged and the supernatant was removed and incubated for 5 min in the presence of 1% Erhlich's reagent. Kynurenine levels were then quantified by measuring absorbance at 490 nm.

The pIC50 values for a variety of test compounds are shown in Table 1.

TABLE 1 pIC50 values for the inhibition of IDO (SKOV-3 cells) and TDO (A172 cells) determined for test compounds

| Compound | TDO cellular assay (A172) | IDO cellular assay (SKOV3) |
|---|---|---|
| 1 | − | ++ |
| 2 | − | ++ |
| 3 | − | +++ |
| 4 | + | ++ |
| 5 | − | + |
| 6 | + | + |
| 7 | − | +++ |
| 8 | − | + |
| 9 | − | +++ |
| 10 | + | − |
| 11 | ++ | ++ |
| 12 | − | +++ |
| 13 | − | + |
| 14 | − | ++ |
| 15 | ++ | +++ |
| 16 | + | +++ |
| 17 | + | +++ |
| 18 | − | +++ |
| 19 | − | +++ |
| 20 | − | + |
| 21 | − | ++ |
| 22 | + | ++ |
| 23 | − | +++ |
| 24 | + | ++ |
| 25 | +++ | +++ |
| 26 | ++ | +++ |
| 27 | − | ++ |
| 28 | − | + |
| 29 | − | + |
| 30 | − | + |
| 31 | − | + |
| 32 | − | ++ |
| 33 | − | ++ |
| 34 | − | +++ |
| 35 | − | + |
| 36 | + | +++ |
| 37 | − | + |
| 38 | + | ++ |
| 39 | − | ++ |
| 40 | ++ | + |
| 41 | − | +++ |
| 42 | − | ++ |
| 43 | ++ | +++ |
| 44 | + | +++ |
| 45 | − | + |
| 46 | − | ++ |
| 47 | ++ | ++ |
| 48 | ++ | +++ |
| 49 | + | ++ |
| 50 | +++ | +++ |
| 51 | − | +++ |
| 52 | + | + |
| 53 | − | + |
| 54 | − | + |
| 55 | + | − |
| 56 | + | + |
| 57 | + | − |
| 58 | − | ++ |
| 59 | − | + |
| 60 | + | + |
| 61 | +++ | +++ |
| 62 | +++ | +++ |
| 63 | + | + |
| 64 | ++ | ++ |
| 65 | − | +++ |
| 66 | − | ++ |
| 67 | ++ | + |
| 68 | ++ | +++ |
| 69 | ++ | +++ |
| 70 | ++ | +++ |
| 71 | + | +++ |
| 72 | − | +++ |
| 73 | − | + |
| 74 | − | + |
| 75 | − | +++ |
| 76 | − | + |
| 77 | + | +++ |
| 78 | + | ++ |
| 79 | − | + |
| 80 | − | ++ |
| 81 | − | + |
| 82 | +++ | +++ |
| 83 | − | +++ |
| 84 | ++ | +++ |
| 85 | ++ | ++ |
| 86 | +++ | +++ |
| 87 | + | +++ |
| 88 | +++ | − |
| 89 | +++ | − |
| 90 | − | +++ |
| 91 | − | + |
| 92 | + | +++ |
| 93 | + | +++ |
| 94 | + | ++ |
| 95 | − | + |
| 96 | − | + |
| 97 | + | ++ |

TABLE 1-continued pIC50 values for the inhibition of IDO (SKOV-3 cells) and TDO (A172 cells) determined for test compounds

| Compound | TDO cellular assay (A172) | IDO cellular assay (SKOV3) |
|---|---|---|
| 98 | − | +++ |
| 99 | + | +++ |
| 100 | ++ | +++ |
| 101 | + | +++ |
| 102 | − | + |
| 103 | − | +++ |
| 104 | + | ++ |
| 105 | − | +++ |
| 106 | − | + |
| 107 | − | ++ |
| 108 | − | ++ |
| 109 | − | ++ |
| 110 | − | ++ |
| 111 | − | ++ |
| 112 | − | +++ |
| 113 | − | +++ |
| 114 | − | +++ |
| 115 | + | +++ |
| 116 | ++ | − |
| 117 | + | ++ |
| 118 | + | ++ |
| 119 | − | + |
| 120 | − | +++ |
| 121 | − | +++ |
| 122 | − | ++ |
| 123 | + | ++ |
| 124 | − | +++ |
| 125 | + | +++ |
| 126 | − | +++ |
| 127 | − | + |
| 128 | + | +++ |
| 129 | − | ++ |
| 130 | − | ++ |
| 131 | − | +++ |
| 132 | + | +++ |
| 133 | − | +++ |
| 134 | − | +++ |
| 135 | − | +++ |
| 136 | − | +++ |
| 137 | − | +++ |
| 138 | − | +++ |
| 139 | − | + |
| 140 | − | +++ |
| 141 | − | +++ |
| 142 | + | +++ |
| 143 | + | +++ |
| 144 | + | +++ |
| 145 | − | +++ |
| 146 | − | +++ |
| 147 | − | +++ |
| 148 | + | +++ |
| 149 | − | +++ |
| 150 | ++ | +++ |
| 151 | − | +++ |
| 152 | − | ++ |
| 153 | − | +++ |
| 154 | − | + |
| 155 | − | +++ |
| 156 | − | +++ |
| 157 | − | ++ |
| 158 | − | +++ |
| 159 | − | ++ |
| 160 | − | +++ |
| 161 | − | +++ |
| 162 | − | ++ |
| 163 | − | + |
| 164 | − | +++ |
| 165 | − | + |
| 166 | − | + |
| 167 | − | ++ |
| 168 | + | +++ |
| 169 | − | ++ |
| 170 | + | +++ |
| 171 | − | +++ |
| 172 | − | + |
| 173 | − | +++ |
| 174 | ++ | +++ |
| 175 | − | +++ |
| 176 | − | +++ |
| 177 | − | ++ |
| 178 | − | +++ |
| 179 | − | ++ |
| 180 | − | + |
| 181 | − | + |
| 182 | − | +++ |
| 183 | + | +++ |
| 184 | − | ++ |
| 185 | + | + |
| 186 | − | +++ |
| 187 | − | + |
| 188 | + | +++ |
| 189 | − | ++ |
| 190 | − | + |
| 191 | − | +++ |
| 192 | − | + |
| 193 | − | +++ |
| 194 | − | +++ |
| 195 | − | ++ |
| 196 | − | + |
| 197 | − | + |
| 198 | − | +++ |
| 199 | − | +++ |
| 200 | − | +++ |
| 201 | − | + |
| 202 | − | +++ |
| 203 | + | ++ |
| 204 | − | +++ |
| 205 | − | +++ |
| 206 | − | + |
| 207 | + | +++ |
| 208 | + | +++ |
| 209 | ++ | +++ |
| 210 | + | +++ |
| 211 | − | + |
| 212 | + | ++ |
| 213 | − | +++ |
| 214 | − | +++ |
| 215 | − | +++ |
| 216 | − | + |
| 217 | − | +++ |
| 218 | − | + |
| 219 | − | +++ |
| 220 | − | +++ |
| 221 | − | + |
| 222 | − | ++ |
| 223 | − | +++ |
| 224 | ++ | ++ |
| 225 | − | +++ |
| 226 | − | +++ |
| 227 | ++ | +++ |
| 228 | ++ | ++ |
| 229 | +++ | +++ |
| 230 | − | +++ |
| 231 | − | +++ |
| 232 | − | +++ |
| 233 | − | + |
| 234 | ++ | +++ |
| 235 | − | +++ |
| 236 | − | +++ |
| 237 | − | ++ |
| 238 | − | +++ |
| 239 | − | + |
| 240 | − | +++ |
| 241 | − | +++ |
| 242 | − | +++ |
| 243 | − | +++ |
| 244 | − | +++ |
| 245 | − | +++ |

TABLE 1-continued pIC50 values for the inhibition of IDO (SKOV-3 cells) and TDO (A172 cells) determined for test compounds

| Compound | TDO cellular assay (A172) | IDO cellular assay (SKOV3) |
|---|---|---|
| 246 | + | +++ |
| 247 | − | +++ |
| 248 | − | +++ |
| 249 | + | +++ |
| 250 | − | +++ |
| 251 | − | +++ |
| 252 | − | +++ |
| 253 | − | +++ |
| 254 | − | +++ |
| 255 | + | +++ |
| 256 | + | + |
| 257 | − | +++ |
| 258 | − | +++ |
| 259 | − | +++ |
| 260 | + | +++ |
| 261 | − | +++ |
| 262 | − | + |
| 263 | − | +++ |
| 264 | − | +++ |
| 265 | − | +++ |
| 266 | − | +++ |
| 267 | ++ | +++ |
| 268 | − | +++ |
| 269 | − | +++ |
| 270 | − | +++ |
| 271 | ++ | +++ |
| 272 | − | +++ |
| 273 | − | +++ |
| 274 | − | +++ |
| 275 | − | +++ |

Key:
+++ = $pIC_{50} \geq 5.50$
++ = $pIC_{50}$ 5.00-<5.50
+ = $pIC_{50}$ 4.50-<5.00
− = $pIC_{50}$ <4.50

The Table shows that a large number of the test compounds show strong TDO and IDO inhibitory function in cell-based assays. This compares with the REF compound, which scored '−' and '−' on each of the tests, and which is therefore disclaimed in the present invention, since it is not TDO or IDO active.

Biochemical enzyme assays were conducted according to the protocols described above, and the results confirmed the bona fide activity of the compounds as enzyme inhibitors. Compounds 83, 160, 178, 205, 215, 230 and 231 all showed a $pIC_{50}$ in the hIDO assay of >5. For example, compound 83 showed a $pIC_{50}$ in hIDO of 5.24. This compares with the REF compound, which scored <3.99 and <3.99 on the hTDO and hIDO tests respectively.

The invention claimed is:

1. A compound of the following formula, or a pharmaceutically acceptable salt thereof:

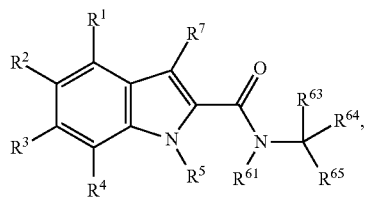

wherein:
each of $R^1$, $R^2$, $R^3$ and $R^4$ is independently selected from H, halogen, —CN, $C_1$-$C_6$ alkyl, $C_1$-$C_6$ halogenated alkyl, —OH, $C_1$-$C_7$ alkoxy, —O—$CF_3$, —C(O)—$NH_2$, —C(O)—NHMe, NH—$SO_2$Me, NH—$SO_2$Et, —NH—$SO_2$Pr, and —NH—$SO_2$iPr;

$R^5$ is H;

$R^7$ is selected from H and $C_1$-$C_6$ alkyl;

$R^{61}$ is selected from H and $C_1$-$C_6$ alkyl;

$R^{65}$ is a heterocyclic group selected from pyrazol-1-yl, pyrazol-3-yl, pyrazol-4-yl, pyrazol-5-yl, 1,2,3-triazol-4-yl, 1,2,3-triazol-5-yl, 1,2,4-triazol-1-yl, 1,2,4-triazol-3-yl, 1,2,4-triazol-5-yl, pyridin-2-yl, pyridin-3-yl, pyridin-4-yl, pyrimidin-2-yl, pyrimidin-4-yl, pyrimidin-5-yl, pyrimidin-6-yl, piperidin-1-yl, piperidin-2-yl, piperidin-3-yl, piperidin-4-yl, oxazol-2-yl, oxazol-4-yl, oxazol-5-yl, isoxazol-3-yl, isoxazol-4-yl, isoxazol-5-yl, tetrazol-1-yl, tetrazol-2-yl, and tetrazol-5-yl; each of which is optionally substituted with one to three substituents independently selected from halogen, methyl, ethyl, propyl, —C(O)-methyl, —S(O)$_2$-methyl and phenyl; and $R^{63}$ and $R^{64}$ together form a 3-6 membered carbocyclic or heterocyclic ring selected from cyclopropyl, cyclobutyl, cyclopentyl, cyclopentenyl, cyclohexyl, cyclohexenyl, aziridinyl, azetidinyl, pyrrolidinyl, piperidinyl, piperazinyl, oxetanyl, tetrahydrofuranyl and tetrahydropyranyl.

2. The compound according to claim 1, or a pharmaceutically acceptable salt thereof, wherein:
each of $R^1$, $R^2$, $R^3$ and $R^4$ is independently selected from H, halogen, —CN, methyl, ethyl, propyl, iso-propyl, n-butyl, iso-butyl, tert-butyl, —$CF_3$, —$CHF_2$, —OH, —O-methyl, —O— ethyl, —O-propyl, and —$OCF_3$;

$R^5$ is H;

$R^7$ is selected from H and methyl;

$R^{61}$ is selected from H, methyl, ethyl, propyl and iso-propyl;

$R^{65}$ is pyrazol-1-yl, pyrazol-3-yl, pyrazol-4-yl, pyrazol-5-yl, 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, oxazol-2-yl, oxazol-4-yl, isoxazol-3-yl, tetrazol-1-yl, tetrazol-2-yl, and tetrazol-5-yl; each of which is optionally substituted with one to three substituents independently selected from halogen, methyl, ethyl, propyl and phenyl; and $R^{63}$ and $R^{64}$ together form a 3-6 membered saturated carbocyclic or heterocyclic ring selected from cyclopropyl, cyclobutyl, cyclopentyl, cyclohexyl, aziridinyl, azetidinyl, pyrrolidinyl, piperidinyl, piperazinyl, oxetanyl, tetrahydrofuranyl and tetrahydropyranyl.

3. The compound according to claim 2, or a pharmaceutically acceptable salt thereof, wherein:
each of $R^1$, $R^3$ and $R^4$ is independently selected from H, halogen and methyl;

$R^2$ is selected from halogen, —CN, methyl, ethyl, propyl, iso-propyl, —$CF_3$, —$CHF_2$, —OH, —O— methyl, —O-ethyl, —O-propyl and —$OCF_3$; and
each of $R^5$ and $R^7$ is H.

4. The compound according to claim 3, or a pharmaceutically acceptable salt thereof, wherein $R^{61}$ is H.

5. The compound according to claim 4, or a pharmaceutically acceptable salt thereof, wherein:
$R^{65}$ is a heterocyclic group selected from pyrazol-1-yl, pyrazol-3-yl, pyrazol-4-yl, pyrazol-5-yl, 1,2,4-triazol-1-yl, 1,2,4-triazol-3-yl, 1,2,4-triazol-5-yl, oxazol-4-yl, isoxazol-3-yl, tetrazol-1-yl, tetrazol-2-yl, tetrazol-5-yl; each of which is optionally substituted with one to three substituents independently selected from halogen, methyl, ethyl, propyl, and phenyl; and $R^{63}$ and $R^{64}$ together form a 3-6 membered carbocyclic or heterocyclic ring selected from cyclopropyl, cyclobutyl, cyclopentyl, and cyclohexyl.

6. The compound according to claim 2, or a pharmaceutically acceptable salt thereof, wherein:

each of $R^1$, $R^3$, and $R^4$ is H;

$R^2$ is selected from halogen, —CN, methyl, ethyl, —CF$_3$, —O-methyl and —OCF$_3$;

each of $R^5$ and $R^{61}$ is H;

$R^7$ is H;

$R^{65}$ is a heterocyclic group selected from pyrazol-1-yl, pyrazol-3-yl, pyrazol-4-yl, pyrazol-5-yl, oxazol-4-yl, isoxazol-3-yl, tetrazol-1-yl, tetrazol-2-yl, and tetrazol-5-yl; each of which is optionally substituted with one to three substituents independently selected from halogen, methyl, ethyl, propyl, and phenyl; and $R^{63}$ and $R^{64}$ together form a 3-6 membered unsubstituted saturated carbocyclic ring selected from cyclopropyl, cyclobutyl, cyclopentyl, and cyclohexyl.

7. The compound according to claim 1 selected from the following, or a pharmaceutically acceptable salt thereof:

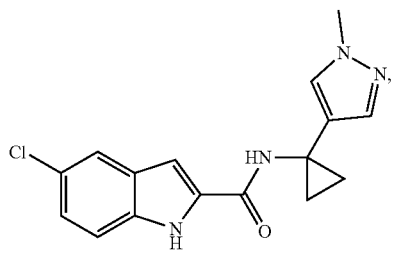

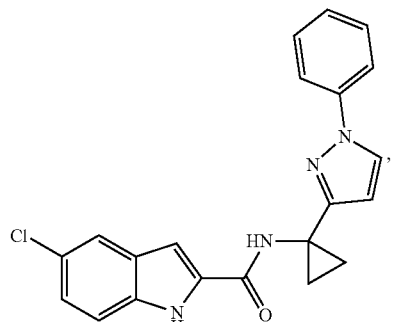

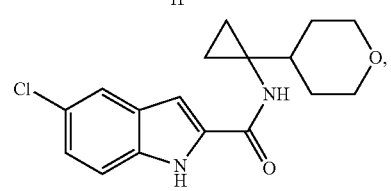

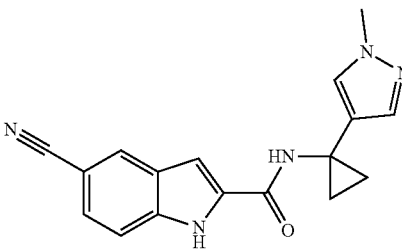

-continued

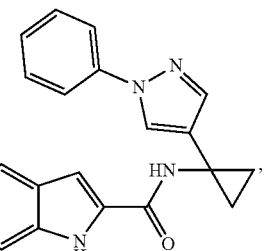

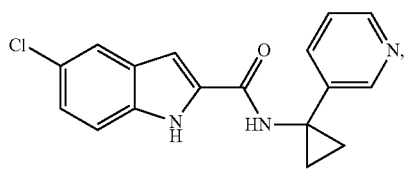

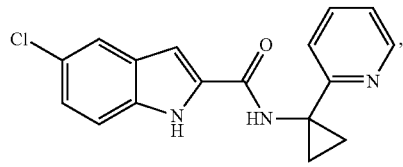

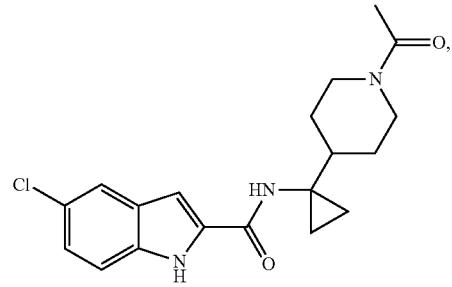

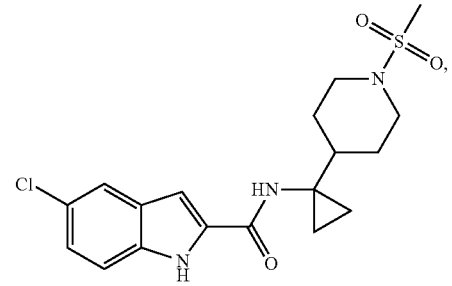

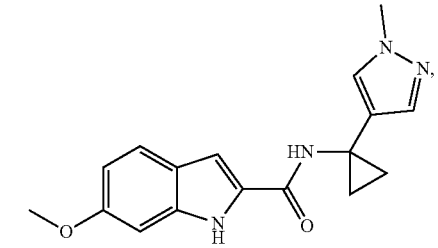

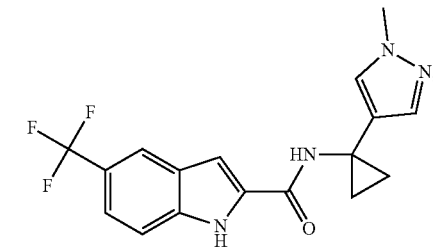

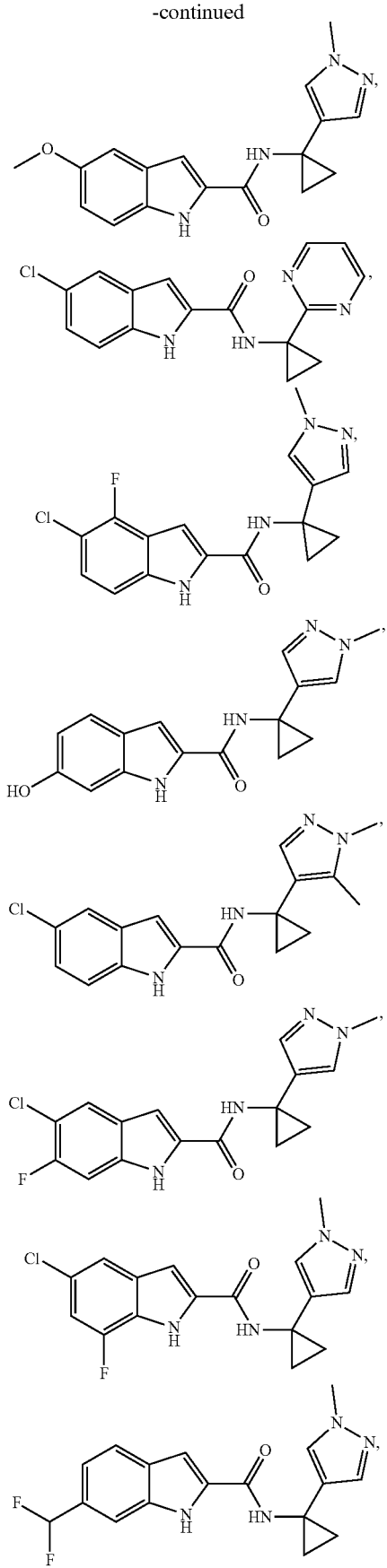
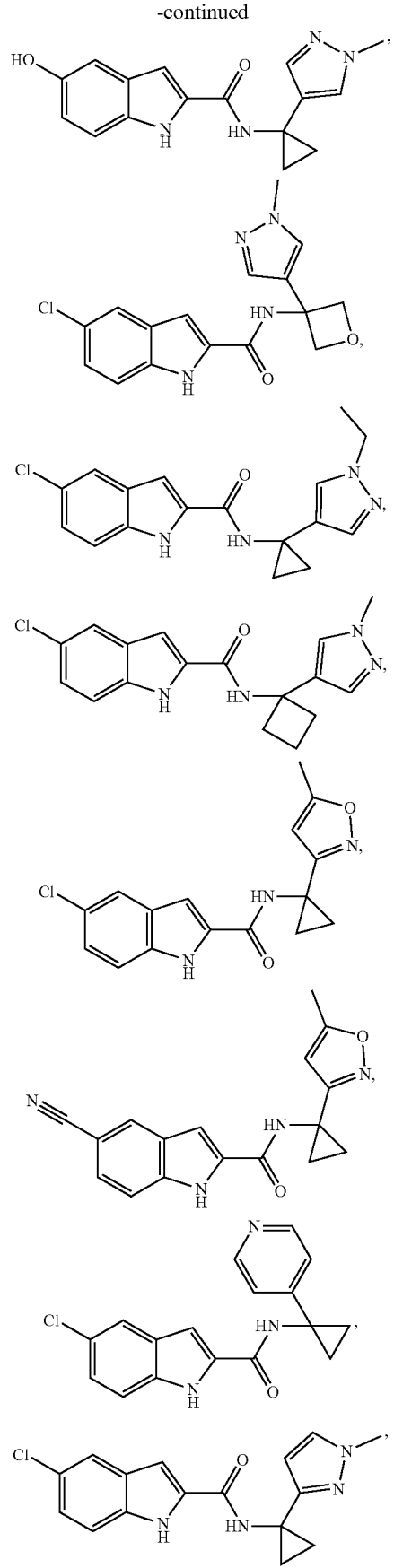

151
-continued
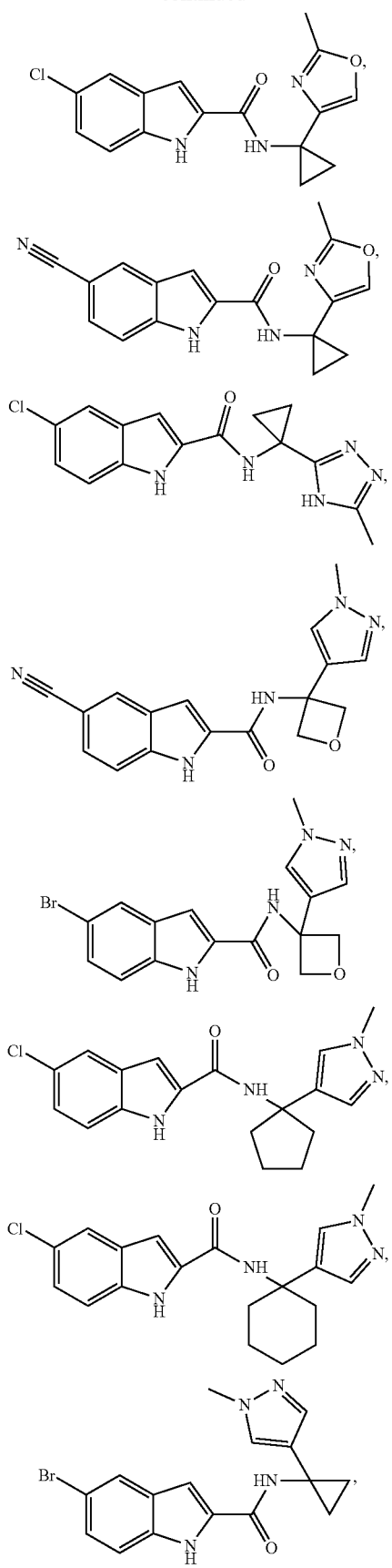
152
-continued
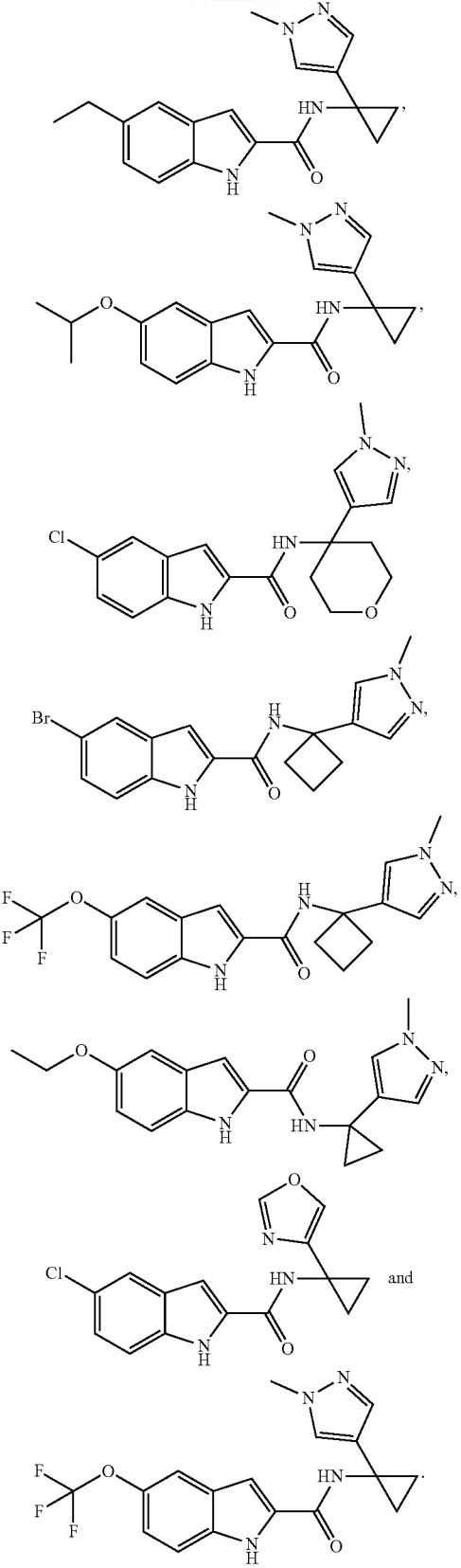
8. A compound according to claim 1, or a pharmaceutically acceptable salt thereof, which compound comprises:

an isolated enantiomer,
a mixture of two or more enantiomers,
a mixture of two or more diastereomers, and/or epimers,
a racemic mixture, and/or
one or more tautomers of the compound.

9. A pharmaceutical composition comprising a compound of claim 1, or a pharmaceutically acceptable salt thereof.

10. The compound according to claim 1 selected from the following, or a pharmaceutically acceptable salt thereof:

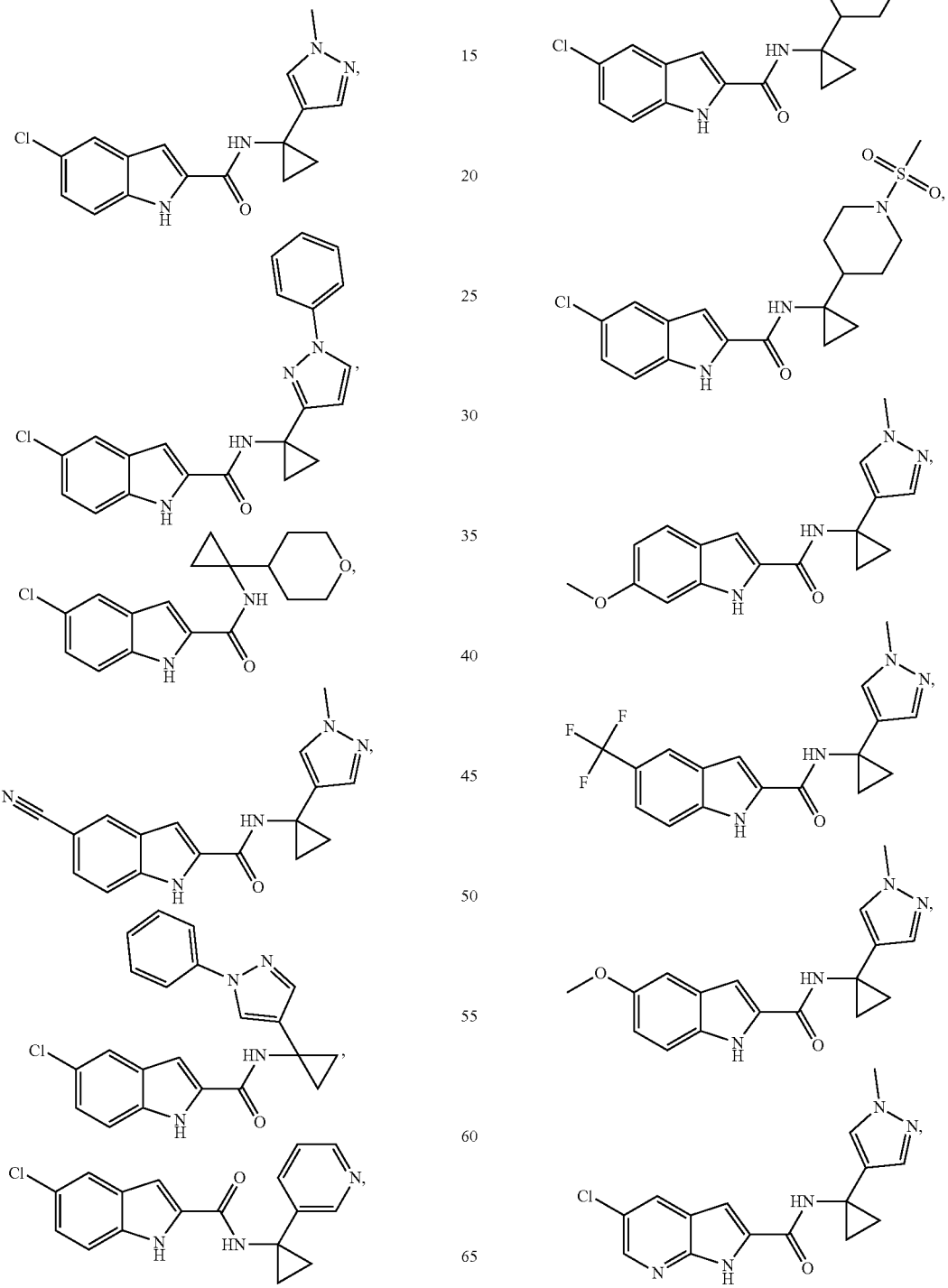

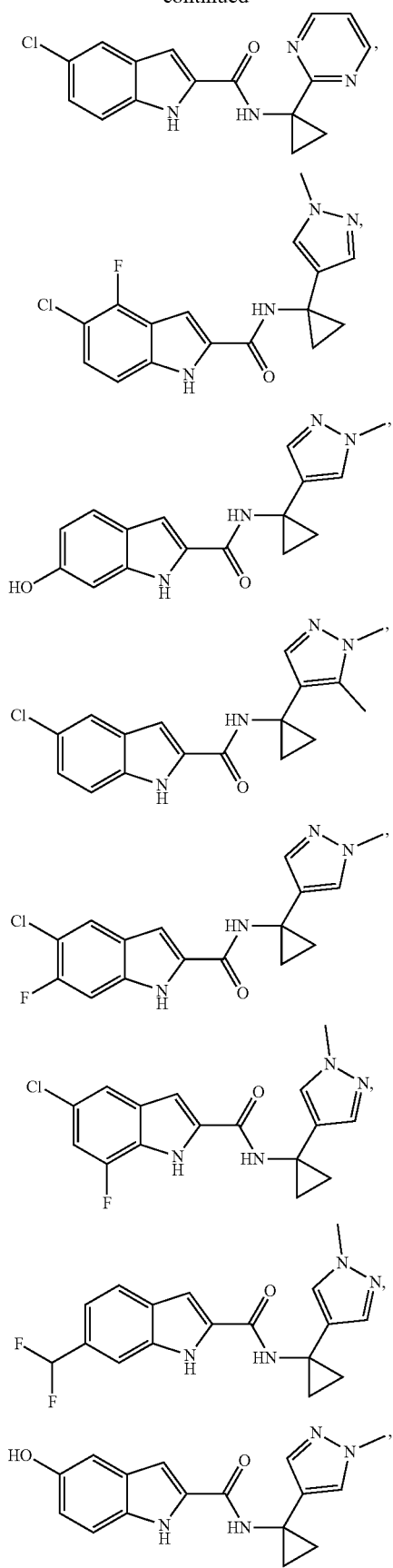
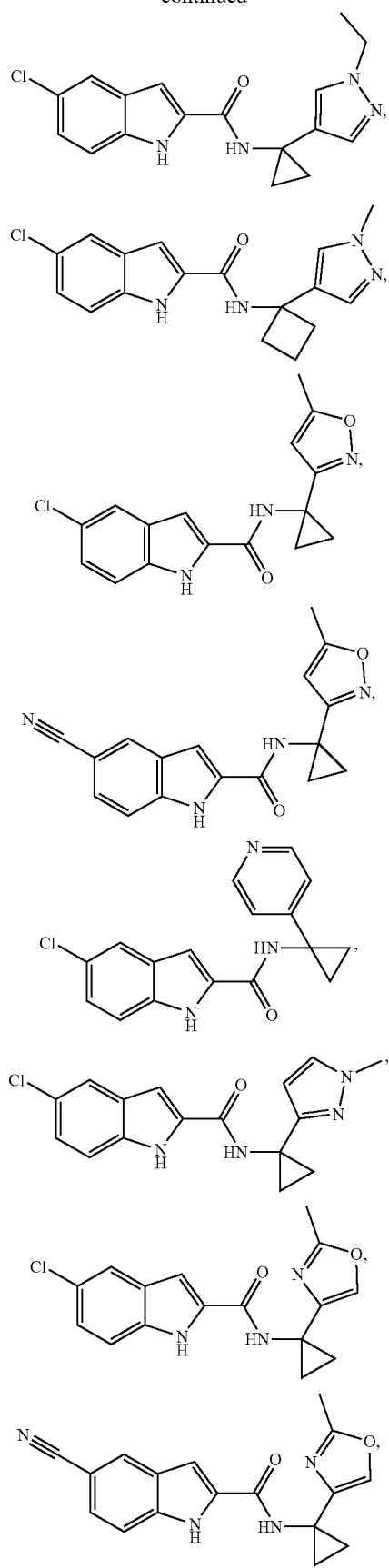

157
-continued
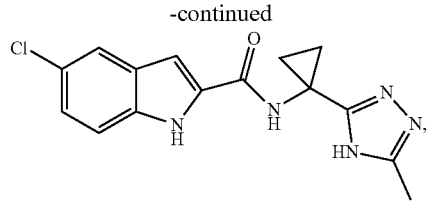
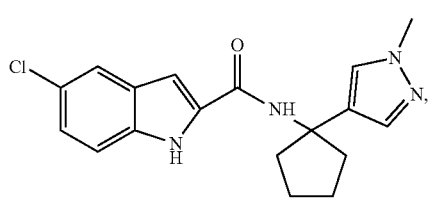
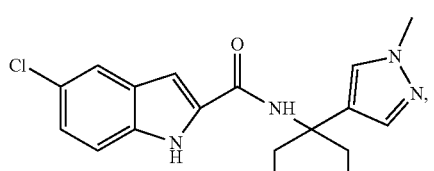
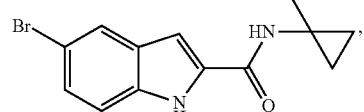
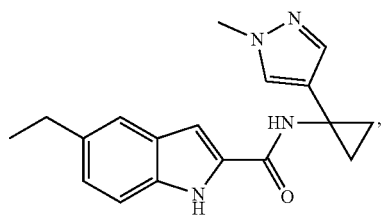
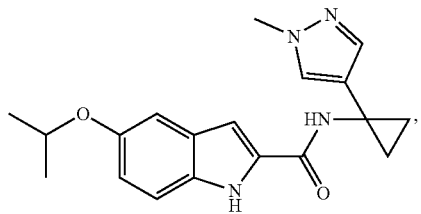
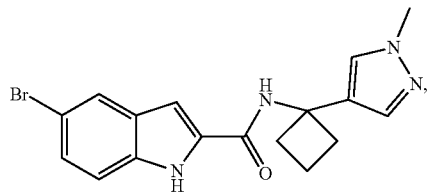
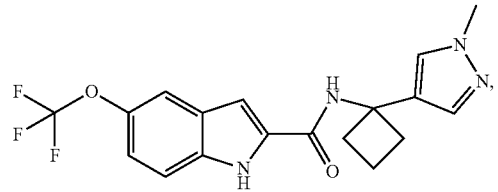
158
-continued
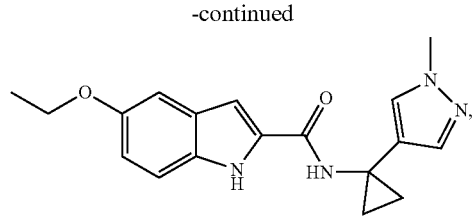
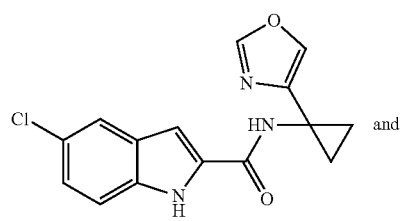
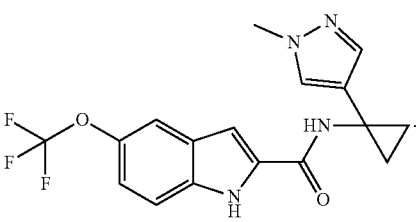
11. The compound according to claim 1 selected from the following, or a pharmaceutically acceptable salt thereof:
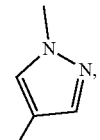
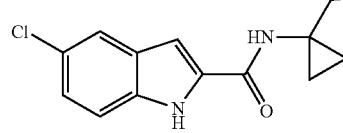
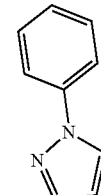
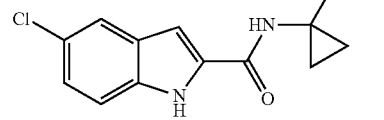
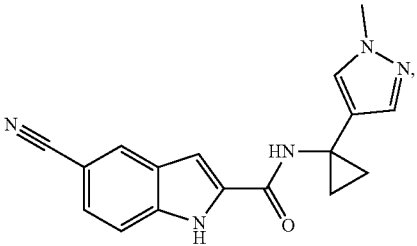

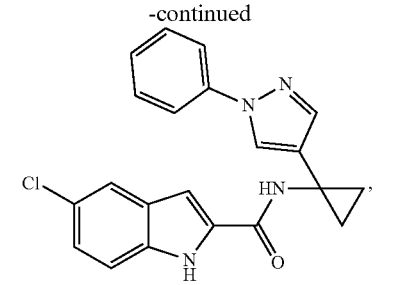
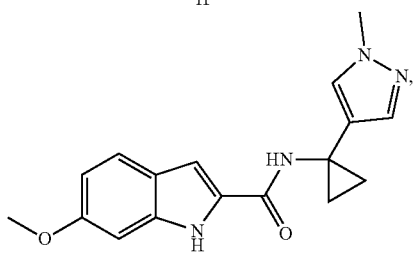
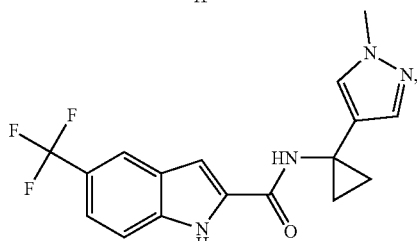
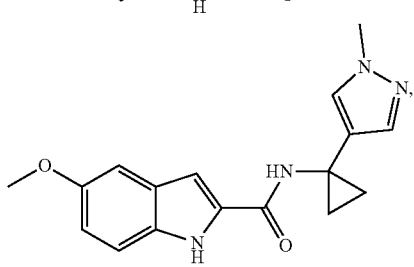
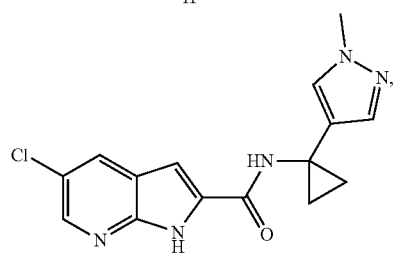
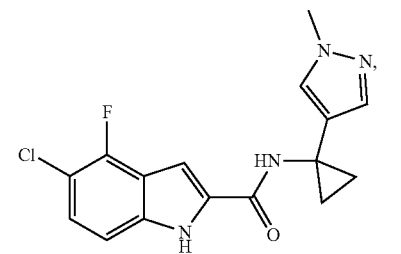
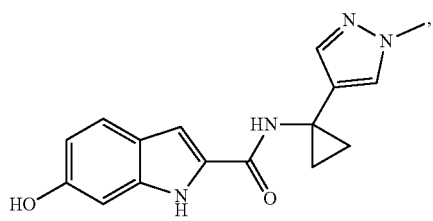
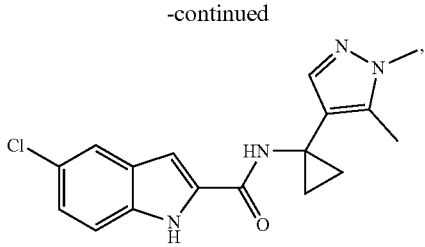
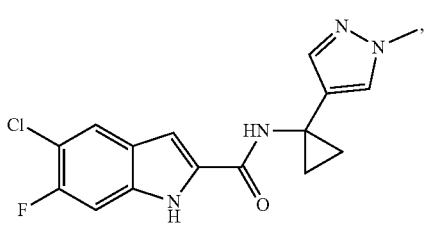
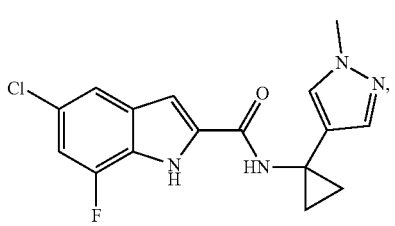
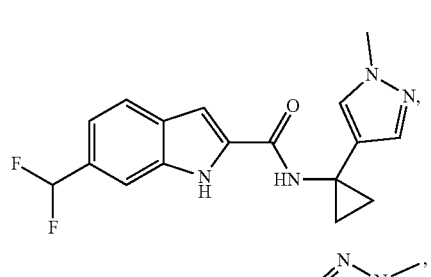
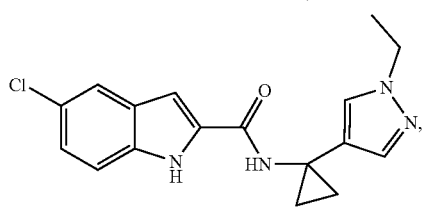
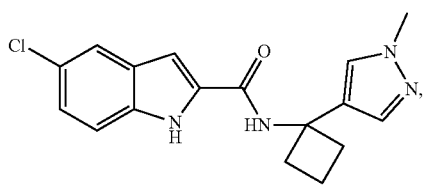
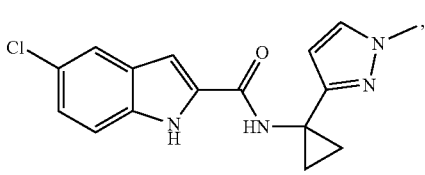

-continued
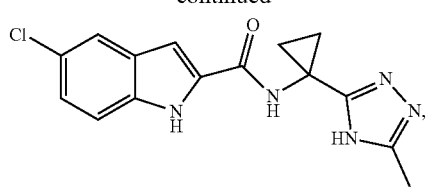
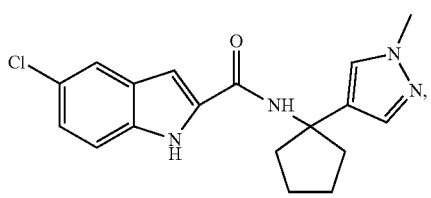
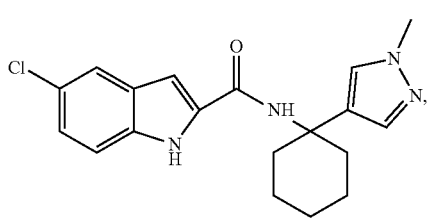
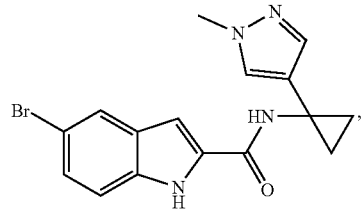
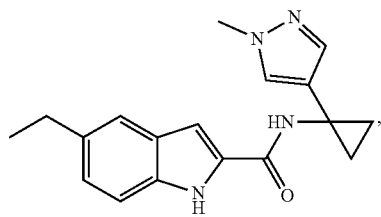
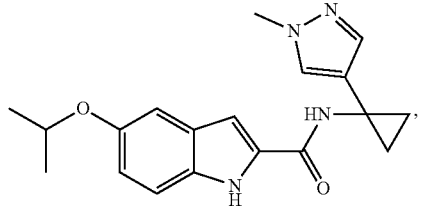
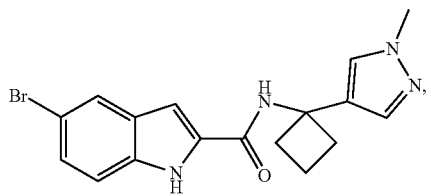
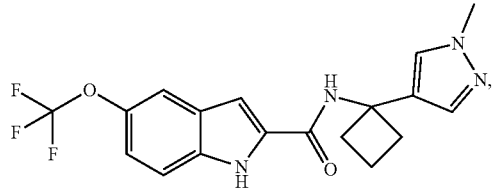
-continued
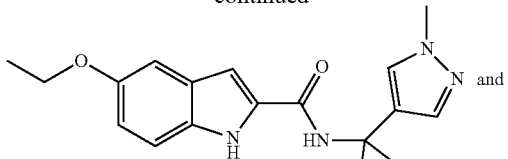
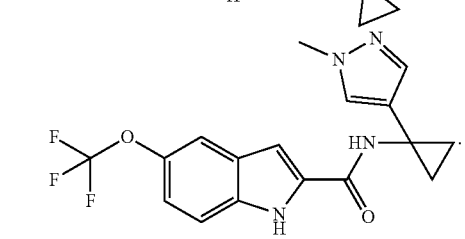
12. The compound according to claim 1 selected from the following, or a pharmaceutically acceptable salt thereof:
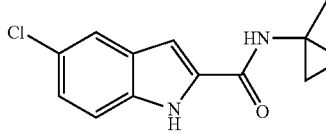
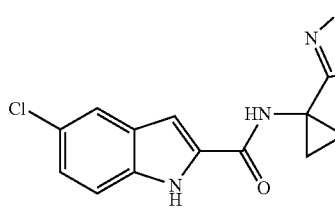
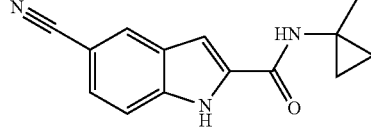
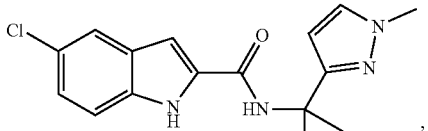
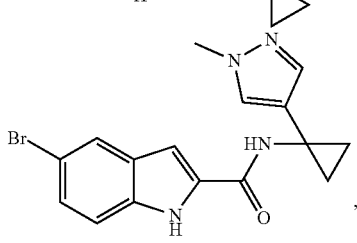

-continued

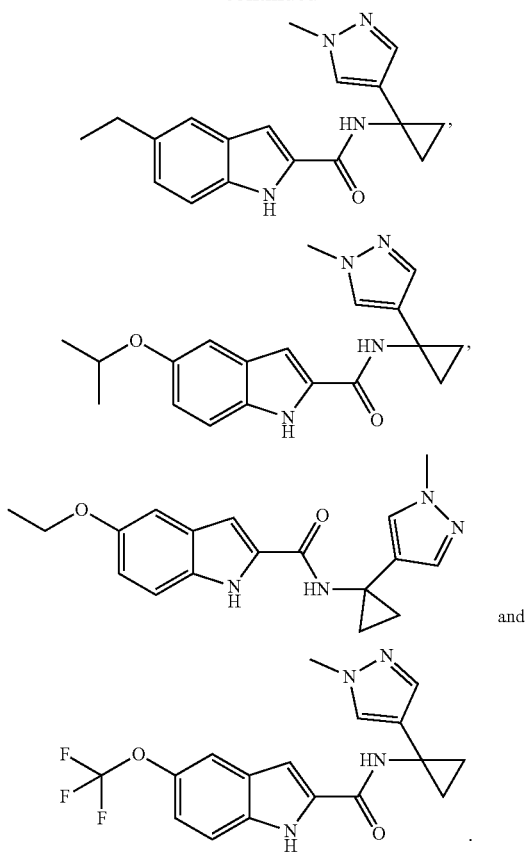

and

13. The compound according to claim 2 of the following formula, or a pharmaceutically acceptable salt thereof:

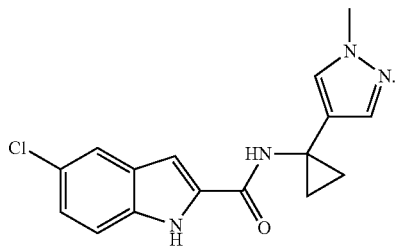 [SMILES: Cn1cc(C2(NC(=O)c3cc4cc(Cl)ccc4[nH]3)CC2)cn1]

14. The compound according to claim 2 of the following formula, or a pharmaceutically acceptable salt thereof:

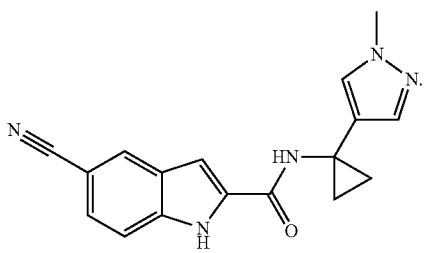 [SMILES: Cn1cc(C2(NC(=O)c3cc4cc(C#N)ccc4[nH]3)CC2)cn1]

15. The compound according to claim 2 of the following formula, or a pharmaceutically acceptable salt thereof:

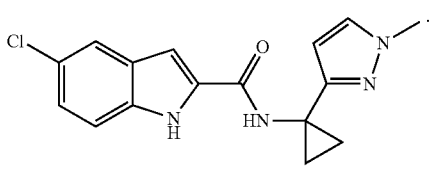 [SMILES: Cn1ccc(C2(NC(=O)c3cc4cc(Cl)ccc4[nH]3)CC2)n1]

16. The compound according to claim 2 of the following formula, or a pharmaceutically acceptable salt thereof:

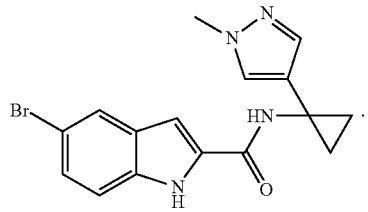 [SMILES: Cn1cc(C2(NC(=O)c3cc4cc(Br)ccc4[nH]3)CC2)cn1]

17. The compound according to claim 2 of the following formula, or a pharmaceutically acceptable salt thereof:

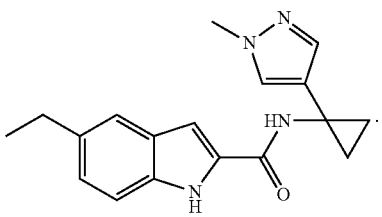 [SMILES: CCc1ccc2[nH]c(C(=O)NC3(c4cnn(C)c4)CC3)cc2c1]

18. The compound according to claim 2, or a pharmaceutically acceptable salt thereof,
wherein:
  each of $R^1$, $R^3$ and $R^4$ is independently selected from H, methyl, ethyl and halogen;
  $R^2$ is selected from H, methyl, ethyl, propyl, —O-methyl, —O-ethyl, —O-propyl, —O-isopropyl, —O—CF$_3$, —CF$_3$, —CHF$_2$, —CN, F, Cl and Br;
  each of $R^5$ and $R^7$ is H;
  $R^{61}$ is selected from H, methyl and ethyl;
  $R^{63}$ and $R^{64}$ together form a 3-6 membered saturated carbocyclic or heterocyclic ring selected from cyclopropyl, cyclobutyl, cyclopentyl, cyclohexyl, aziridinyl, azetidinyl, pyrrolidinyl, piperidinyl, piperazinyl, oxetanyl, tetrahydrofuranyl and tetrahydropyranyl; and
  $R^{65}$ is selected from:
    pyrazol-1-yl, optionally substituted with methyl, ethyl or propyl;
    pyrazol-3-yl, optionally substituted with methyl, ethyl or propyl;
    pyrazol-4-yl, optionally substituted with methyl, ethyl or propyl; and
    pyrazol-5-yl, optionally substituted with methyl, ethyl or propyl.

19. The compound according to claim 18, wherein:
  each of $R^1$, $R^3$ and $R^4$ is independently selected from H, methyl and halogen;
  $R^2$ is selected from methyl, ethyl, —O-methyl, —O-ethyl, F, Cl, Br and —CN;
  each of $R^5$, $R^7$ and $R^{61}$ is H;
  $R^{63}$ and $R^{64}$ together form a 3-6 membered saturated carbocyclic ring selected from cyclopropyl, cyclobutyl, cyclopentyl and cyclohexyl; and $R^{65}$ is selected from:
- pyrazol-1-yl, optionally substituted with methyl, ethyl or propyl;
- pyrazol-3-yl, optionally substituted with methyl, ethyl or propyl;
- pyrazol-4-yl, optionally substituted with methyl, ethyl or propyl; and
- pyrazol-5-yl, optionally substituted with methyl, ethyl or propyl.

20. The compound according to claim 18, wherein:
each of $R^1$, $R^3$ and $R^4$ is H;
$R^2$ is selected from methyl, ethyl, F, Cl, Br and —CN;
each of $R^5$, $R^7$ and $R^{61}$ is H;
$R^{63}$ and $R^{64}$ together form cyclopropyl; and
$R^{65}$ is selected from:
- pyrazol-1-yl, optionally substituted with methyl, ethyl or propyl;
- pyrazol-3-yl, optionally substituted with methyl, ethyl or propyl; and
- pyrazol-4-yl, optionally substituted with methyl, ethyl or propyl.

21. A compound of the following formula:

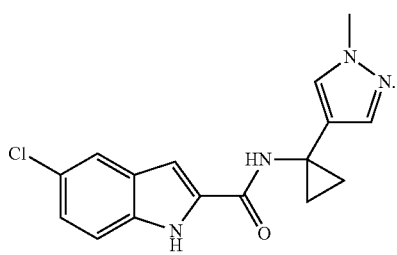 [SMILES: Cn1cc(C2(NC(=O)c3cc4cc(Cl)ccc4[nH]3)CC2)cn1]

22. A compound of the following formula:

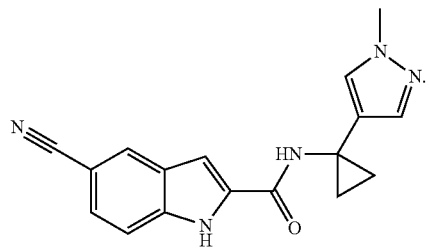 [SMILES: Cn1cc(C2(NC(=O)c3cc4cc(C#N)ccc4[nH]3)CC2)cn1]

23. A compound of the following formula:

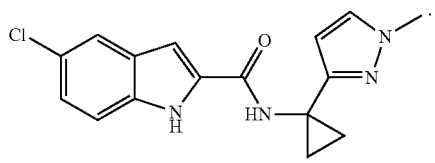 [SMILES: Cn1ccc(C2(NC(=O)c3cc4cc(Cl)ccc4[nH]3)CC2)n1]

24. A compound of the following formula:

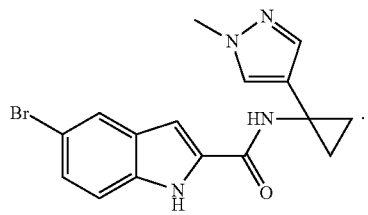 [SMILES: Cn1cc(C2(NC(=O)c3cc4cc(Br)ccc4[nH]3)CC2)cn1]

* * * * *